(12) United States Patent
Kodama et al.

(10) Patent No.: US 8,158,326 B2
(45) Date of Patent: *Apr. 17, 2012

(54) PHOTOSENSITIVE COMPOSITION, COMPOUND FOR USE IN THE PHOTOSENSITIVE COMPOSITION, AND METHOD OF PATTERN FORMATION WITH THE PHOTOSENSITIVE COMPOSITION

(75) Inventors: Kunihiko Kodama, Shizuoka (JP); Kenji Wada, Shizuoka (JP); Kaoru Iwato, Shizuoka (JP)

(73) Assignee: Fujifilm Corporation, Tokyo (JP)

( * ) Notice: Subject to any disclaimer, the term of this patent is extended or adjusted under 35 U.S.C. 154(b) by 135 days.

This patent is subject to a terminal disclaimer.

(21) Appl. No.: 12/191,153

(22) Filed: Aug. 13, 2008

(65) Prior Publication Data

US 2009/0075202 A1    Mar. 19, 2009

Related U.S. Application Data

(62) Division of application No. 11/056,274, filed on Feb. 14, 2005, now Pat. No. 7,449,573.

(30) Foreign Application Priority Data

Feb. 16, 2004 (JP) ................................ 2004-038308

(51) Int. Cl.
*G03F 7/039* (2006.01)
*G03F 7/038* (2006.01)

(52) U.S. Cl. .......... 430/270.1; 522/59; 522/31; 522/27; 522/25; 522/15; 430/921; 430/922; 430/326

(58) Field of Classification Search ............... 522/59
See application file for complete search history.

(56) References Cited

U.S. PATENT DOCUMENTS

| 4,329,478 A | 5/1982 | Behr |
| 5,627,292 A | 5/1997 | Armand et al. |
| 5,691,458 A | 11/1997 | Arnost et al. |
| 6,355,633 B1 | 3/2002 | Wrobel et al. |
| 6,440,634 B1 * | 8/2002 | Ohsawa et al. ............. 430/270.1 |
| 6,841,333 B2 | 1/2005 | Lamanna et al. |
| 7,175,963 B2 * | 2/2007 | Fuji et al. ................... 430/270.1 |
| 7,189,492 B2 * | 3/2007 | Kodama et al. ............. 430/270.1 |
| 7,273,690 B2 * | 9/2007 | Kodama et al. ............. 430/270.1 |
| 7,351,515 B2 * | 4/2008 | Yasunami et al. .......... 430/270.1 |
| 7,465,528 B2 * | 12/2008 | Nishiyama et al. ........ 430/270.1 |
| 2002/0058199 A1 * | 5/2002 | Zampini et al. ............ 430/270.1 |
| 2002/0102491 A1 * | 8/2002 | Kodama et al. ............. 430/270.1 |
| 2002/0197558 A1 * | 12/2002 | Ferreira et al. ............. 430/270.1 |
| 2003/0198894 A1 | 10/2003 | Mizutani et al. |
| 2003/0224284 A1 * | 12/2003 | Tao ............................ 430/270.1 |
| 2004/0067435 A1 * | 4/2004 | Iwato et al. ................. 430/270.1 |
| 2004/0087690 A1 | 5/2004 | Lamanna et al. |
| 2004/0234888 A1 * | 11/2004 | Lamanna .................... 430/270.1 |

FOREIGN PATENT DOCUMENTS

| EP | 1 270 553 A2 | 1/2003 |
| JP | 2001-066779 A | 3/2001 |
| JP | 2002-131897 A | 5/2002 |
| JP | 2002-214774 A | 7/2002 |
| JP | 2003-140332 A | 5/2003 |
| JP | 2003-140344 A | 5/2003 |
| JP | 2003-149800 A | 5/2003 |
| JP | 2003-162059 A | 6/2003 |
| JP | 2003-173022 A | 6/2003 |
| JP | 2003-252855 A | 9/2003 |
| JP | 2003-345022 A | 12/2003 |
| JP | 2004-004557 A | 1/2004 |
| WO | 02/42845 A2 | 5/2002 |

OTHER PUBLICATIONS

English translation of JP, 2001-066779 A (2001) from machine translation from AIPN Japan Patent Office National center for Industrial Property Information and Training, generated Dec. 13, 2009, 76 pages.*
R-1.2.1 SUbstitutive operation, IUPAC, Commisson on Nomenclature of Organic Chemistry, A Guide to IUPAC Nomenclature of Organic compounds (Recommendations 1993, Blackwell Scientific publications obtained at http:..www.acdlabs.com/iupac/nomenclature/93/r93_143.htm, one page downloaded on Jul. 2, 2010.*
"Heat" from http://whatis.tecqtaraet,com/, All Rights Reserved, Copyright 2000-2006, TechTarget copied Sep. 29, 2006, t3 pages last updated Sep. 23, 2001.
Research Disclosure (1979), 180, 139-140 (No. 18032) CODEN:RSDSBB; ISSN: 0374-4353. 4 pages.
Registry Copyright 2006 ACS on STN RN 70795-21-0 Registry ED Entered STN: Nov. 16, 1984.
Blus Kazimierz, "Synthesis and properties of acid dyes derived from 7-amino-1-hydroxynaphthalene-3-sulphonic acid," Dyes and Pigments, vol. 41, Issues 1-2, (1999), pp. 149-157.
Japanese Office Action dated Aug. 12, 2009.

* cited by examiner

*Primary Examiner* — Cynthia Hamilton
(74) *Attorney, Agent, or Firm* — Sughrue Mion, PLLC

(57) ABSTRACT

A compound which generates a sulfonic acid having one or more —$SO_3H$ groups and one or more —$SO_2$— bonds upon irradiation with an actinic ray or a radiation; a photosensitive composition containing the compound; and a method of pattern formation with the photosensitive composition.

30 Claims, 1 Drawing Sheet

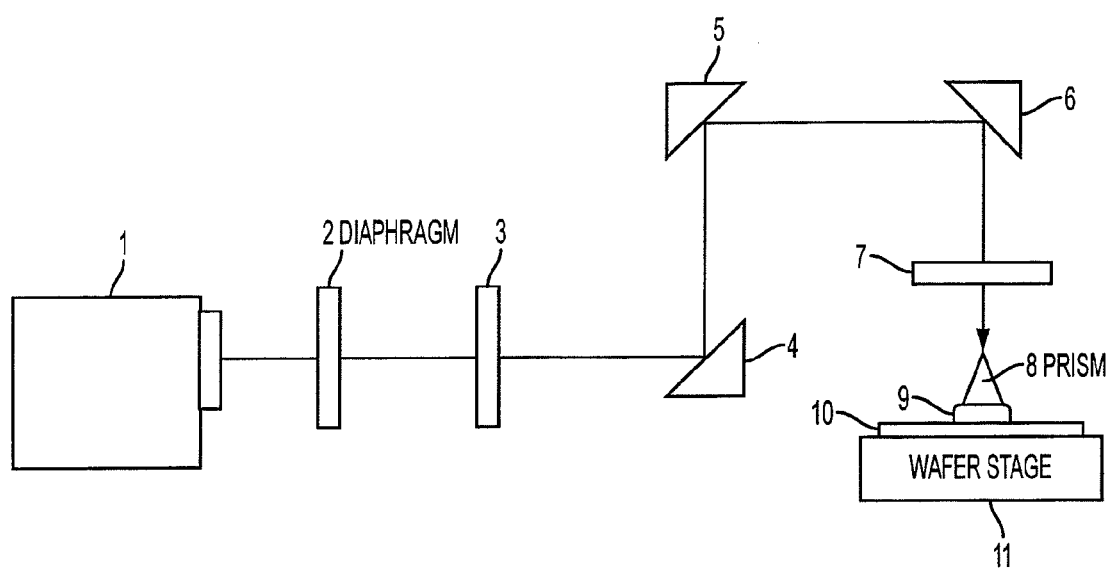

PHOTOSENSITIVE COMPOSITION, COMPOUND FOR USE IN THE PHOTOSENSITIVE COMPOSITION, AND METHOD OF PATTERN FORMATION WITH THE PHOTOSENSITIVE COMPOSITION

This is a Divisional application of U.S. Ser. No. 11/056,274. This application claims foreign priority based on Japanese Patent application No. 2004-038308, filed Feb. 16, 2004, the contents of which are incorporated herein by reference in their entirety.

BACKGROUND OF THE INVENTION

1. Field of the Invention

The present invention relates to a photosensitive composition which reacts upon irradiation with an actinic ray or a radiation to change in property, a compound for use in the photosensitive composition, and a method of pattern formation with the photosensitive composition. More particularly, the invention relates to a photosensitive composition for use in the production of semiconductors, e.g., IC's, production of circuit boards for liquid crystals, thermal heads, etc., and other photofabrication processes and in other applications including lithographic printing plates and acid-curable compositions, and also to a compound for use in the photosensitive composition and a method of pattern formation with the photosensitive composition.

2. Description of the Related Art

A chemical amplification type resist composition is a material for pattern formation which functions by the following mechanism. Upon irradiation with a radiation such as, e.g., far ultraviolet rays, the composition generates an acid in the exposed areas and undergoes a reaction catalyzed by this acid. As a result, the composition comes to have a difference in solubility in a developing solution between the areas irradiated with the actinic radiation and the unirradiated areas to thereby form a pattern on the substrate.

In the case where a KrF excimer laser is employed as an exposure light source, a resin having a poly(hydroxystyrene) backbone which shows reduced absorption mainly in a 248-nm region, is used as the main component. Because of this, the composition has high sensitivity and forms satisfactory patterns with high resolution. It is hence a better system as compared with the naphthoquinonediazide/novolak resin system heretofore in use.

On the other hand, in the case where a light source having a shorter wavelength, e.g., an ArF excimer laser (193 nm), is used as an exposure light source, even the chemical amplification type system has been insufficient because compounds having aromatic groups intrinsically show considerable absorption in a 193-nm region.

Because of this, resists for an ArF excimer laser which contain a resin having an alicyclic hydrocarbon structure have been developed.

As photo-acid generators have been used compounds which generate a perfluoroalkanesulfonic acid such as trifluoromethanesulfonic acid or nonafluorobutanesulfonic acid. Furthermore, photosensitive compositions containing a compound which generates a specific sulfonic acid (see, for example, JP-A-2003-140332, European Patent Application Publication No. 1,270,553 and International Publication No. 02/042845, pamphlet) and photosensitive compositions containing a compound which generates a specific sulfonic acid and a resin which decomposes by the action of an acid to come to have enhanced solubility in an alkaline developer (see, for example, JP-A-2002-131897 and JP-A-2002-214774) have been proposed.

US Patent Application, Laid-open No. 2004/0087690 specification also describes a photo-acid generator containing a sulfonic acid anion having a fluorinated hydrocarbon group.

However, those compositions are still insufficient in many points and various improvements are desired. For example, there is a desire for the prevention of pattern falling and diminution of line edge roughness.

SUMMARY OF THE INVENTION

An object of the invention is to provide a photosensitive composition which is less apt to suffer pattern falling and is effective in reducing line edge roughness, a compound for use in the photosensitive composition, and a method of pattern formation with the photosensitive composition.

The invention has the following constitutions, with which the object of the invention is accomplished.

(1) A photosensitive composition containing (A) a compound which, upon irradiation with an actinic ray or a radiation, generates an acid represented by the following general formula (I) or (I'):

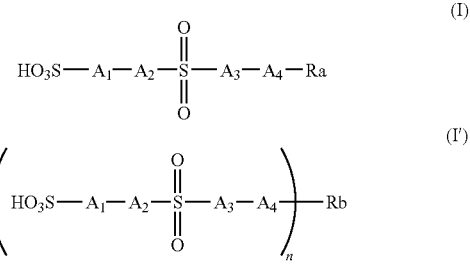

wherein $A_1$ represents a divalent connecting group;

$A_2$ and $A_3$ each independently represents a single bond, an oxygen atom, or —N(Rx)-;

Rx represents a hydrogen atom, an aryl group, an alkyl group, or a cycloalkyl group;

$A_4$ represents a single bond or —C(=O)—;

Ra represents a hydrogen atom or an organic group;

n represents 2 or 3; and

Rb represents a connecting group having a valence of n, provided that when $A_3$ is —N(Rx)-, Rx may be bonded to Ra or Rb to form a ring.

(2) The photosensitive composition as described in (1) above which further contains (B) a resin which decomposes by an action of an acid to a solubility of the resin in an alkaline developer (positive type).

(3) The photosensitive composition as described in (1) above which further contains (D) a resin soluble in an alkaline developer and (E) an acid-sensitive crosslinking agent which, by an action of an acid, crosslinks the resin (D) (negative type).

(4) A compound which, upon irradiation with an actinic ray or a radiation, generates an acid represented by the general formula (I) or (I') described in (1) above.

(5) The compound as described in (4) above wherein the compound which, upon irradiation with an actinic ray or a radiation, generates an acid represented by general formula (I) or (I') is either an onium salt of the sulfonic acid represented by general formula (I) or (I') or an ester compound of the sulfonic acid represented by general formula (I) or (I').

(6) A sulfonic acid represented by general formula (I) or (I') or a salt thereof (e.g., onium salt or metal salt).

(7) The positive type photosensitive composition as described in (2) above wherein the resin (B) comprises a structural unit of hydroxystyrene.

(8) The positive type photosensitive composition as described in (2) above wherein the resin (B) comprises a repeating unit having a monocyclic or polycyclic hydrocarbon structure.

(9) The positive type photosensitive composition as described in (2) above wherein the resin (B) comprises a repeating unit having one or more alcoholic hydroxy groups.

(10) The positive type photosensitive composition as described in (9) above wherein the repeating unit having one or more alcoholic hydroxy groups in the resin (B) is a repeating unit containing at least one member selected from a monohydroxyadamantane structure, a dihydroxyadamantane structure, and a trihydroxyadamantane structure.

(11) The positive type photosensitive composition as described in (2) above wherein the resin (B) comprises a repeating unit having a lactone structure.

(12) The positive type photosensitive composition as described in (2) above wherein the resin (B) comprises: at least one kind of repeating methacrylic ester units; and at least one kind of repeating acrylic ester units.

(13) The positive type photosensitive composition as described in (2) above wherein the resin (B) has a fluorine atom, in other words, has a fluorine atom in the main chain or side chains thereof.

(14) The positive type photosensitive composition as described in (12) above wherein the resin (B) has a hexafluoro-2-propanol structure.

(15) The positive type photosensitive composition as described in any one of (2) and (7) to (14) above which further contains (C) a dissolution inhibitive compound having a molecular weight of 3,000 or lower which decomposes by an action of an acid to increase a solubility of the dissolution inhibitive compound in an alkaline developer.

(16) The photosensitive composition as described in any one of (2), (3), and (7) to (14) above which further contains at least one of: (F) a basic compound and; (G) at least one of a fluorochemical surfactant and a silicone surfactant.

(17) The photosensitive composition as described in (8) above wherein the repeating units having the monocyclic or polycyclic hydrocarbon structure in the resin (B) is a repeating unit which comprises at least one of: at lease one kind of a repeating unit derived from a member selected from 2-alkyl-2-adamantyl (meth)acrylate and dialkyl(1-adamantyl)methyl (meth)acrylate; at least one kind of a repeating unit having a lactone structure; and at least one kind of a repeating unit having one or more hydroxy groups.

(18) The photosensitive composition as described in (17) above wherein the resin (B) further comprises a repeating unit having a carboxy group.

(19) The photosensitive composition as described in (2) above wherein ingredient (B) comprises at least one of: at least one kind of a repeating unit derived from a member selected from 2-alkyl-2-adamantyl (meth)acrylate and dialkyl(1-adamantyl)methyl (meth)acrylate; and at least one kind of a repeating unit having a hydroxystyrene structure.

(20) A method of pattern formation comprising: forming a film with a photosensitive composition as described in any one of (1) to (3) and (7) to (19) above; exposing the film to form an exposed film; and developing the exposed film.

BRIEF DESCRIPTION OF THE DRAWINGS

FIG. 1 is a schematic drawing of an experimental two-beam interference exposure apparatus.

DETAILED DESCRIPTION OF THE INVENTION

The invention will be explained below in detail.

With respect to expressions of groups (atomic groups) in this specification, the expressions which include no statement as to whether the groups are substituted or unsubstituted imply both of groups having no substituents and groups having one or more substituents. For example, the term "alkyl group" implies not only an alkyl group having no substituents (unsubstituted alkyl group) but also an alkyl group having one or more substituents (substituted alkyl group).

The positive type photosensitive composition, more preferably, positive resist composition, of the invention comprises a compound (A) which generates an acid represented by general formula (I) or (I') upon irradiation with an actinic ray or a radiation and a resin (B) which decomposes by the action of an acid to come to have enhanced solubility in an alkaline developer, and optionally further contains a dissolution inhibitive compound (C) having a molecular weight of 3,000 or lower which decomposes by the action of an acid to come to have enhanced solubility in an alkaline developer. Alternatively, the composition comprises a compound (A) which generates an acid represented by general formula (I) or (I') upon irradiation with an actinic ray or a radiation, a resin (D) soluble in an alkaline developer, and a dissolution inhibitive compound (C) having a molecular weight of 3,000 or lower which decomposes by the action of an acid to come to have enhanced solubility in an alkaline developer.

The negative type photosensitive composition, more preferably, negative resist composition, of the invention comprises a compound (A) which generates an acid represented by general formula (I) or (I') upon irradiation with an actinic ray or a radiation, a resin (D) soluble in an alkaline developer, and an acid-sensitive crosslinking agent (E) which, by the action of an acid, crosslinks the resin soluble in an alkaline developer.

[1] Compound Generating Acid Represented by General Formula (I) or (I') Upon Irradiation with Actinic Ray or Radiation The photosensitive composition of the invention contains a compound which generates a sulfonic acid represented by the following general formula (I) or (I') upon irradiation with an actinic ray or a radiation (hereinafter referred to also as "compound (A)").

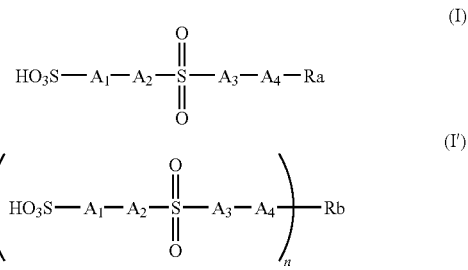

In general formulae (I) and (I'),
$A_1$ represents a divalent connecting group;
$A_2$ and $A_3$ each independently represents a single bond, an oxygen atom, or —N(Rx)-;

Rx represents a hydrogen atom, an aryl group, an alkyl group, or a cycloalkyl group;

$A_4$ represents a single bond or —C(=O)—;

Ra represents a hydrogen atom or an organic group;

n represents 2 or 3; and

Rb represents a connecting group having a valence of n, provided that when $A_3$ is —N(Rx)-, Rx may be bonded to Ra or Rb to form a ring.

The divalent connecting group represented by $A_1$ preferably is an organic group having 1-20 carbon atoms, and more preferably is an alkylene group (having preferably 1-10 carbon atoms, more preferably 2-6 carbon atoms, even more preferably 3 or 4 carbon atoms). The alkylene chain may have an oxygen or sulfur atom or a connecting group, e.g., a —C(=O)— group or ester group, therein.

The divalent connecting group represented by $A_1$ even more preferably is an alkylene group substituted by one or more fluorine atoms. Especially preferred is an alkylene group in which 30-100% by number of the hydrogen atoms have been substituted by fluorine atoms. In the case where $A_1$ is an alkylene group substituted by fluorine atoms, the carbon atom bonded to the —$SO_3H$ group preferably has one or more fluorine atoms. This alkylene group more preferably is a perfluoroalkylene group, and most preferably is a perfluoroethylene, perfluoropropylene, or perfluorobutylene group.

The aryl group represented by Rx is an aryl group which preferably has 6-14 carbon atoms and may have one or more substituents. Examples thereof include phenyl and naphthyl.

The alkyl group represented by Rx is a linear or branched alkyl group which preferably has 1-20 carbon atoms and may have one or more substituents. The alkyl chain may have an oxygen atom, a sulfur atom or a nitrogen atom therein. Examples of the alkyl group include linear alkyl groups such as methyl, ethyl, n-propyl, n-butyl, n-pentyl, n-hexyl, n-octyl, n-dodecyl, n-tetradecyl, and n-octadecyl and branched alkyl groups such as isopropyl, isobutyl, t-butyl, neopentyl, and 2-ethylhexyl.

Examples of the alkyl group having one or more substituents include, in particular, linear or branched alkyl groups substituted by a cycloalkyl group (e.g., adamantylmethyl, adamantylethyl, cyclohexylethyl, and camphor residues).

The cycloalkyl group represented by Rx is a cycloalkyl group which preferably has 3-20 carbon atoms and may have one or more substituents. This group may have an oxygen atom in the ring. Examples of the cycloalkyl group include cyclopropyl, cyclopentyl, cyclohexyl, norbornyl, and adamantyl.

Ra represents a hydrogen atom or a monovalent organic group.

The monovalent organic group represented by Ra preferably has 1-20 carbon atoms. Examples thereof include alkyl groups, cycloalkyl groups, aryl groups, aralkyl groups, and alkenyl groups.

Examples of the alkyl, cycloalkyl, or aryl group represented by Ra are the same as the groups enumerated above as examples of Rx.

Examples of the aralkyl group represented by Ra include aralkyl groups preferably having 7-20 carbon atoms. Specific examples thereof include benzyl, phenethyl, naphthylmethyl, and naphthylethyl.

Examples of the alkenyl group represented by Ra include those alkyl groups enumerated above as examples of Rx which have a double bond in any desired position.

The n-valent connecting group represented by Rb preferably has 1-20 carbon atoms. When n=2 in general formula (I'), examples of the divalent connecting group represented by Rb include alkylene groups (preferably having 1-20 carbon atoms), arylene groups (preferably having 6-10 carbon atoms), aralkylene groups (preferably having 7-13 carbon atoms), and alkenylene groups (preferably having 2-12 carbon atoms). These groups may have substituents.

When n=3, examples of the trivalent connecting group represented by Rb include trivalent groups formed by removing any desired hydrogen atom from each of the divalent connecting groups shown above.

Examples of substituents which may be possessed by those groups include halogen atoms, hydroxy, nitro, cyano, carboxy, carbonyl group, cycloalkyl groups (preferably having 3-20 carbon atoms), aryl groups (preferably having 6-14 carbon atoms), alkoxy groups (preferably having 1-20 carbon atoms), acyl groups (preferably having 2-20 carbon atoms), acyloxy groups (preferably having 2-20 carbon atoms), an alkoxycarbonyl group (preferably with 2 to 20 carbon atoms) and an aminoacyl group (preferably with 2 to 20 carbon atoms). With respect to cyclic structures such as aryl and cycloalkyl groups, examples of the substituents further include alkyl groups (preferably having 1-20 carbon atoms). As the aminoacyl group, those having one or two more alkyl groups (preferably with 1 to 20 carbon atoms) as substituent(s) can be mentioned.

The sulfonic acids represented by general formulae (I) and (I') preferably are sulfonic acids represented by the following general formulae (IA) to (IC) and (I'A) to (I'C).

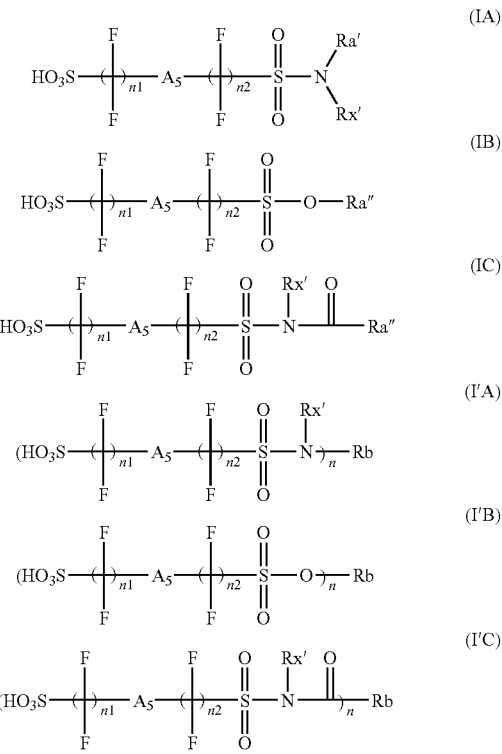

In general formulae (IA) to (IC) and (I'A) to (I'C),

Ra' has the same meaning as the Ra in general formula (I);

Rb and n have the same meanings as the Rb and n in general formula (I');

Ra" represents an alkyl group, aryl group, aralkyl group, or alkenyl group;

Rx' has the same meaning as the Rx in general formulae (I) and (I');

n1 represents an integer of 1 to 10;

n2 represents an integer of 0 to 10; and $A_5$ represents an alkylene group or arylene group.

The alkylene group represented by $A_5$ preferably is an alkylene or cycloalkylene group which has not been substituted by fluorine.

In formula (IA), Ra' and Rx' preferably are bonded to each other to form a ring. The sulfonic acid having a ring structure thus formed has improved stability and the composition containing this acid has improved storage stability. The ring formed preferably has 4-20 carbon atoms and may be monocyclic or polycyclic. It may contain an oxygen atom, a sulfur atom or a nitrogen atom therein.

As the monocyclic structure, 4-membered, 5-membered, 6-membered, 7-membered and 8-membered rings can be cited. As the polycyclic structure, those comprising combinations of two, three or more of monocyclic structures can be cited. These cyclic structures may contain an oxygen atom or a sulfur atom. The monocyclic and polycyclic structures may have a substituent preferably such as, for example, a halogen atom, hydroxy group, cyano group, a carboxy group, a carbonyl group, a cycloalkyl group (preferably with 3 to 10 carbon atoms), an aryl group (preferably with 6 to 14 carbon atoms), an alkoxy group (preferably with 1 to 10 carbon atoms), an acyl group (preferably with 2 to 15 carbon atoms), an acyloxy group (preferably with 2 to 15 carbon atoms), an alkoxycarbonyl group (preferably with 2 to 15 carbon atoms), an aminoacyl group (preferably with 2 to 20 carbon atoms). With respect to the cyclic structure such as an aryl group or a cycloalkyl group, an alkyl group (preferably with 1 to 15 carbon atoms) as a substituent is more preferred. With respect to the aminoacyl group, one or two alkyl groups (preferably with 1 to 15 carbon atoms) as substituents are preferred.

Examples of the alkyl, aryl, aralkyl, or alkenyl group represented by Ra include the same groups as those enumerated above as examples of the alkyl, aryl, aralkyl, or alkenyl group represented by Ra.

n1+n2 is preferably 2 to 8, more preferably 2 to 6.

Preferred examples of the sulfonic acid represented by general formula (I) or (I') are shown below, but the acid in the invention should not be construed as being limited to these examples.

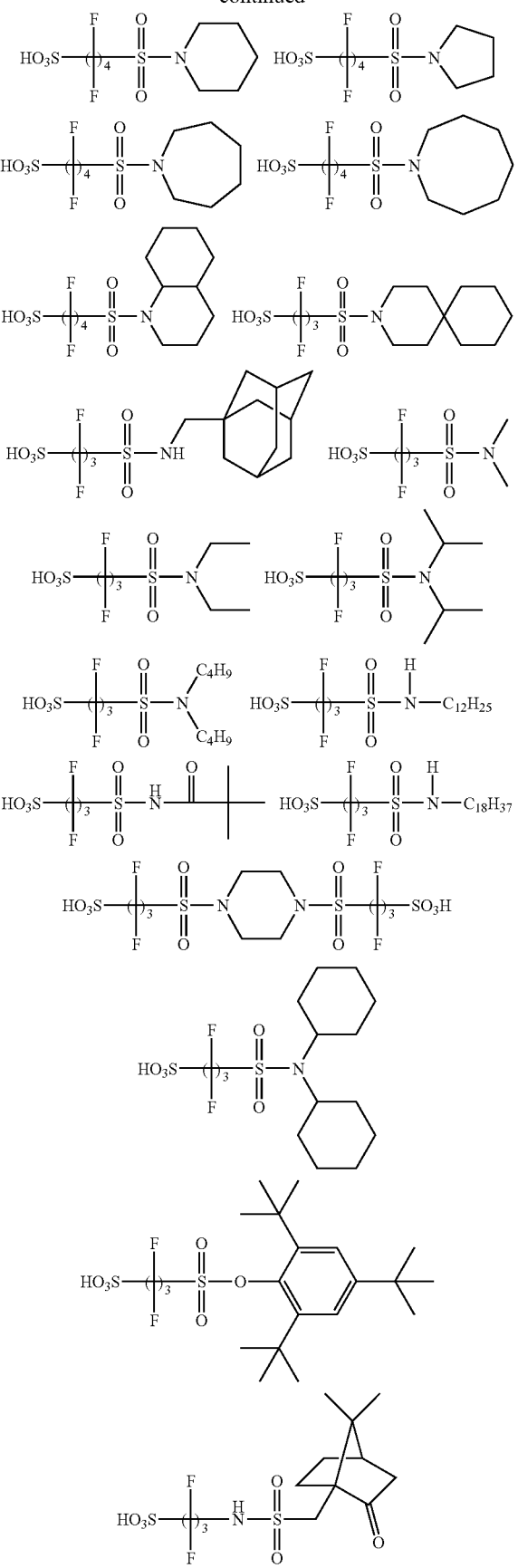

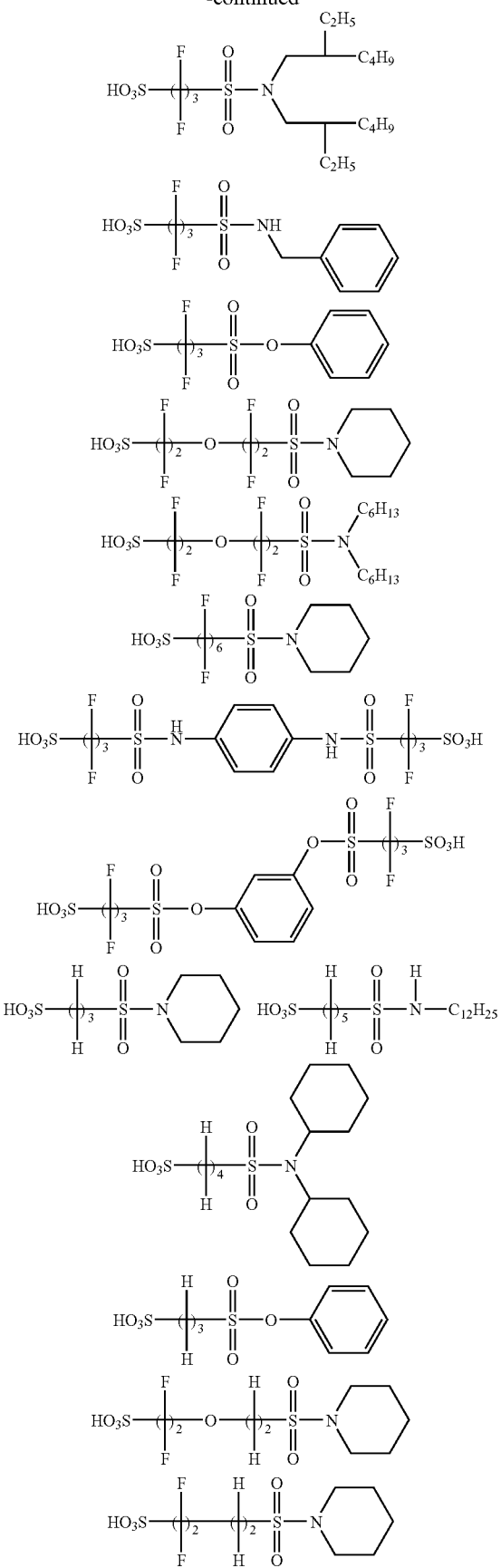
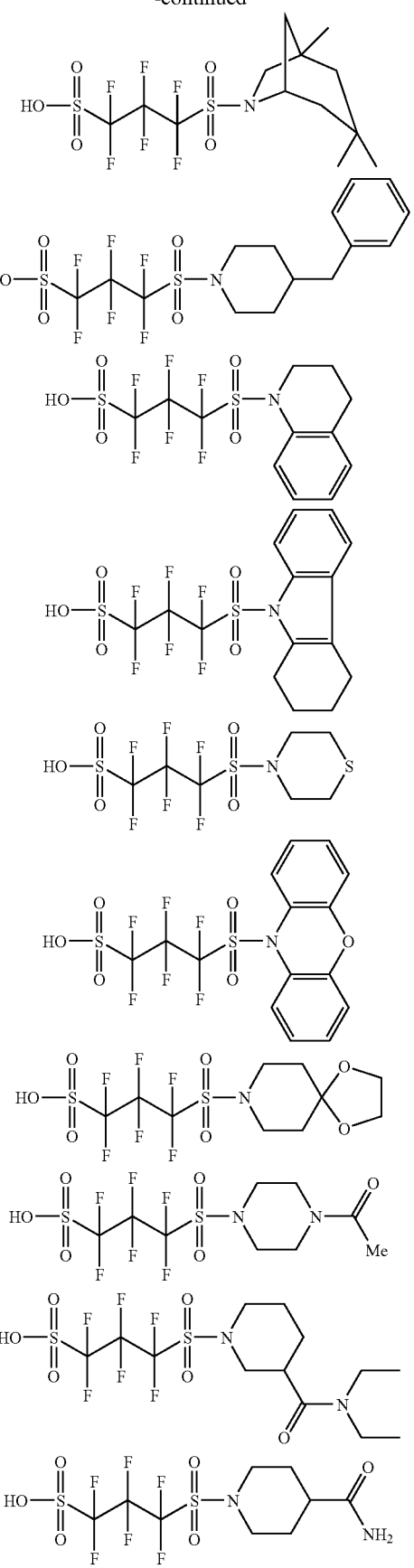

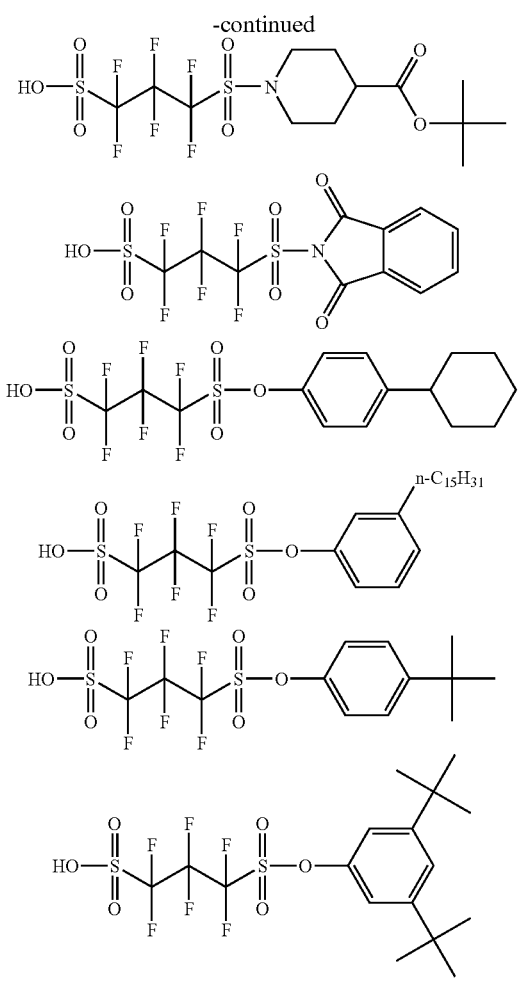

The compound (A) which generates a sulfonic acid represented by general formula (I) or (I') upon irradiation with an actinic ray or a radiation preferably is one member selected from sulfonium salt compounds or iodonium salt compounds of the sulfonic acid represented by general formula (I) or (I') or one member selected from ester compounds of the sulfonic acid represented by general formula (I) or (I'). The compound (A) more preferably is a compound represented by any of the following general formulae (A1) to (A5).

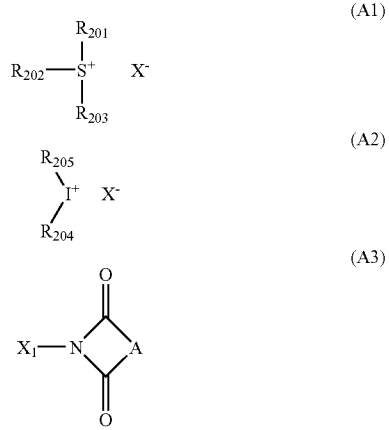

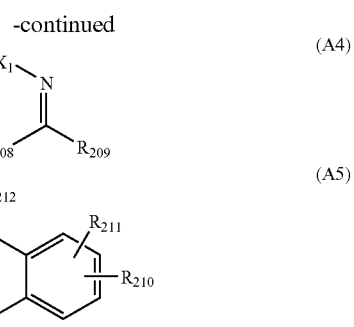

In general formula (A1), $R_{201}$, $R_{202}$, and $R_{203}$ each independently represents an organic group.

$X^-$ represents the sulfonic acid anion formed by removing the hydrogen atom of the —$SO_3H$ in the sulfonic acid represented by general formula (I) or (I').

The number of carbon atoms in each of the organic groups represented by $R_{201}$, $R_{202}$, and $R_{203}$ is generally 1 to 30, preferably 1 to 20.

Two of $R_{201}$ to $R_{203}$ may be bonded to each other to form a ring structure, which may contain an oxygen atom, sulfur atom, ester bond, amide bond, or carbonyl group therein.

Examples of the group formed by the bonding of two of $R_{201}$ to $R_{203}$ include alkylene groups (e.g., butylene and pentylene).

Examples of the organic groups represented by $R_{201}$, $R_{202}$, and $R_{203}$ include the corresponding groups in compounds (A1a), (A1b), and (A1c) which will be described later.

The compound (A) may be a compound having two or more structures represented by general formula (A1). For example, it may be a compound having a structure in which at least one of the $R_{201}$ to $R_{203}$ of a compound represented by general formula (A1) is bonded to at least one of the $R_{201}$ to $R_{203}$ of another compound represented by general formula (A1).

Preferred examples of ingredient (A1) include compounds (A1a), (A1b), and (A1c) explained below.

Compound (A1a) is an arylsulfonium compound represented by general formula (A1) wherein at least one of $R_{201}$ to $R_{203}$ is an aryl group, i.e., a compound including an arylsulfonium as a cation.

The arylsulfonium compound may be one in which all of $R_{201}$ to $R_{203}$ are aryl groups, or may be one in which part of $R_{201}$ to $R_{203}$ is an aryl group and the remainder is an alkyl or cycloalkyl group.

Examples of the arylsulfonium compound include triarylsulfonium compounds, diarylalkylsulfonium compounds, and aryldialkylsulfonium compounds.

The aryl group of the arylsulfonium compound preferably is phenyl or naphthyl, and more preferably is phenyl. In the case where the arylsulfonium compound has two or more aryl groups, these aryl groups may be the same or different.

The alkyl group which is optionally possessed by the arylsulfonium compound preferably is a linear or branched alkyl group having 1-15 carbon atoms. Examples thereof include methyl, ethyl, propyl, n-butyl, sec-butyl, and t-butyl. The cycloalkyl group preferably has 3-15 carbon atoms, and examples thereof include cyclopropyl, cyclobutyl, and cyclohexyl.

The aryl, alkyl, and cycloalkyl groups represented by $R_{201}$ to $R_{203}$ may have substituents selected from alkyl groups (e.g., ones having 1-15 carbon atoms), aryl groups (e.g., ones having 6-14 carbon atoms), alkoxy groups (e.g., ones having 1-15 carbon atoms), halogen atoms, hydroxy, and phenylthio.

Preferred examples of the substituents are linear or branched alkyl groups having 1-12 carbon atoms, cycloalkyl groups having 3-12 carbon atoms, and linear, branched, or cyclic alkoxy groups having 1-12 carbon atoms. Most preferred are alkyl groups having 1-4 carbon atoms and alkoxy groups having 1-4 carbon atoms. Any one of $R_{201}$ to $R_{203}$ may have such a substituent or each of $R_{201}$ to $R_{203}$ may have such a substituent. In the case where $R_{201}$ to $R_{203}$ are aryl groups, it is preferred that a substituent be bonded to the p-position in each aryl group.

Next, compound (A1b) will be explained.

Compound (A1b) is a compound represented by formula (A1) wherein $R_{201}$ to $R_{203}$ each independently represents an organic group containing no aromatic ring. The term aromatic ring herein implies any of aromatic rings including ones containing one or more heteroatoms.

The organic groups containing no aromatic ring which are represented by $R_{201}$ to $R_{203}$ each have generally 1-30, preferably 1-20 carbon atoms.

Preferably, $R_{201}$ to $R_{203}$ each independently are an alkyl group, a cycloalkyl group, a linear, branched, or cyclic oxoalkyl group which may have a double bond in the chain, an alkoxycarbonylmethyl group, allyl, or vinyl. $R_{201}$ to $R_{203}$ each more preferably are a linear, branched, or cyclic 2-oxoalkyl group, and most preferably are a linear or branched 2-oxoalkyl group.

The alkyl groups represented by $R_{201}$ to $R_{203}$ may be either linear or branched. Preferred examples thereof include linear or branched alkyl groups having 1-20 carbon atoms (e.g., methyl, ethyl, propyl, butyl, and pentyl).

The cycloalkyl groups represented by $R_{201}$ to $R_{203}$ preferably have 3-10 carbon atoms. Examples thereof include cyclopentyl, cyclohexyl, and norbornyl.

The 2-oxoalkyl groups represented by $R_{201}$ to $R_{203}$ may be either linear, branched, or cyclic. Preferred examples thereof include the alkyl groups enumerated above which each have >C=O in the 2-position.

Examples of the alkyl groups in the alkoxycarbonylmethyl groups represented by $R_{201}$ to $R_{203}$ include alkyl groups having 1-5 carbon atoms (methyl, ethyl, propyl, butyl, and pentyl).

$R_{201}$ to $R_{203}$ may have been further substituted by substituents selected from halogen atoms, alkoxy groups (e.g., ones having 1-5 carbon atoms), hydroxy, cyano, and nitro.

Two of $R_{201}$ to $R_{203}$ may be bonded to each other to form a ring structure, which may contain an oxygen atom, sulfur atom, ester bond, amide bond, or carbonyl group therein. Examples of the group formed by the bonding of two of $R_{201}$ to $R_{203}$ include alkylene groups (e.g., butylene and pentylene).

Compound (A1c) is a compound represented by the following general formula (A1c). Namely, it is a compound having an arylacylsulfonium salt structure.

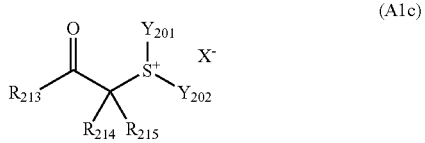

(A1c)

In general formula (A1c), $R_{213}$ represents an optionally substituted aryl group, and preferably is phenyl or naphthyl.

Preferred examples of substituents on $R_{213}$ include alkyl, cycloalkyl, alkoxy, acyl, nitro, hydroxy, alkoxycarbonyl, and carboxy groups.

$R_{214}$ and $R_{215}$ each represent a hydrogen atom or an alkyl or cycloalkyl group.

$Y_{201}$ and $Y_{202}$ each independently represents an alkyl group (examples of substituted alkyl groups include, in particular, 2-oxoalkyl, alkoxycarbonylalkyl, and carboxyalkyl groups), cycloalkyl group, aryl group, or vinyl.

$R_{213}$ and $R_{214}$, $R_{214}$ and $R_{215}$, or $Y_{201}$ and $Y_{202}$ may be bonded to each other to form a ring structure. These ring structures may contain an oxygen atom, sulfur atom, ester bond, or amide bond.

The alkyl groups represented by $Y_{201}$ and $Y_{202}$ preferably are linear or branched alkyl groups having 1-20 carbon atoms.

The cycloalkyl groups represented by $R_{214}$, $R_{215}$, $Y_{201}$, and $Y_{202}$ preferably are cycloalkyl groups having 3-20 carbon atoms.

Examples of the 2-oxoalkyl group include those alkyl groups shown above as examples of $Y_{201}$ and $Y_{202}$ which each have >C=O in the 2-position.

The alkoxycarbonyl group in the alkoxycarbonylalkyl group preferably is an alkoxycarbonyl group having 2-20 carbon atoms.

Examples of the group formed by the bonding of $Y_{201}$ and $Y_{202}$ include butylene and pentylene.

$Y_{201}$ and $Y_{202}$ each preferably are an alkyl group having 4 or more carbon atoms, and more preferably are an alkyl group having 4-16 carbon atoms, even more preferably 4-12 carbon atoms.

It is preferred that at least either of $R_{214}$ and $R_{215}$ be an alkyl group. More preferably, each of $R_{214}$ and $R_{215}$ is an alkyl group.

In general formula (A2), $X^-$ represents the sulfonic acid anion formed by removing the hydrogen atom of the —SO₃H in the sulfonic acid represented by formula (I) or (I'); and $R_{204}$ and $R_{205}$ each independently represents an aryl, alkyl, or cycloalkyl group.

The aryl groups represented by $R_{204}$ and $R_{205}$ preferably are phenyl and naphthyl, and more preferably are phenyl.

The alkyl groups represented by $R_{204}$ and $R_{205}$ may be either linear or branched, and each preferably are a linear or branched alkyl group having 1-10 carbon atoms (e.g., methyl, ethyl, propyl, butyl, or pentyl).

The cycloalkyl groups represented by $R_{204}$ and $R_{205}$ preferably have 3-10 carbon atoms. Examples thereof include cyclopentyl, cyclohexyl, and norbornyl.

Examples of substituents which may be possessed by the groups represented by $R_{204}$ and $R_{205}$ include alkyl groups (e.g., ones having 1-15 carbon atoms), aryl groups (e.g., ones having 6-15 carbon atoms), alkoxy groups (e.g., ones having 1-15 carbon atoms), halogen atoms, hydroxy, and phenylthio.

In general formulae (A3) to (A5), $X_1$ represents the monovalent group formed by removing the hydrogen atom of the —SO₃H in the sulfonic acid represented by general formula (I) or (I).

In general formula (A3), A represents an alkylene, alkenylene, or arylene group, which preferably has 1-6 carbon atoms.

In general formula (A4), $R_{208}$ represents an alkyl, cycloalkyl, or aryl group; and $R_{209}$ represents an alkyl group (examples of substituted alkyl groups include, in particular, oxoalkyl groups), cycloalkyl group, cyano, or alkoxycarbonyl group. Preferably, $R_{209}$ is a halogen-substituted alkyl group or cyano.

The alkyl or cycloalkyl groups represented by $R_{208}$ and $R_{209}$ are the same as the alkyl or cycloalkyl groups represented by $R_{204}$ and $R_{205}$.

The aryl group represented by $R_{208}$ is the same as the aryl groups represented by $R_{204}$ to $R_{205}$.

The alkoxycarbonyl group represented by $R_{209}$ preferably has 2-11 carbon atoms. Examples thereof include methoxycarbonyl, ethoxycarbonyl, propoxycarbonyl, and butoxycarbonyl.

In general formula (A5), $R_{210}$ and $R_{211}$ each represent a hydrogen atom or an alkyl, cycloalkyl, cyano, nitro, or alkoxycarbonyl group, and preferably are a halogen-substituted alkyl group, nitro, or cyano; and $R_{212}$ represents a hydrogen atom or an alkyl, cycloalkyl, cyano, or alkoxycarbonyl group.

The alkyl or cycloalkyl groups represented by $R_{210}$ to $R_{212}$ are the same as the alkyl or cycloalkyl groups represented by $R_{204}$ and $R_{205}$ described above.

The alkoxycarbonyl group represented by $R_{212}$ is the same as the alkoxycarbonyl group represented by $R_{209}$.

Preferred of the compounds represented by general formulae (A1) to (A5) are the compounds represented by general formula (A1). More preferred are the compounds (A1a) to (A1c).

Preferred examples of the compound (A) which generates an acid represented by general formula (I) or (I') by the action of an actinic ray or a radiation are shown below, but the compound in the invention should not be construed as being limited to these examples.

I-1

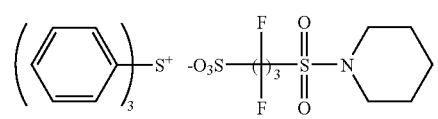

I-2

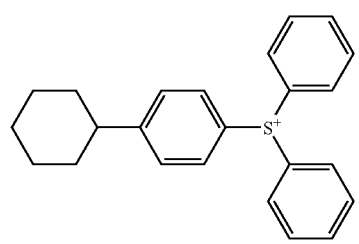

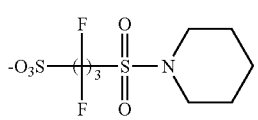

I-3

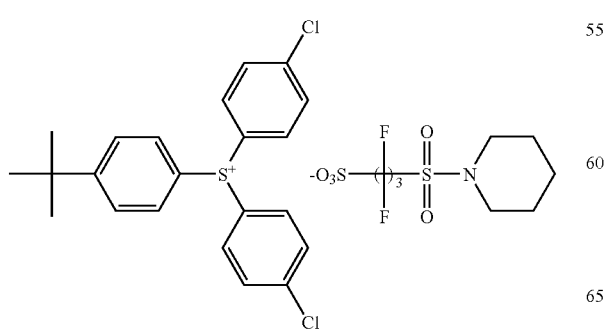

I-4

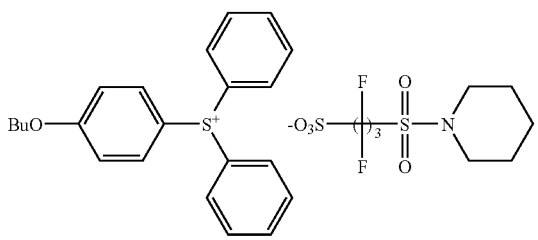

I-5

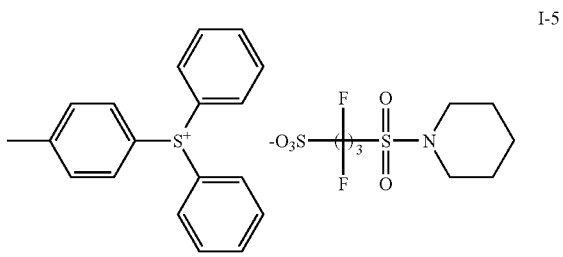

I-6

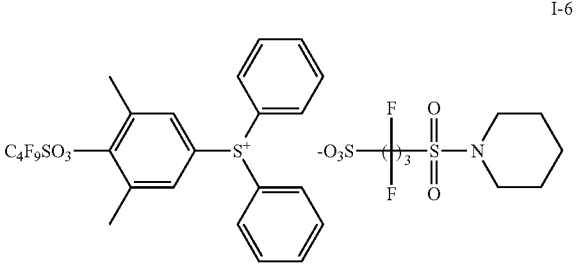

I-7

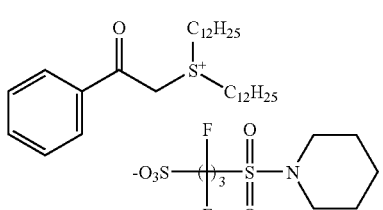

I-8

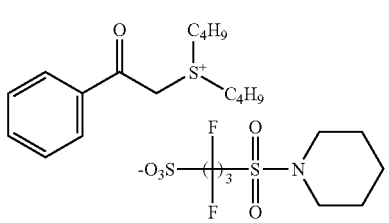

I-9

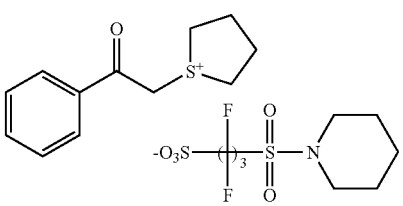

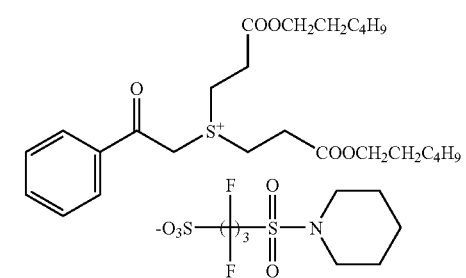
I-10
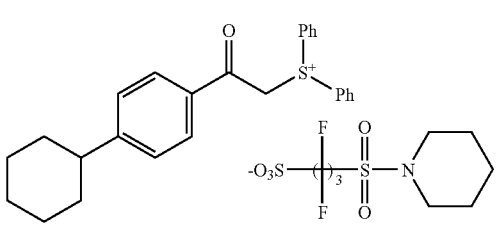
I-11
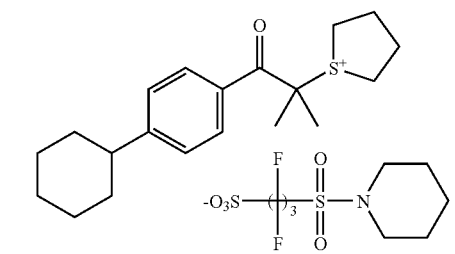
I-12
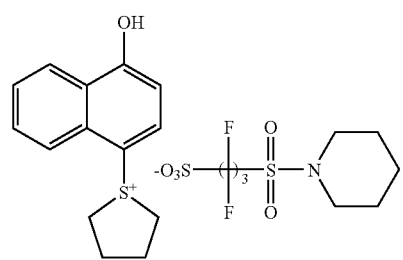
I-13
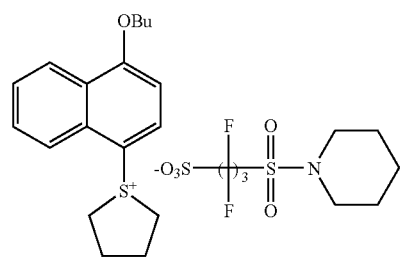
I-14
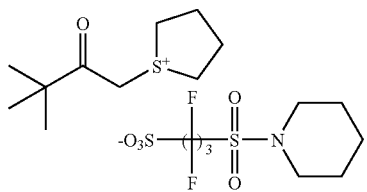
I-15
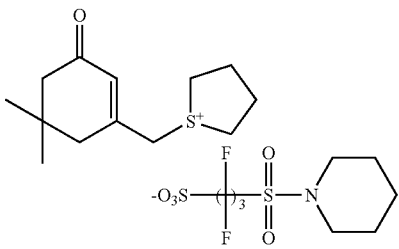
I-16
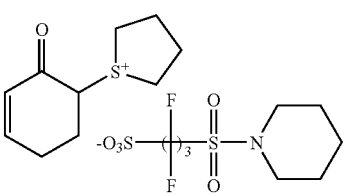
I-17
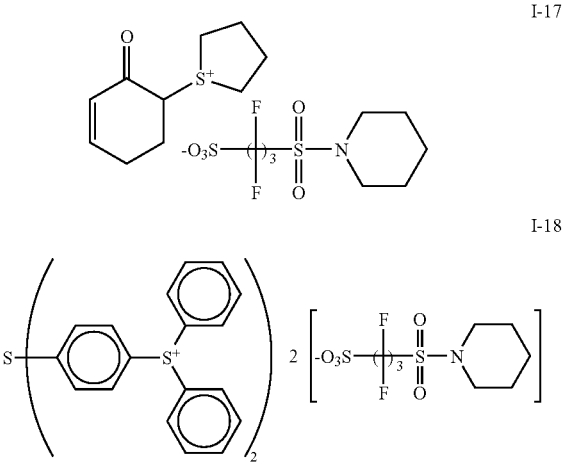
I-18
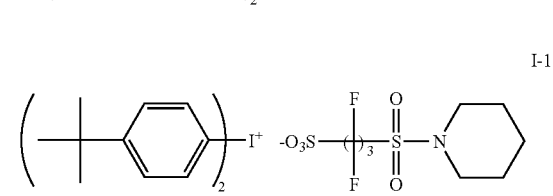
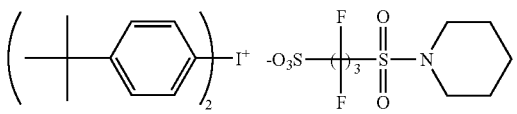
I-19
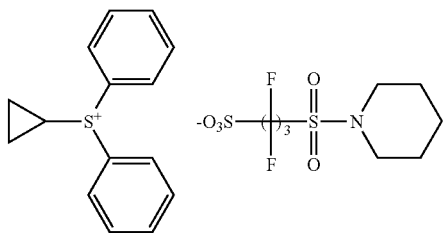
I-20
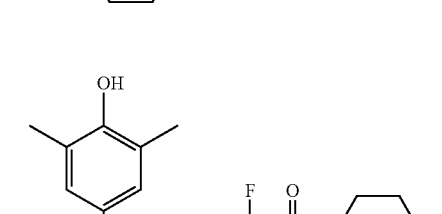
I-21
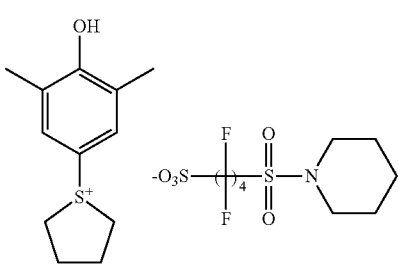
I-22
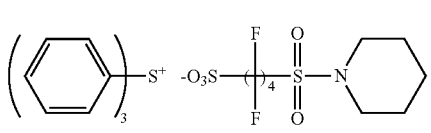

-continued
I-23
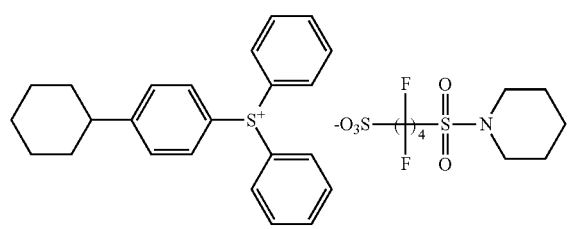
I-24
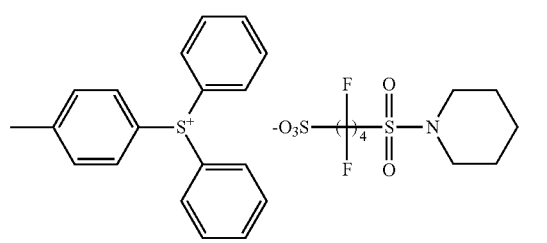
I-25
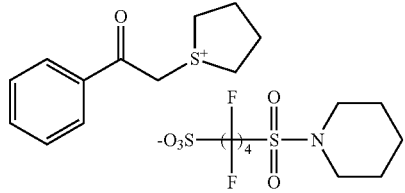
I-26
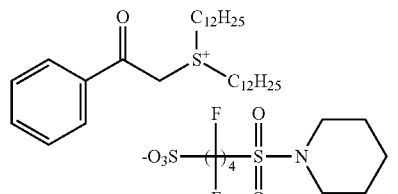
I-27
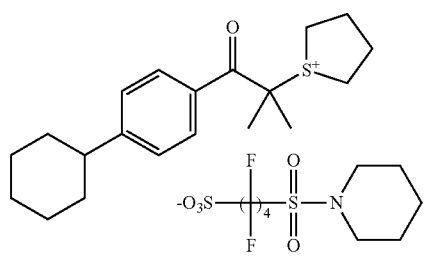
I-28
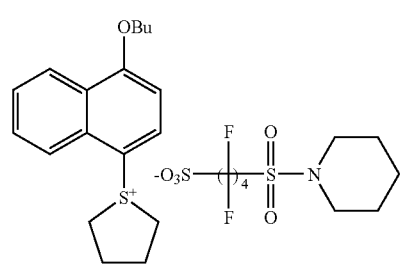
I-29
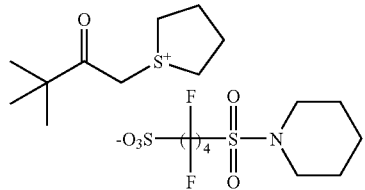
-continued
I-30
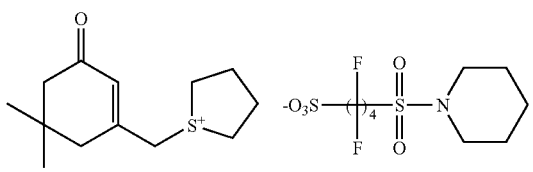
I-31
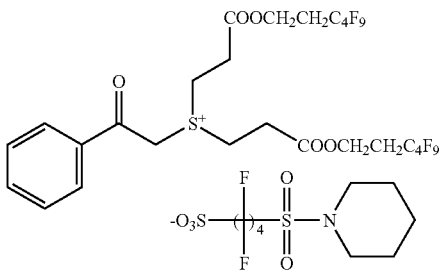
I-32
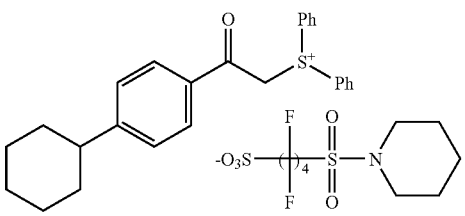
I-33
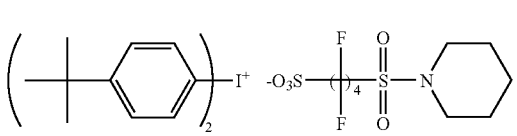
I-34
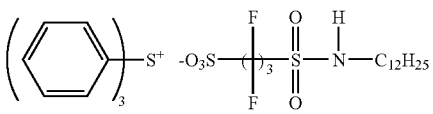
I-35
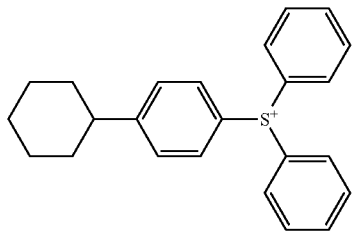
I-36
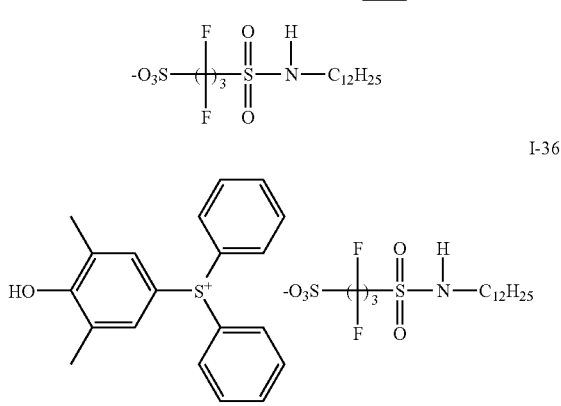

-continued
I-37
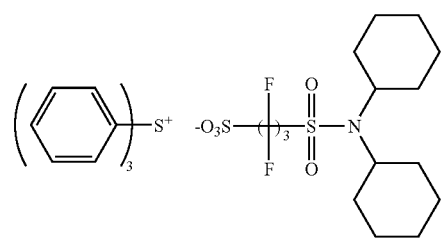
I-38
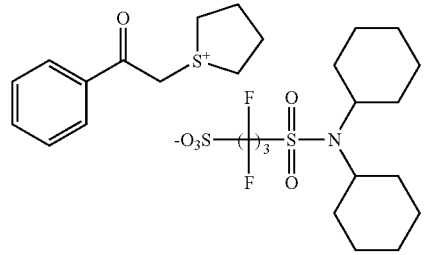
I-39
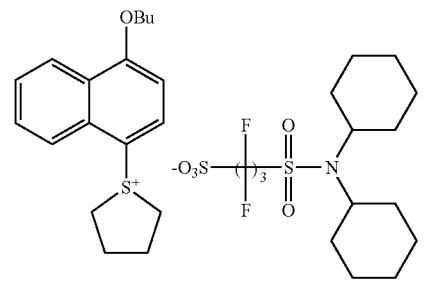
I-40
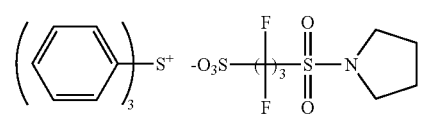
I-41
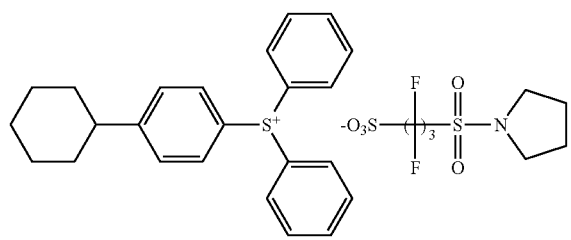
I-42
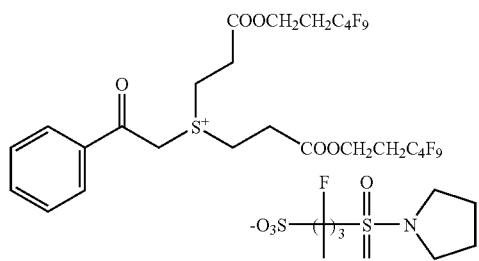
I-43
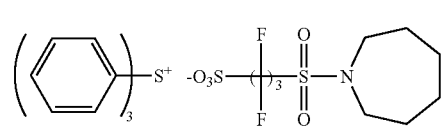
-continued
I-44
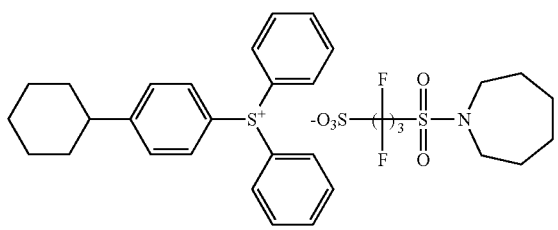
I-45
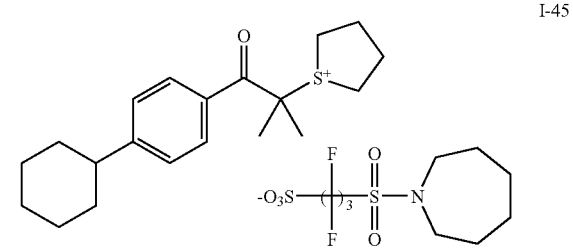
I-46
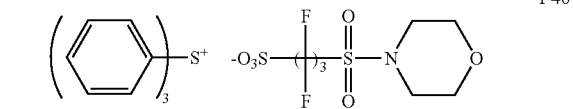
I-47
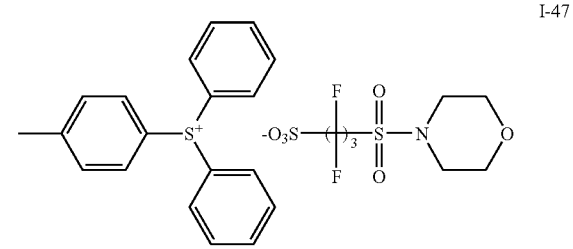
I-48
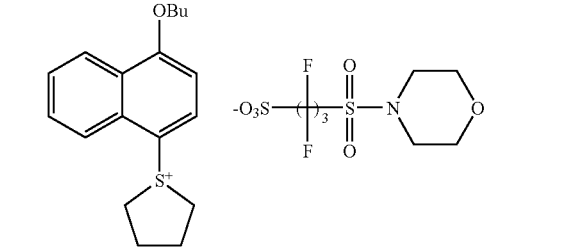
I-49
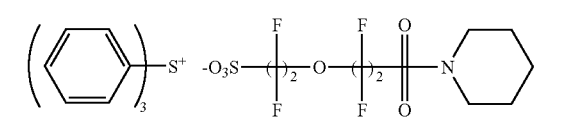
I-50
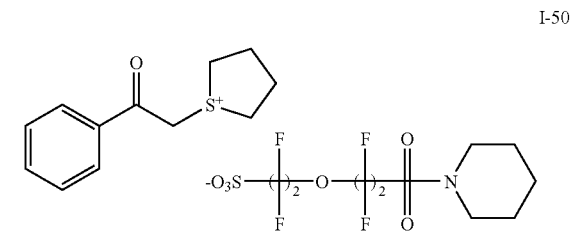

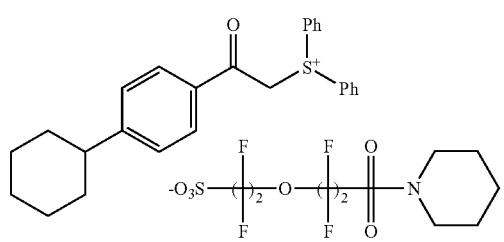
I-51
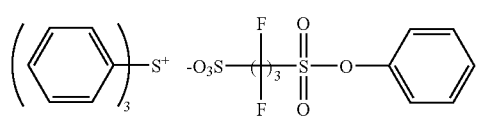
I-52
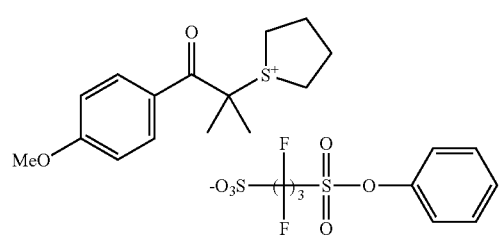
I-53
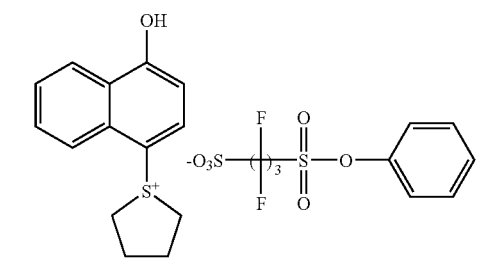
I-54
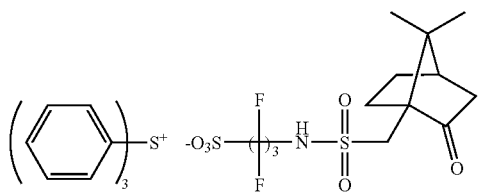
I-55
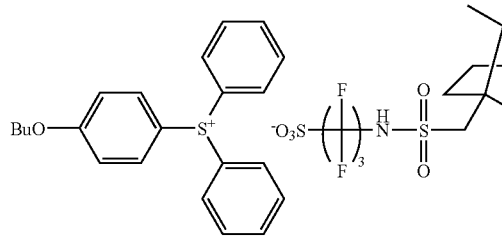
I-56
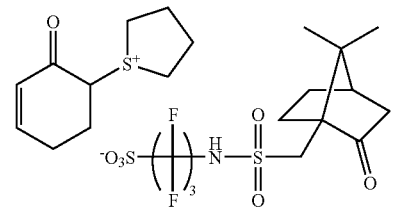
I-57
I-58
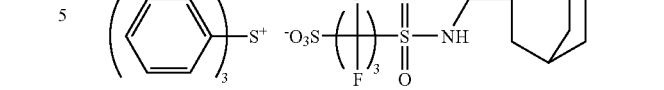
I-59
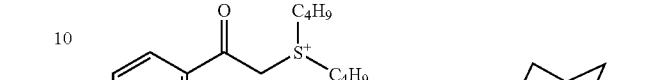
I-60
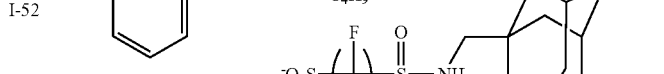
I-61
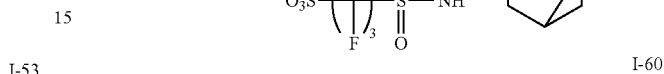
I-62
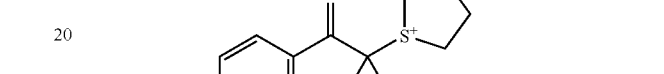
I-63
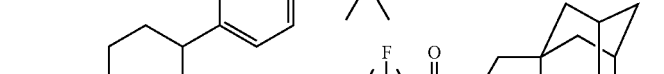
I-64
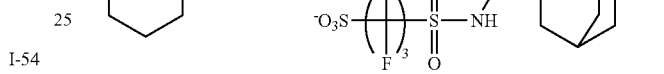
I-65

-continued
I-66
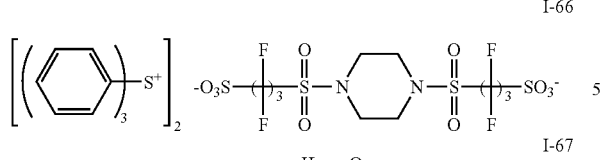
I-67
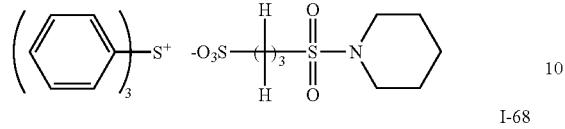
I-68
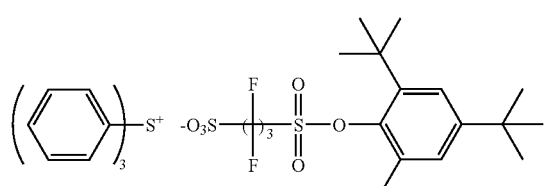
I-69
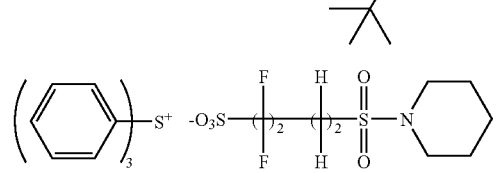
I-70
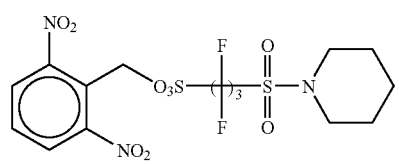
I-71
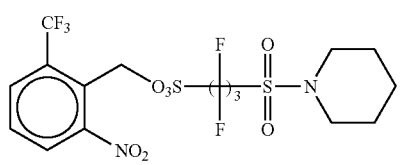
I-72
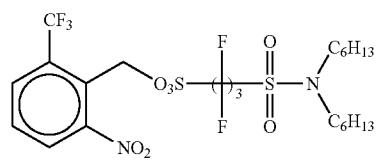
I-73
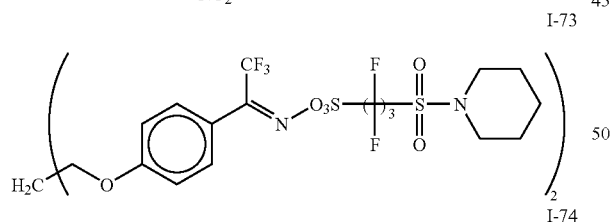
I-74
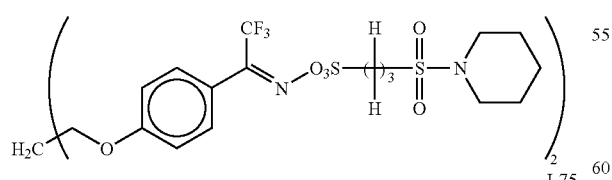
I-75
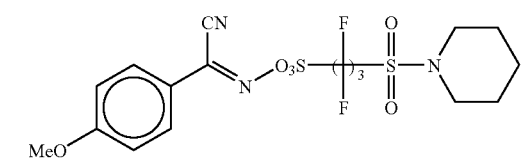
-continued
I-76
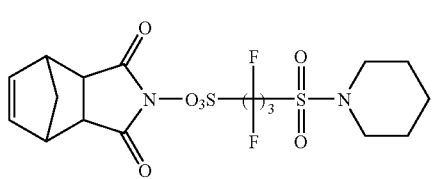
I-77
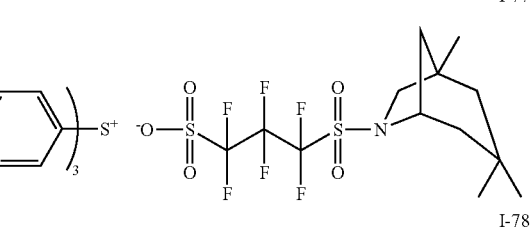
I-78
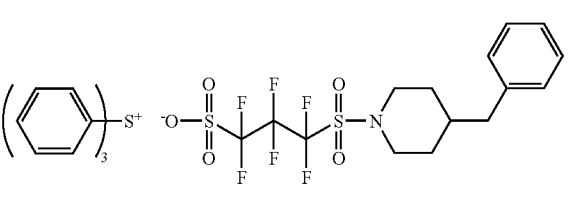
I-79
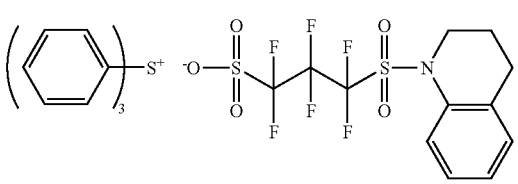
I-80
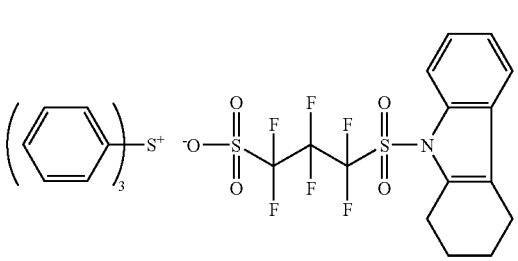
I-81
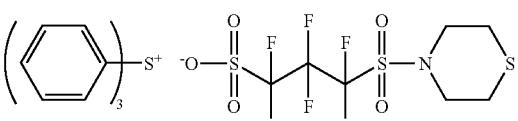
I-82
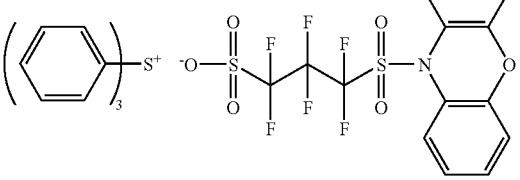
I-83
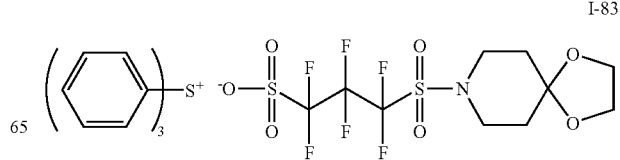

-continued

I-84
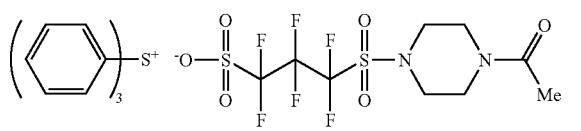

I-85

I-86
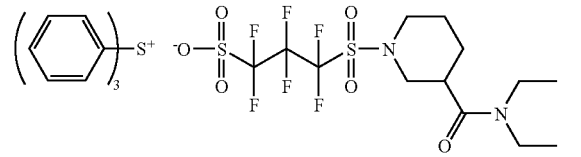

I-87
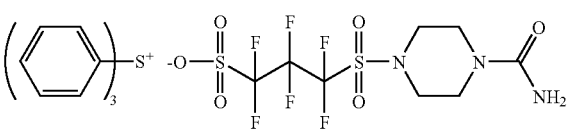

I-88
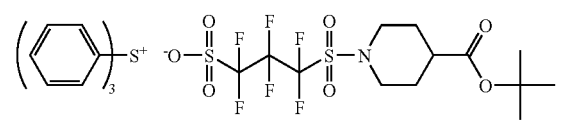

I-89
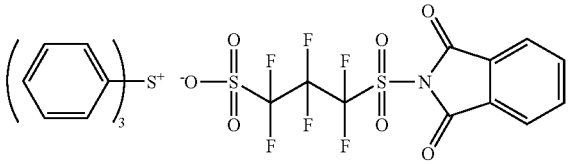

I-90
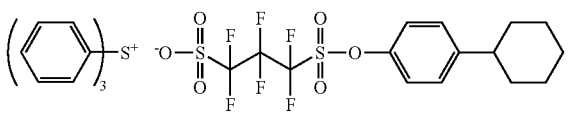

I-91
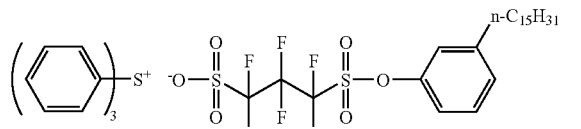

I-92
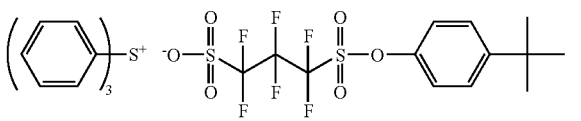

-continued

I-93
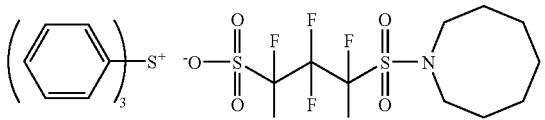

A sulfonic acid represented by general formula (I) or (I') or a salt thereof (e.g., an onium salt or metal salt) can be synthesized by a general sulfonic acid esterification reaction or sulfonamide-forming reaction. For example, the target compound can be obtained by a method in which a bissulfonyl halide compound is reacted in such a manner that one of the sulfonyl halide moieties is selectively reacted with an amine, alcohol, or amide compound or the like to form a sulfonamide bond, sulfonic ester bond, or sulfonimide bond and thereafter the other sulfonyl halide moiety is hydrolyzed. Alternatively, use can be made of a method in which a cyclic sulfonic anhydride is subjected to ring cleavage with an amine, alcohol, or amide compound to thereby obtain the target compound.

Examples of the salt of a sulfonic acid represented by general formula (I) or (I') include sulfonic acid metal salts and sulfonic acid onium salts. Examples of the metal in the sulfonic acid metal salts include $Na^+$, $Li^+$, and $K^+$. Examples of the onium cation in the sulfonic acid onium salts include ammonium cations, sulfonium cations, iodonium cations, phosphonium cations, and diazonium cations.

A sulfonic acid represented by general formula (I) or (I') or a salt thereof can be used for synthesizing the compound which generates a sulfonic acid represented by general formula (I) or (I') upon irradiation with an actinic ray or a radiation.

The compound which generates a sulfonic acid represented by general formula (I) or (I') upon irradiation with an actinic ray or a radiation can be synthesized by a method in which the sulfonic acid represented by general formula (I) or (I') is subjected to salt exchange with an optically active onium salt such as a sulfonium salt or iodonium salt. Alternatively, the target compound can be synthesized by forming an ester of the sulfonic acid represented by general formula (I) or (I') with nitrobenzyl alcohol, an N-hydroxyimide, or an oxime compound.

The content of the compound (A) in the photosensitive composition of the invention is preferably 0.1-20% by mass ("% by mass" means wt % in this specification), more preferably 0.5-10% by mass, even more preferably 1-7% by mass, based on all solid components of the composition.

(Optional Acid Generators)

In the invention, a compound which decomposes upon irradiation with an actinic ray or a radiation to generate an acid (acid generator) may be used besides the compound (A).

The amount of such a photo-acid generator which can be optionally used is generally from 100/0 to 20/80, preferably from 100/0 to 40/60, more preferably from 100/0 to 50/50, in terms of molar ratio (compound (A)/optional acid generator).

The acid generator to be optionally used can be suitably selected from photoinitiators for cationic photopolymerization, photoinitiators for radical photopolymerization, photodecolorants or optical color changers for dyes, known compounds used in microresist formation or the like which generate an acid upon irradiation with an actinic ray or a radiation, and mixtures of two or more thereof.

Examples thereof include diazonium salts, phosphonium salts, sulfonium salts, iodonium salts, imidesulfonates, oximesulfonates, diazodisulfones, disulfones, and o-nitrobenzyl sulfonates.

Also usable are compounds obtained by incorporating any of those groups or compounds which generate an acid upon irradiation with an actinic ray or a radiation into the main chain or side chains of a polymer. Examples thereof are given in, e.g., U.S. Pat. No. 3,849,137, German Patent 3,914,407, JP-A-63-26653, JP-A-55-164824, JP-A-62-69263, JP-A-63-146038, JP-A-63-163452, JP-A-62-153853, and JP-A-63-146029.

Furthermore, those compounds generating an acid by the action of light which are described in U.S. Pat. No. 3,779,778, European Patent 126,712, etc. can be used.

Preferred examples of the optionally usable compounds which decompose upon irradiation with an actinic ray or a radiation to generate an acid include compounds represented by the following general formulae (ZI), (ZII), and (ZIII).

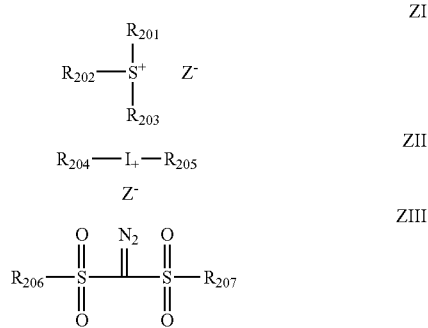

In general formula (ZI), $R_{201}$, $R_{202}$, and $R_{203}$ each independently represents an organic group.

The number of carbon atoms in each of the organic groups represented by $R_{201}$, $R_{202}$, and $R_{203}$ is generally 1 to 30, preferably 1 to 20.

Two of $R_{201}$ to $R_{203}$ may be bonded to each other to form a ring structure, which may contain an oxygen atom, sulfur atom, ester bond, amide bond, or carbonyl group therein.

Examples of the group formed by the bonding of two of $R_{201}$ to $R_{203}$ include alkylene groups (e.g., butylene and pentylene).

$Z^-$ represents a non-nucleophilic anion.

Examples of the non-nucleophilic anion represented by $Z^-$ include a sulfonic acid anion, carboxylic acid anion, sulfonylimide anion, bis(alkylsulfonyl)imide anion, and tris(alkylsulfonyl)methyl anion.

A non-nucleophilic anion is an anion the ability of which to cause a nucleophilic reaction is exceedingly low and which can be inhibited from being decomposed by an intramolecular nucleophilic reaction with the lapse of time. This anion improves the long-term stability of resists.

Examples of the sulfonic acid anion include alkylsulfonic acid anions, arylsulfonic acid anions, and camphorsulfonic acid anions.

Examples of the carboxylic acid anion include alkylcarboxylic acid anions, arylcarboxylic acid anions, and aralkylcarboxylic acid anions.

The alkyl moiety in each of the alkylsulfonic acid anions may be either an alkyl group or a cycloalkyl group. Preferred examples thereof include alkyl groups having 1-30 carbon atoms and cycloalkyl groups having 3-30 carbon atoms, such as methyl, ethyl, propyl, isopropyl, n-butyl, isobutyl, sec-butyl, pentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, cyclopentyl, cyclohexyl, adamantyl, norbornyl, and bornyl.

The aryl group in each of the arylsulfonic acid anions preferably is an aryl group having 6-14 carbon atoms. Examples thereof include phenyl, tolyl, and naphthyl.

Examples of substituents of the alkyl, cycloalkyl, and aryl groups in the alkylsulfonic acid anions and arylsulfonic acid anions include nitro, halogen atoms (fluorine, chlorine, bromine, and iodine atoms), carboxyl, hydroxy, amino, cyano, alkoxy groups (preferably having 1-5 carbon atoms), cycloalkyl groups (preferably having 3-15 carbon atoms), aryl groups (preferably having 6-14 carbon atoms), alkoxycarbonyl groups (preferably having 2-7 carbon atoms), acryl groups (preferably having 2-12 carbon atoms), and alkoxycarbonyloxy groups (preferably having 2-7 carbon atoms). With respect to the aryl groups and ring structures possessed by these groups, examples of the substituents further include alkyl groups (preferably having 1-15 carbon atoms).

Examples of the alkyl moiety in each of the alkylcarboxylic acid anions include the same alkyl groups and cycloalkyl groups as in the alkylsulfonic acid anions.

Examples of the aryl group in each of the arylcarboxylic acid anions include the same aryl groups as in the arylsulfonic acid anions.

Examples of the aralkyl group in each of the aralkylcarboxylic acid anions include aralkyl groups preferably having 6-12 carbon atoms, such as benzyl, phenethyl, naphthylmethyl, naphthylethyl and naphthylbutyl.

Examples of substituents of the alkyl, cycloalkyl, aryl, and aralkyl groups in the alkylcarboxylic acid anions, arylcarboxylic acid anions, and aralkylcarboxylic acid anions include the same halogen atoms and the same alkyl, cycloalkyl, alkoxy, and alkylthio groups as in the arylsulfonic acid anions.

Examples of the sulfonylimide anion include a saccharin anion.

The alkyl groups in the bis(alkylsulfonyl)imide anion and tris(alkylsulfonyl)methyl anion preferably are alkyl groups having 1-5 carbon atoms. Examples thereof include methyl, ethyl, propyl, isopropyl, n-butyl, isobutyl, sec-butyl, pentyl, and neopentyl. Examples of substituents of these alkyl groups include halogen atoms, alkyl groups substituted by one or more halogen atoms, alkoxy groups, and alkylthio groups. Preferred are alkyl groups substituted by one or more fluorine atoms.

Other examples of the non-nucleophilic anion include phosphorus fluoride, boron fluoride, and antimony fluoride.

The non-nucleophilic anion represented by $Z^-$ preferably is an alkanesulfonic acid anion in which the sulfonic acid has been substituted in the α-position by one or more fluorine atoms, an arylsulfonic acid anion substituted by one or more fluorine atoms or fluorinated groups, a bis(alkylsulfonyl)methide anion in which the alkyl groups have been substituted by one or more fluorine atoms, or a tris(alkylsulfonyl)imide anion in which the alkyl groups have been substituted by one or more fluorine atoms. The non-nucleophilic anion especially preferably is a perfluoroalkanesulfonic acid anion having 4-8 carbon atoms or a benzenesulfonic acid anion having one or more fluorine atoms. Most preferred is a nonafluorobutanesulfonic acid anion, perfluorooctanesulfonic acid anion, pentafluorobenzenesulfonic acid anion, or 3,5-bis(trifluoromethyl)benzenesulfonic acid anion.

Examples of the organic groups represented by $R_{201}$, $R_{202}$, and $R_{203}$ include the corresponding groups in the compounds (Z1-1), (Z1-2), and (Z1-3) which will be described later.

A compound having two or more structures represented by general formula (ZI) may also be used. For example, use may be made of a compound having a structure in which at least one of the $R_{201}$ to $R_{203}$ of a compound represented by general formula (ZI) is bonded to at least one of the $R_{201}$ to $R_{203}$ of another compound represented by general formula (ZI).

More preferred examples of the ingredient (ZI) include the compounds (Z1-1), (Z1-2), and (Z1-3) which will be explained below.

Compound (Z1-1) is an arylsulfonium compound represented by general formula (ZI) wherein at least one of $R_{201}$ to $R_{203}$ is an aryl group, i.e., a compound including an arylsulfonium as a cation.

The arylsulfonium compound may be one in which all of $R_{201}$ to $R_{203}$ are aryl groups, or may be one in which part of $R_{201}$ to $R_{203}$ is an aryl group and the remainder is an alkyl or cycloalkyl group.

Examples of the arylsulfonium compound include triarylsulfonium compounds, diarylalkylsulfonium compounds, and aryldialkylsulfonium compounds.

The aryl group of the arylsulfonium compound preferably is phenyl or naphthyl, and more preferably is phenyl. In the case where the arylsulfonium compound has two or more aryl groups, these aryl groups may be the same or different.

The alkyl group or cycloalkyl group which is optionally possessed by the arylsulfonium compound preferably is a linear or branched alkyl group having 1-15 carbon atoms or a cycloalkyl group having 3-15 carbon atoms. Examples thereof include methyl, ethyl, propyl, n-butyl, sec-butyl, t-butyl, cyclopropyl, cyclobutyl, and cyclohexyl.

The aryl, alkyl, and cycloalkyl groups represented by $R_{201}$ to $R_{203}$ may have substituents selected from alkyl groups (e.g., ones having 1-15 carbon atoms), cycloalkyl groups (e.g., ones having 3-15 carbon atoms), aryl groups (e.g., ones having 6-14 carbon atoms), alkoxy groups (e.g., ones having 1-15 carbon atoms), halogen atoms, hydroxy, and phenylthio. Preferred examples of the substituents are linear or branched alkyl groups having 1-12 carbon atoms, cycloalkyl groups having 3-12 carbon atoms, and linear, branched, or cyclic alkoxy groups having 1-12 carbon atoms. Most preferred are alkyl groups having 1-4 carbon atoms and alkoxy groups having 1-4 carbon atoms. Any one of $R_{201}$ to $R_{203}$ may have such a substituent or each of $R_{201}$ to $R_{203}$ may have such a substituent. In the case where $R_{201}$ to $R_{203}$ are aryl groups, it is preferred that a substituent be bonded to the p-position in each aryl group.

Next, compound (Z1-2) will be explained.

Compound (Z1-2) is a compound represented by formula (ZI) wherein $R_{201}$ to $R_{203}$ each independently represents an organic group containing no aromatic ring. The term aromatic ring herein implies any of aromatic rings including ones containing one or more heteroatoms.

The organic groups containing no aromatic ring which are represented by $R_{201}$ to $R_{203}$ each have generally 1-30, preferably 1-20 carbon atoms.

Preferably, $R_{201}$ to $R_{203}$ each independently are an alkyl, cycloalkyl, allyl, or vinyl group. $R_{201}$ to $R_{203}$ each more preferably are a linear or branched 2-oxoalkyl, 2-oxocycloalkyl, or alkoxycarbonylmethyl group, and most preferably are a linear or branched 2-oxoalkyl group.

Preferred examples of the alkyl groups and cycloalkyl groups represented by $R_{201}$ to $R_{203}$ include linear or branched alkyl groups having 1-10 carbon atoms (e.g., methyl, ethyl, propyl, butyl, and pentyl) and cycloalkyl groups having 3-10 carbon atoms (e.g., cyclopentyl, cyclohexyl, and norbornyl). More preferred examples of the alkyl groups include 2-oxoalkyl groups and alkoxycarbonylmethyl groups. More preferred examples of the cycloalkyl groups include 2-oxocycloalkyl groups.

The 2-oxoalkyl groups may be either linear or branched. Preferred examples thereof include the alkyl groups enumerated above which each have $>C=O$ in the 2-position.

Preferred examples of the 2-oxocycloalkyl groups include the cycloalkyl groups enumerated above which each have $>C=O$ in the 2-position.

Examples of the alkyl groups in the alkoxycarbonylmethyl groups include alkyl groups preferably having 1-5 carbon atoms (methyl, ethyl, propyl, butyl, and pentyl).

$R_{201}$ to $R_{203}$ may have been further substituted by substituents selected from halogen atoms, alkoxy groups (e.g., ones having 1-5 carbon atoms), hydroxy, cyano, and nitro.

Two of $R_{201}$ to $R_{203}$ may be bonded to each other to form a ring structure, which may contain an oxygen atom, sulfur atom, ester bond, amide bond, or carbonyl group therein. Examples of the group formed by the bonding of two of $R_{201}$ to $R_{203}$ include alkylene groups (e.g., butylene and pentylene).

Compound (Z1-3) is a compound represented by the following general formula (Z1-3). Namely, it is a compound having a phenacylsulfonium salt structure.

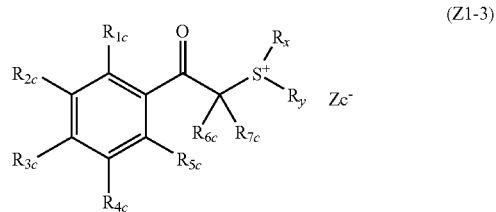

(Z1-3)

$R_{1C}$ to $R_{5C}$ each independently represents a hydrogen atom, alkyl, cycloalkyl, or alkoxy group, or halogen atom.

$R_{6C}$ and $R_{7C}$ each represent a hydrogen atom or an alkyl or cycloalkyl group.

$R_x$ and $R_y$ each independently represents an alkyl, cycloalkyl, allyl, or vinyl group.

Two or more of $R_{1C}$ to $R_{5C}$ may be bonded to each other to form a ring structure, and $R_x$ and $R_y$ may be bonded to each other to form a ring structure. These ring structures may contain an oxygen atom, sulfur atom, ester bond, or amide bond.

$Zc^-$ represents a non-nucleophilic anion. Examples thereof include the same non-nucleophilic anions as those enumerated above as examples of $X^-$ in general formula (ZI).

The alkyl groups represented by $R_{1C}$ to $R_{5C}$ may be either linear or branched. Examples thereof include alkyl groups having 1-20 carbon atoms, preferably, linear or branched alkyl groups having 1-12 carbon atoms (e.g., methyl, ethyl, linear or branched propyl, linear or branched butyl, and linear or branched pentyl). Examples of the cycloalkyl groups include cycloalkyl groups having 3-8 carbon atoms (e.g., cyclopentyl and cyclohexyl).

The alkoxy groups represented by $R_{1C}$ to $R_{5C}$ may be either linear or branched or cyclic. Examples thereof include alkoxy groups having 1-10 carbon atoms. Preferred examples thereof include linear or branched alkoxy groups having 1-5 carbon atoms (e.g., methoxy, ethoxy, linear or branched propoxy, linear or branched butoxy, and linear or branched pentoxy) and cyclic alkoxy groups having 3-8 carbon atoms (e.g., cyclopentyloxy and cyclohexyloxy).

It is preferred that any of $R_{1C}$ to $R_{5C}$ be a linear or branched alkyl group, cycloalkyl group, or linear, branched, or cyclic alkoxy group. It is more preferred that the total number of carbon atoms in $R_{1C}$ to $R_{5C}$ be from 2 to 15. This compound has further improved solubility in solvents and is inhibited from generating particles during storage.

Examples of the alkyl groups and cycloalkyl groups represented by $R_x$ and $R_y$ include the same alkyl groups and cycloalkyl groups as those enumerated above as examples of $R_{1C}$ to $R_{5C}$. More preferred are 2-oxoalkyl groups, 2-oxocycloalkyl groups, and alkoxycarbonylmethyl groups.

Examples of the 2-oxoalkyl groups and 2-oxocycloalkyl groups include those alkyl and cycloalkyl groups represented by $R_{1C}$ to $R_{5C}$ which each have >C=O in the 2-position.

Examples of the alkoxy groups in the alkoxycarbonylmethyl groups include the same alkoxy groups as those enumerated above as examples of $R_{1C}$ to $R_{5C}$.

Examples of the group formed by the bonding of $R_x$ and $R_y$ include butylene and pentylene.

$R_x$ and $R_y$ each preferably are an alkyl or cycloalkyl group having 4 or more carbon atoms, and more preferably are an alkyl or cycloalkyl group having 6 or more, especially 8 or more carbon atoms.

In general formulae (ZII) and (ZIII), $R_{204}$ to $R_{207}$ each independently represents an aryl, alkyl, or cycloalkyl group.

The aryl groups represented by $R_{204}$ to $R_{207}$ preferably are phenyl or naphthyl, and more preferably are phenyl.

Preferred examples of the alkyl groups and cycloalkyl groups represented by $R_{204}$ to $R_{207}$ include linear or branched alkyl groups having 1-10 carbon atoms (e.g., methyl, ethyl, propyl, butyl, and pentyl) and cycloalkyl groups having 3-10 carbon atom (e.g., cyclopentyl, cyclohexyl, and norbornyl).

Examples of substituents which may be possessed by $R_{204}$ to $R_{207}$ include alkyl groups (e.g., ones having 1-15 carbon atoms), cycloalkyl groups (e.g., ones having 3-15 carbon atoms), aryl groups (e.g., ones having 6-15 carbon atoms), alkoxy groups (e.g., ones having 1-15 carbon atoms), halogen atoms, hydroxy, and phenylthio.

$Z^-$ represents a non-nucleophilic anion, and examples thereof include the same non-nucleophilic anions as those enumerated above as examples of $Z^-$ in general formula (ZI).

Other preferred examples of the optionally usable compounds which decompose upon irradiation with an actinic ray or a radiation to generate an acid include compounds represented by the following general formulae (ZIV), (ZV), and (ZVI).

$$Ar_3-SO_2-SO_2-Ar_4 \quad \text{ZIV}$$

<center>ZV</center>

<center>ZVI</center>

In general formulae (ZIV) to (ZVI), $Ar_3$ and $Ar_4$ each independently represents an aryl group.

$R_{206}$, $R_{207}$, and $R_{208}$ each represent an alkyl, cycloalkyl, or aryl group.

Symbol A represents an alkylene, alkenylene, or arylene group.

Even more preferred of the optionally usable compounds which decompose upon irradiation with an actinic ray or a radiation to generate an acid are the compounds represented by general formulae (ZI) to (ZIII).

Preferred optionally usable compounds which decompose upon irradiation with an actinic ray or a radiation to generate an acid are compounds which generate a sulfonic acid having one sulfo group. More preferred are compounds which generate a monobasic perfluoroalkanesulfonic acid and compounds which generate an aromatic sulfonic acid substituted by one or more fluorine atoms or fluorinated groups. Especially preferred are sulfonium salts of monobasic perfluoroalkanesulfonic acids.

Especially preferred examples of the optionally usable compounds which decompose upon irradiation with an actinic ray or a radiation to generate an acid are shown below.

(z1) triphenylsulfonium $CF_3SO_3^-$ (z2) triphenylsulfonium $C_4F_9SO_3^-$ (z3) triphenylsulfonium $C_8F_{17}SO_3^-$ (z4) triphenylsulfonium 2,4,6-triisopropylbenzenesulfonate -continued
(z5) 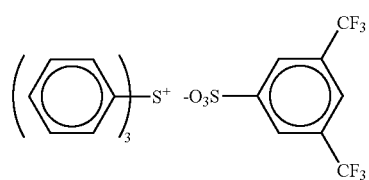
(z6) 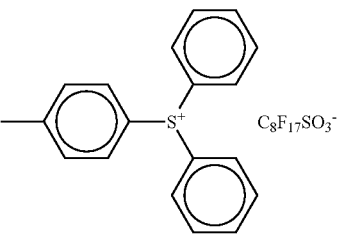
(z7) 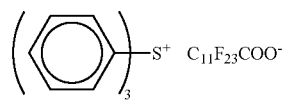
(z8) 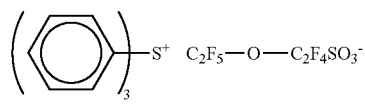
(z9) 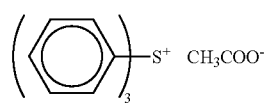
(z10) 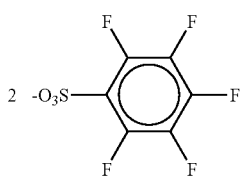
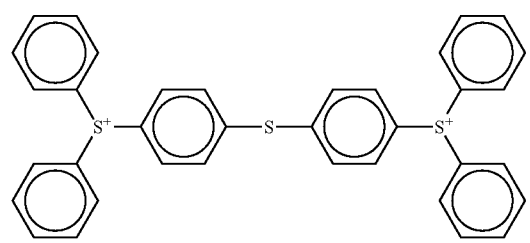
(z11) 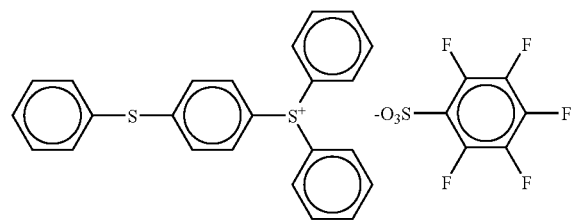
(z12) 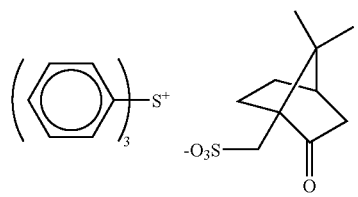
(z13) 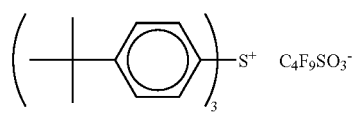
(z14) 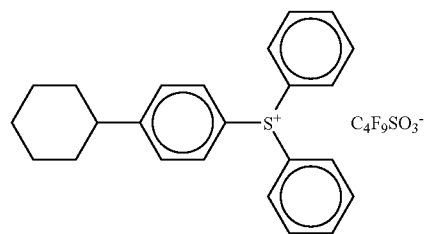
(z15) 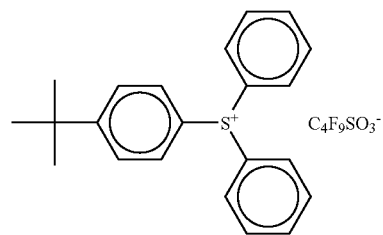
(z16) 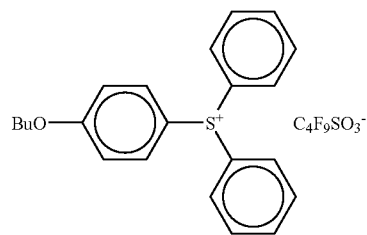
(z17) 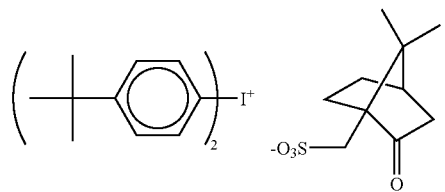
(z18)

-continued
(z19) 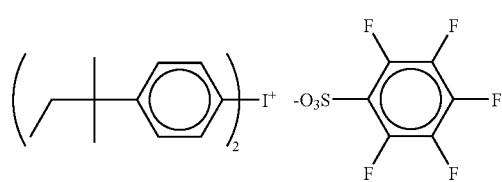
(z20) 
(z21) 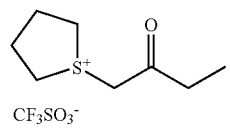
CF$_3$SO$_3^-$
(z22) 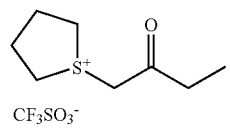
C$_4$F$_9$SO$_3^-$
(z23) 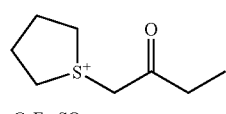
C$_8$F$_{17}$SO$_3^-$
(z24) 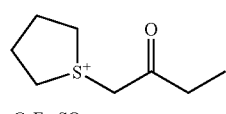
CF$_3$SO$_3^-$
(z25) 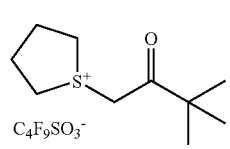
C$_4$F$_9$SO$_3^-$
(z26) 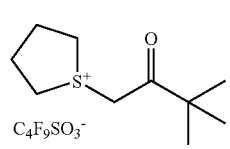
C$_8$F$_{17}$SO$_3^-$
(z27) 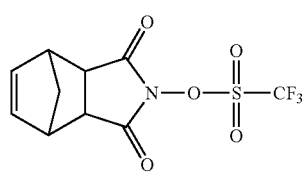
(z28) 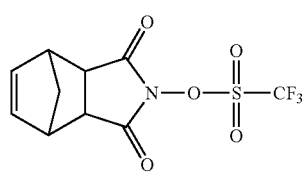
(z29) 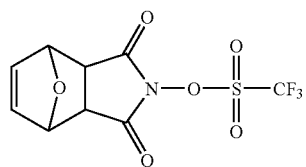
(z30) 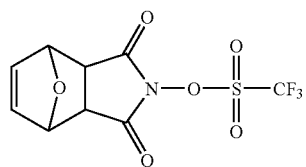
(z31) 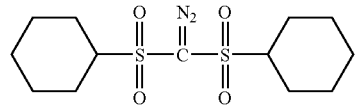
(z32) 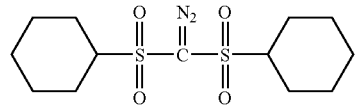
(z33) 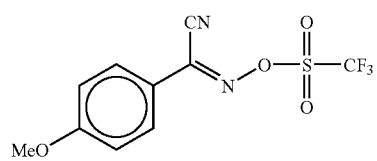
(z34) 
(z35) 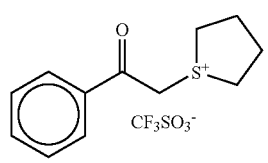
CF$_3$SO$_3^-$
(z36) 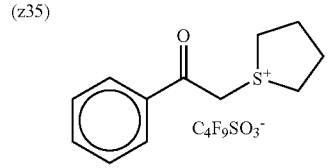
C$_4$F$_9$SO$_3^-$ -continued
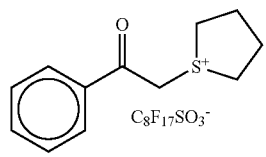
(z37)
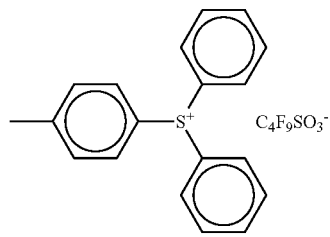
(z38)
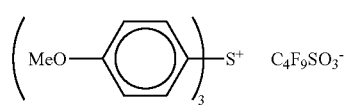
(z39)
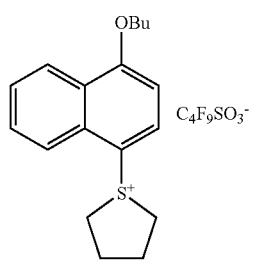
(z40)
(z41)
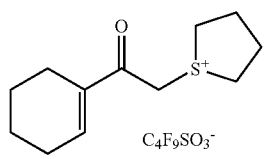
(z42)
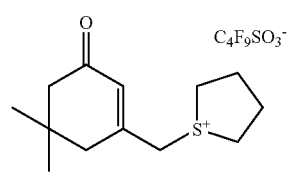
(z43)
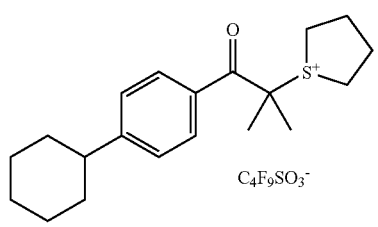
(z44)
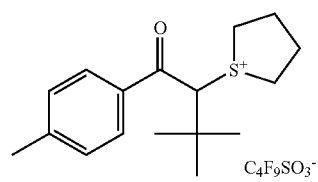
(z45)
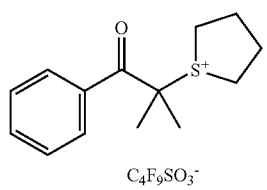
(z46)
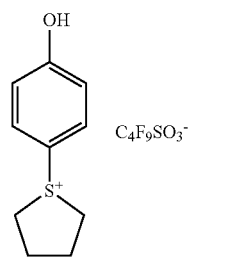
(z47)
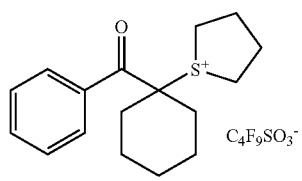
(z48)
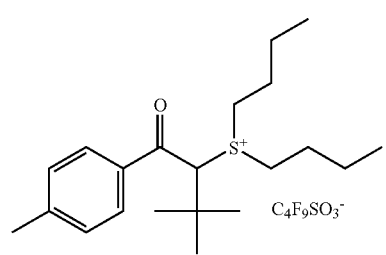
(z49)
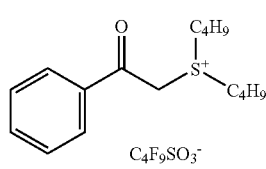
(z50)

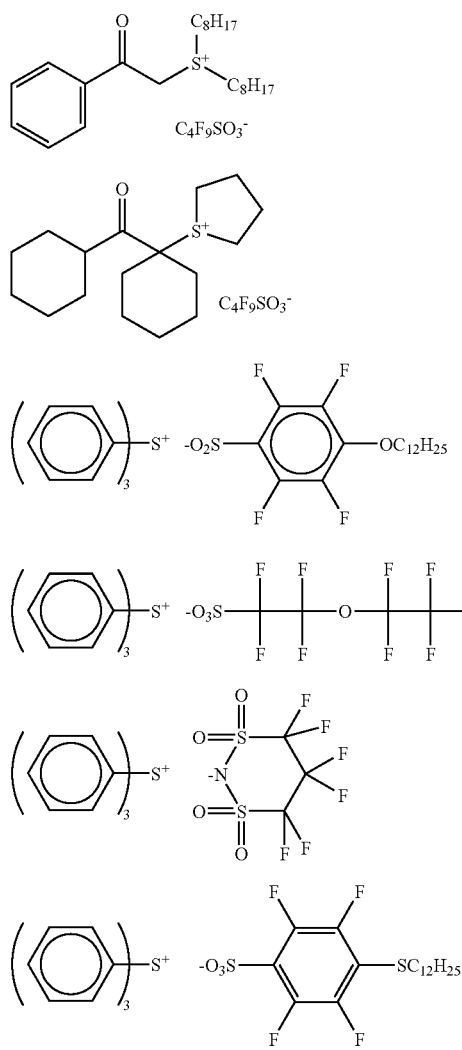
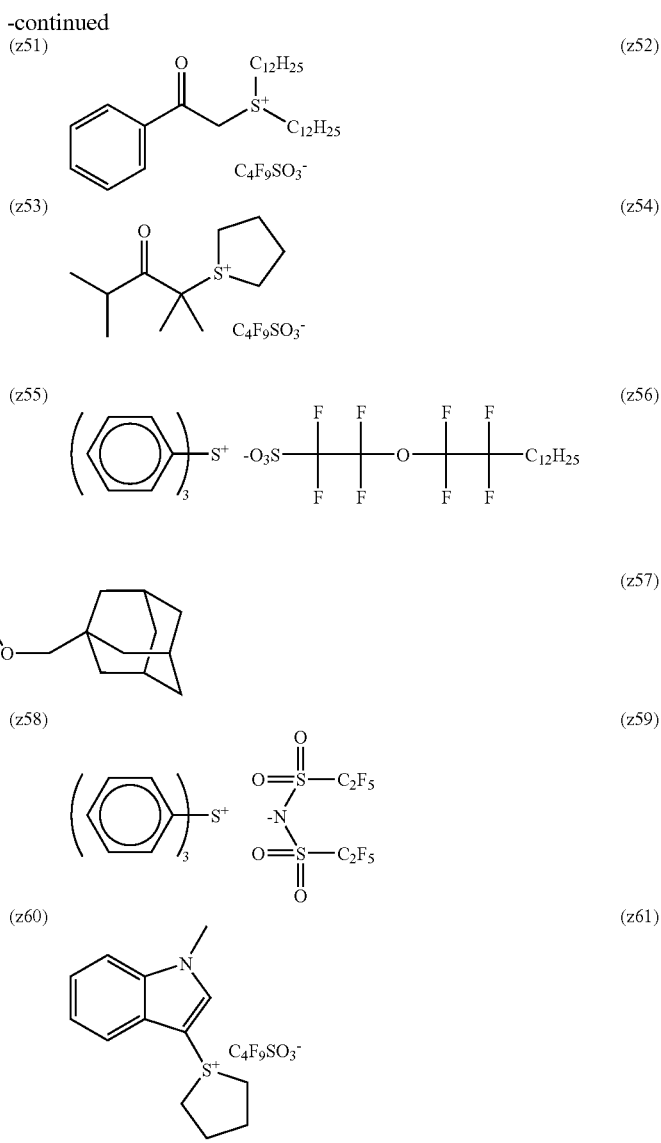

[2] (B) Resin Decomposing by Action of Acid to Increase its Solubility in Alkaline Developer (Hereinafter Referred to Also as "Ingredient (B)")

The resin which decomposes by the action of an acid to increase a solubility of the resin in an alkaline developer and is to be used in the positive type photosensitive composition of the invention is a resin which has groups dissociable with an acid (hereinafter referred to also as "acid-dissociable groups") in the main chain or side chains thereof or in both the main chain or side chains thereof. Preferred of such resins are ones which have acid-dissociable groups in side chains thereof.

Preferred acid-dissociable groups are groups formed by replacing the hydrogen atom of a —COOH or —OH group by a group eliminable with an acid.

The acid-dissociable groups in the invention are acetal groups or tertiary ester groups.

In the case of a resin having such acid-dissociable groups bonded as side chains, the base resin is an alkali-soluble resin having —OH or —COOH groups in side chains. Examples thereof include the alkali-soluble resins which will be described later.

The rate of alkali dissolution of these alkali-soluble resins is preferably 170 A/sec or higher, especially preferably 330 A/sec or higher (A is angstrom), as measured in 0.261-N tetramethylammonium hydroxide (TMAH) (23° C.).

From that standpoint, especially preferred alkali-soluble resins are alkali-soluble resins having structural hydroxystyrene units, such as poly(o-, m-, or p-hydroxystyrene), copolymers thereof, hydrogenated poly(hydroxystyrene), halogen- or alkyl-substituted poly(hydroxystyrene), partly O-alkylated or O-acylated poly(hydroxystyrene), styrene/hydroxystyrene copolymers, α-methylstyrene/hydroxystyrene copolymers, and hydrogenated novolak resins.

Preferred examples of repeating units having an acid-dissociable group in the invention include units derived from t-butoxycarbonyloxystyrene, 1-alkoxyethoxystyrenes, and tertiary alkyl esters of (meth)acrylic acid. More preferred are units derived from 2-alkyl-2-adamantyl (meth)acrylates and dialkyl(1-adamantyl)methyl (meth)acrylates.

Ingredient (B) to be used in the invention can be obtained by reacting an alkali-soluble resin with a precursor for an acid-dissociable group or by copolymerizing an alkalisoluble-resin monomer having an acid-dissociable group bonded thereto with various monomers, as disclosed in, e.g., European Patent 254,853, JP-A-2-25850, JP-A-3-223860, and JP-A-4-251259.

Specific examples of ingredient (B) to be used in the invention are shown below, but the ingredient in the invention should not be construed as being limited to these examples: p-t-butoxystyrene/p-hydroxystyrene copolymers, p-(t-butoxycarbonyloxy)styrene/p-hydroxystyrene copolymers, p-(t-butoxycarbonylmethyloxy)styrene/p-hydroxystyrene copolymers, 4-(t-butoxycarbonylmethyloxy)-3-methylstyrene/4-hydroxy-3-methylstyrene copolymers, p-(t-butoxycarbonylmethyloxy)styrene/p-hydroxystyrene (10% hydrogenated) copolymers, m-(t-butoxycarbonylmethyloxy)styrene/m-hydroxystyrene copolymers, o-(t-butoxycarbonylmethyloxy)styrene/o-hydroxystyrene copolymers, p-(cumyloxycarbonylmethyloxy)styrene/p-hydroxystyrene copolymers, cumyl methacrylate/methyl methacrylate copolymers, 4-t-butoxycarbonylstyrene/dimethyl maleate copolymers, benzyl methacrylate/tetrahydropyranyl methacrylate copolymers, p-(t-butoxycarbonylmethyloxy)styrene/p-hydroxystyrene/styrene copolymers, p-t-butoxystyrene/p-hydroxystyrene/fumaronitrile copolymers, t-butoxystyrene/hydroxyethyl methacrylate copolymers, styrene/N-(4-hydroxyphenyl)maleimide/N-(4-t-butoxycarbonyloxyphenyl)maleimide copolymers, p-hydroxystyrene/t-butyl methacrylate copolymers, styrene/p-hydroxystyrene/t-butyl methacrylate copolymers, p-hydroxystyrene/t-butyl acrylate copolymers, styrene/p-hydroxystyrene/t-butyl acrylate copolymers, p-(t-butoxycarbonylmethyloxy)styrene/p-hydroxystyrene/N-methylmaleimide copolymers, t-butyl methacrylate/1-adamantylmethyl methacrylate copolymers, p-hydroxystyrene/t-butyl acrylate/p-acetoxystyrene copolymers, p-hydroxystyrene/t-butyl acrylate/p-(t-butoxycarbonyloxy)styrene copolymers, p-hydroxystyrene/t-butyl acrylate/p-(t-butoxycarbonylmethyloxy)styrene copolymers, and the following copolymers.

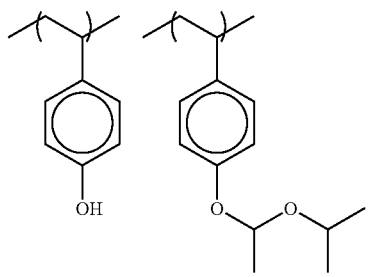

(R-1)

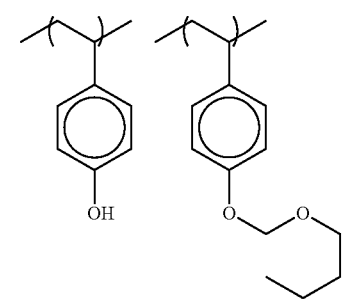

(R-2)

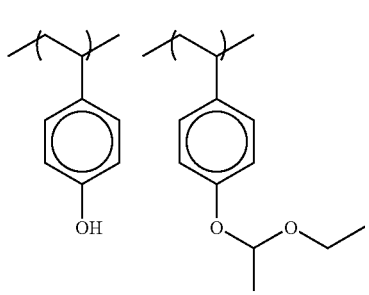

-continued

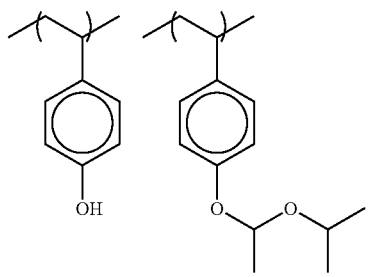

(R-3)

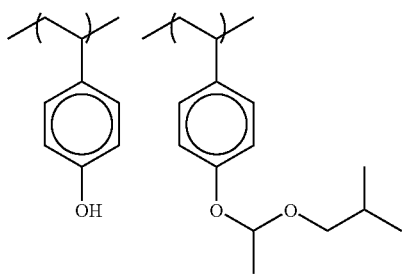

(R-4)

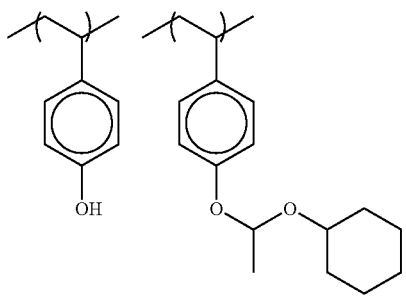

(R-5)

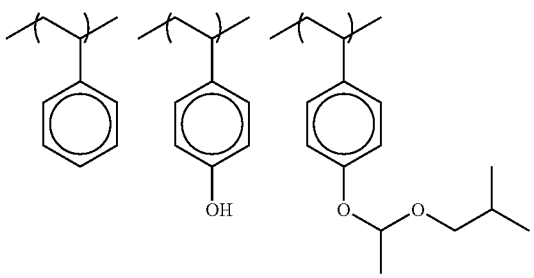

(R-6)

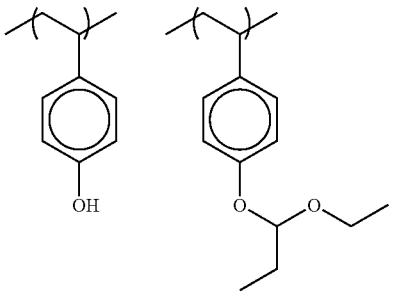

(R-7)

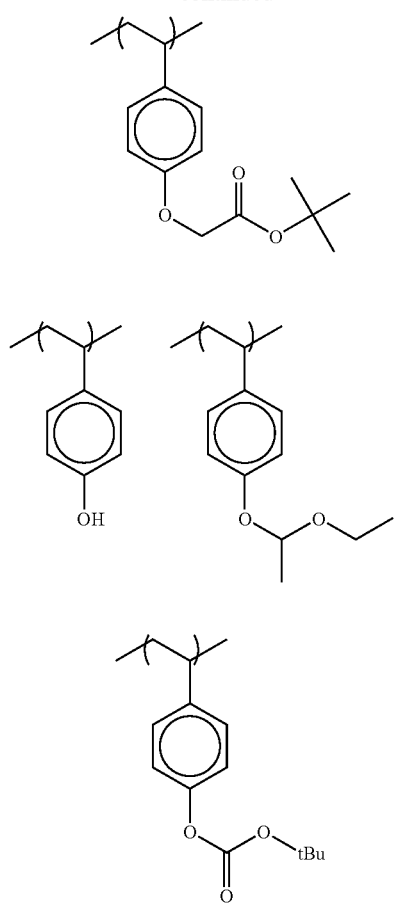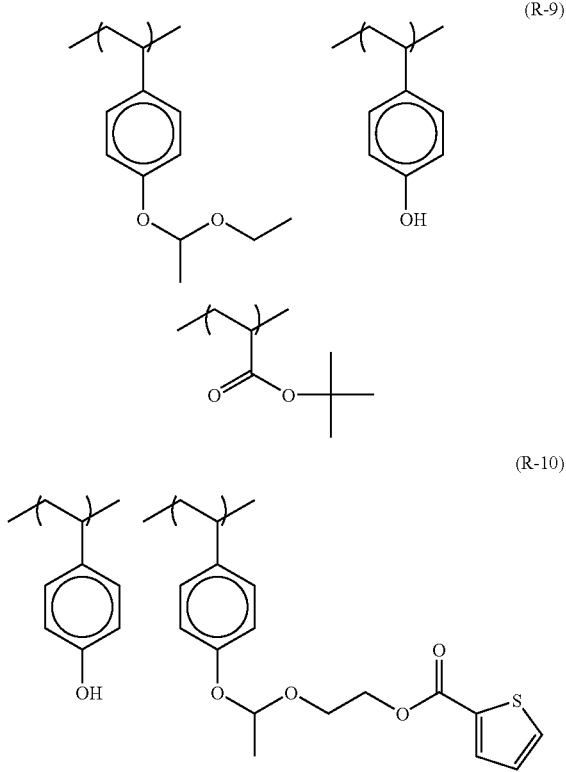

(R-14)
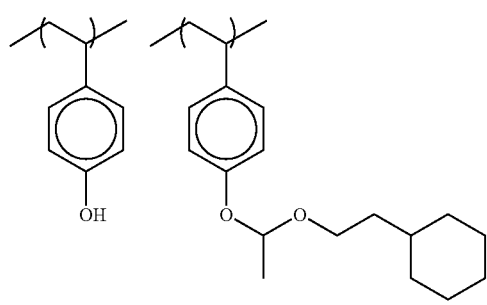
(R-15)
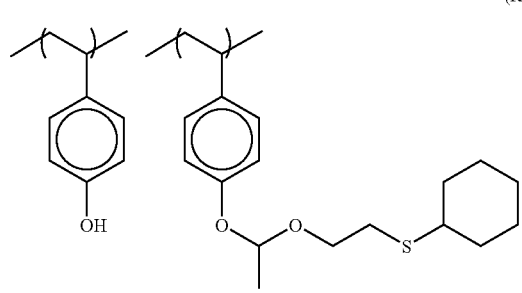
(R-16)
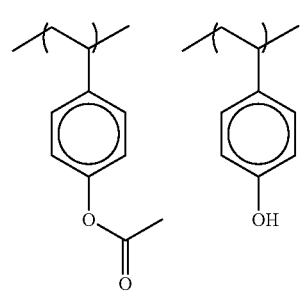
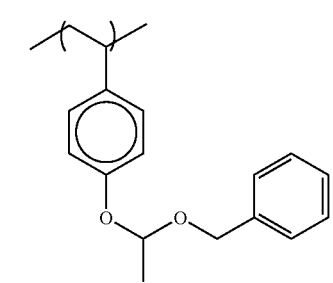
(R-17)
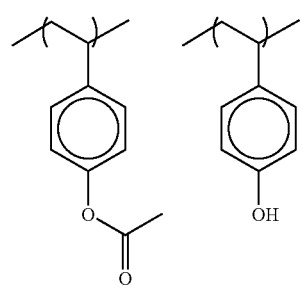
(R-18)
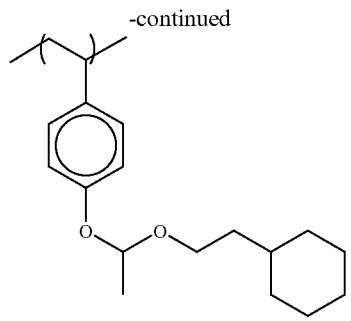
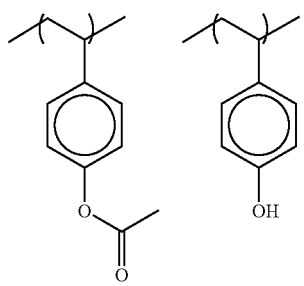
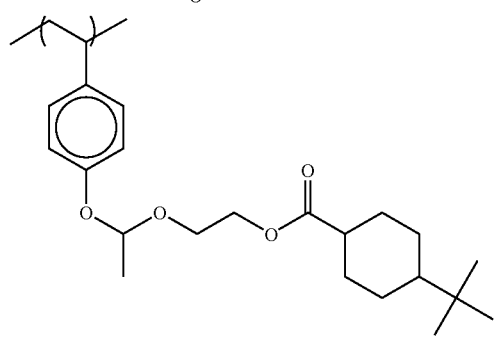
(R-19)
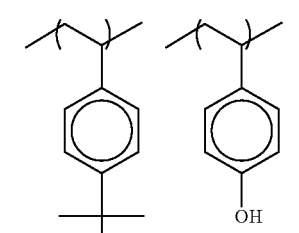
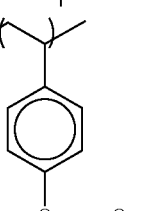
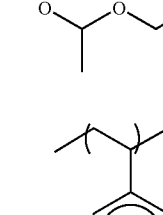
(R-20)
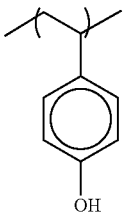

-continued

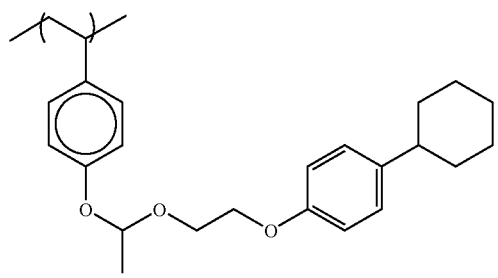

(R-21)

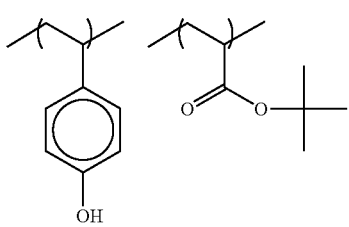

(R-22)

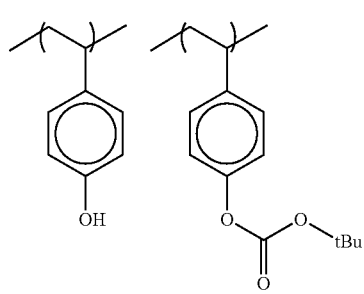

(R-23)

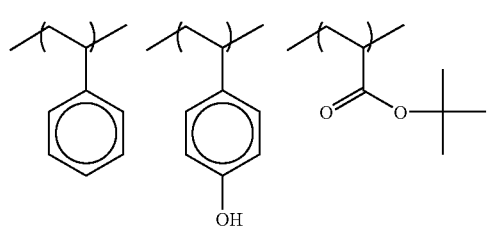

(R-24)

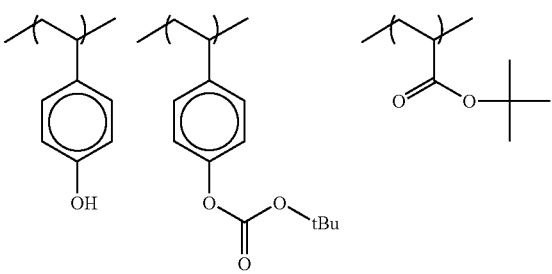

(R-25)

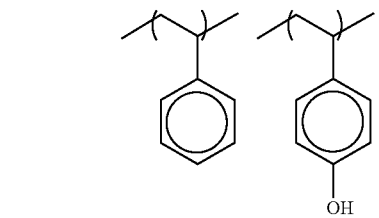

-continued

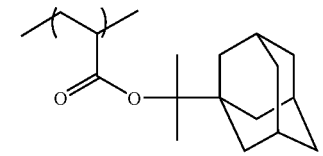

(R-26)

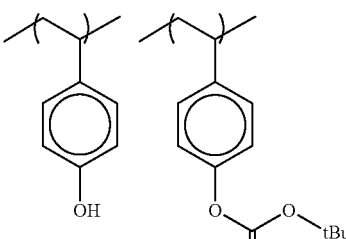

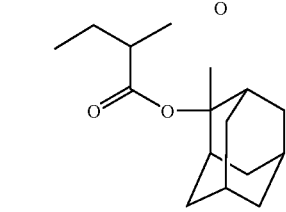

(R-27)

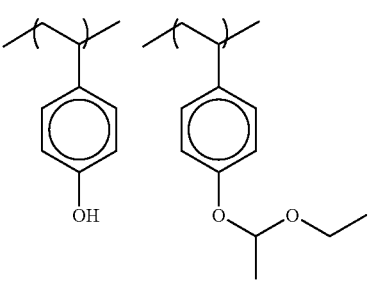

(R-28)

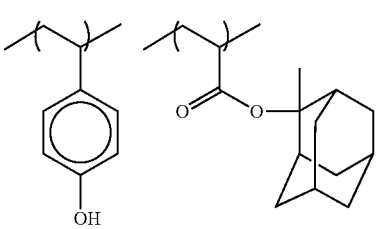

In the examples shown above, tBu represents t-butyl.

The content of acid-dissociable groups in a resin is expressed using the number of the acid-dissociable groups (B) and the number of alkali-soluble groups not protected with an acid-eliminable group (S). Specifically, the content is expressed by B/(B+S). The content thereof is preferably 0.01-0.7, more preferably 0.05-0.50, even more preferably 0.05-0.40.

In the case where the positive type photosensitive composition of the invention is to be irradiated with ArF excimer laser light, the resin as ingredient (B) preferably is a resin which has a monocyclic or polycyclic aliphatic hydrocarbon structure and decomposes by the action of an acid to come to have enhanced solubility in an alkaline developer.

The resin which has a monocyclic or polycyclic aliphatic hydrocarbon structure and decomposes by the action of an acid to come to have enhanced solubility in an alkaline developer (hereinafter referred to also as "alicyclic-hydrocarbon-based acid-decomposable resin") preferably is a resin containing at least one kind of repeating units selected from the group consisting of repeating units having a partial structure which includes an alicyclic hydrocarbon and is represented by any of the following general formulae (pI) to (pVI) and repeating units represented by the following general formula (II-AB).

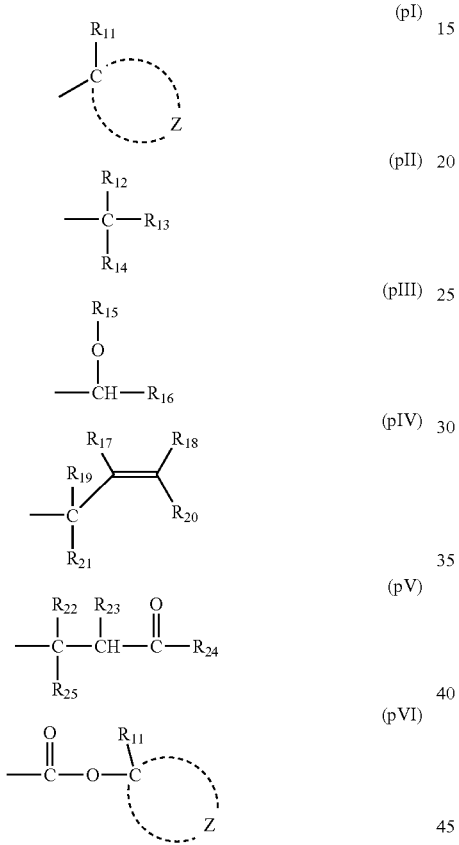

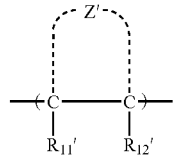

(II-AB)

In formula (II-AB), $R_{11}'$ and $R_{12}'$ each independently represents a hydrogen atom, cyano, halogen atom, or alkyl group; and Z' represents an atomic group which forms an alicyclic structure in cooperation with the two carbon atoms (C—C) bonded thereto.

General formula (II-AB) preferably is the following general formula (II-A) or general formula (II-B).

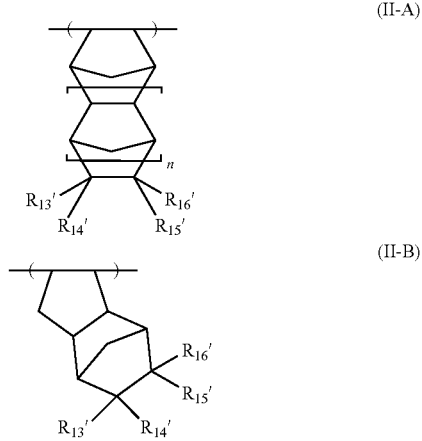

In general formulae (pI) to (pVI), $R_{11}$ represents methyl, ethyl, n-propyl, isopropyl, n-butyl, isobutyl, or sec-butyl, and Z represents an atomic group necessary for forming a cycloalkyl group in cooperation with the carbon atom;

$R_{12}$ to $R_{16}$ each independently represents a linear or branched alkyl group having 1-4 carbon atoms or a cycloalkyl group, provided that at least one of $R_{12}$ to $R_{14}$ or either of $R_{15}$ and $R_{16}$ represents a cycloalkyl group;

$R_{17}$ to $R_{21}$ each independently represents a hydrogen atom, a linear or branched alkyl group having 1-4 carbon atoms, or a cycloalkyl group, provided that at least one of $R_{17}$ to $R_{21}$ represents a cycloalkyl group and that either of $R_{19}$ and $R_{21}$ represents a linear or branched alkyl group having 1-4 carbon atoms or a cycloalkyl group; and $R_{22}$ to $R_{25}$ each independently represents a hydrogen atom, a linear or branched alkyl group having 1-4 carbon atoms, or a cycloalkyl group, provided that at least one of $R_{22}$ to $R_{25}$ represents a cycloalkyl group and that $R_{23}$ and $R_{24}$ may be bonded to each other to form a ring.

In formulae (II-A) and (II-B), $R_{13}'$ to $R_{16}'$ each independently represents a hydrogen atom, halogen atom, cyano, —COOH, —COOR$_5$, group which decomposes by the action of an acid, —C(=O)—X-A'-R$_{17}'$, alkyl group, or cycloalkyl group, wherein $R_5$ represents an alkyl group, cycloalkyl group, or group —Y shown below, X represents an oxygen atom, sulfur atom, —NH—, —NHSO$_2$—, or —NHSO$_2$NH—, and A' represents a single bond or a divalent connecting group, provided that at least two of $R_{13}'$ to $R_{16}'$ may be bonded to each other form a ring; and n represents 0 or 1.

$R_{17}'$ represents —COOH, —COOR$_5$, —CN, hydroxy, alkoxy, —CO—NH—R$_6$, —CO—NH—SO$_2$—R$_6$, or group —Y shown below.

$R_6$ represents an alkyl group or a cycloalkyl group.

Group —Y is as follows.

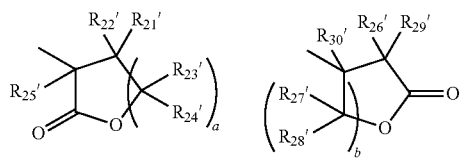

In group —Y, $R_{21}'$ to $R_{30}'$ each independently represents a hydrogen atom or an alkyl group; and a and b each represent 1 or 2.

In general formulae (pI) to (pVI), the alkyl groups represented by $R_{12}$ to $R_{25}$ are linear or branched alkyl groups having 1-4 carbon atoms. Examples of the alkyl groups include methyl, ethyl, n-propyl, isopropyl, n-butyl, isobutyl, sec-butyl, and t-butyl.

Examples of substituents which may be possessed by those alkyl and alkoxy groups include alkoxy groups having 1-4 carbon atoms, halogen atoms (fluorine, chlorine, bromine, and iodine atoms), and acyl, acyloxy, cyano, hydroxy, carboxy, alkoxycarbonyl, and nitro groups.

The cycloalkyl groups represented by $R_{11}$ to $R_{25}$ and the cycloalkyl group formed by Z and a carbon atom may be monocyclic or polycyclic. Examples thereof include groups having a monocyclic, bicyclic, tricyclic, or tetracyclic structure having 5 or more carbon atoms, preferably 6-30 carbon atoms, especially preferably 7-25 carbon atoms. These cycloalkyl groups may have substituents.

Preferred examples of the cycloalkyl groups include adamantyl, noradamantyl, decalin residues, tricyclodecanyl, tetracyclodecanyl, norbornyl, cedrol, cyclohexyl, cycloheptyl, cyclooctyl, cyclodecanyl, and cyclododecanyl. More preferred examples thereof include adamantyl, decalin residues, norbornyl, cedrol, cyclohexyl, cycloheptyl, cyclooctyl, cyclodecanyl, and cyclododecanyl.

Examples of the substituents of those cycloalkyl groups include alkyl groups, halogen atoms, and hydroxy, alkoxy, carboxyl, and alkoxycarbonyl groups. The alkyl groups preferably are lower alkyl groups such as methyl, ethyl, propyl, isopropyl, and butyl, and more preferably are selected from the group consisting of methyl, ethyl, propyl, and isopropyl. Examples of the alkoxy groups include ones having 1-4 carbon atoms, such as methoxy, ethoxy, propoxy, and butoxy. Examples of substituents which may be possessed by those alkyl, alkoxy, and alkoxycarbonyl groups include hydroxy, halogen atoms, and alkoxy groups.

The structures represented by general formulae (pI) to (pVI) in the resin can be used for the protection of alkali-soluble groups. Examples of the alkali-soluble groups include various groups known in this technical field.

Examples thereof include carboxy, sulfo, phenol, and thiol groups. Preferred are carboxy and sulfo groups.

Preferred examples of the alkali-soluble groups protected by a structure represented by any of general formulae (pI) to (pVI) in the resin include the structure formed by replacing the hydrogen atom of a carboxyl group by the structure represented by any of general formulae (pI) to (pVI).

Repeating units having an alkali-soluble group protected by a structure represented by any of general formulae (pI) to (pVI) preferably are repeating units represented by the following general formula (pA).

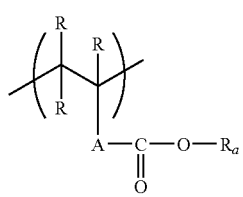

(pA)

In general formula (pA), R represents a hydrogen atom, halogen atom, or linear or branched alkyl group having 1-4 carbon atoms. The R's may be the same or different.

Symbol A represents one member or a combination of two or more members selected from the group consisting of a single bond and alkylene, ether, thioether, carbonyl, ester, amide, sulfonamide, urethane, and urea groups.

$R_a$ represents a group represented by any of formulae (pI) to (pVI).

The repeating units represented by general formula (pA) most preferably are repeating units derived from a 2-alkyl-2-adamantyl (meth)acrylate or a dialkyl(1-adamantyl)methyl (meth)acrylate.

Specific examples of the repeating units represented by general formula (pA) are shown below.

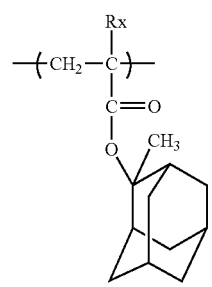

1

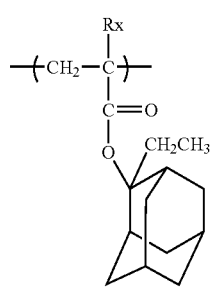

2

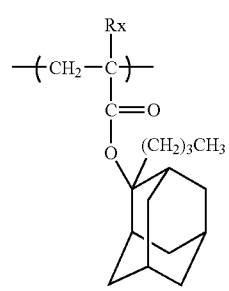

3

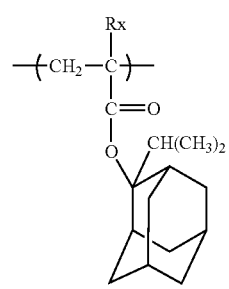

4

5
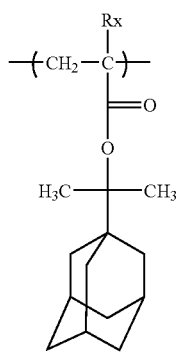
6
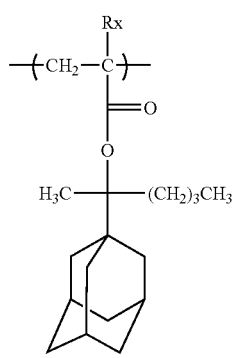
7
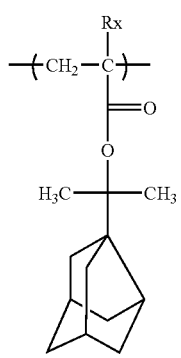
8
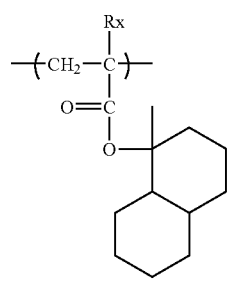
9
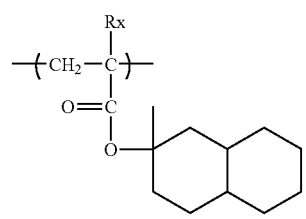
10
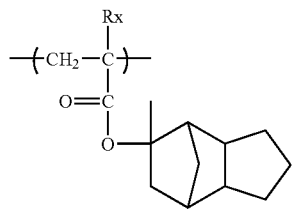
11
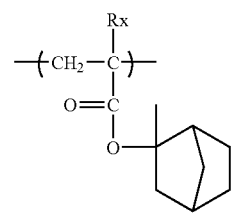
12
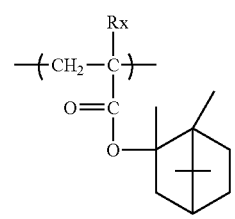
13
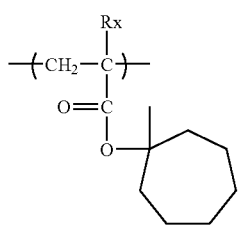
14
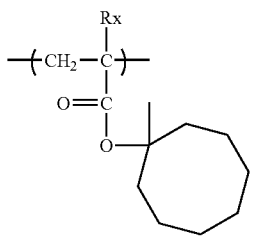
15
16
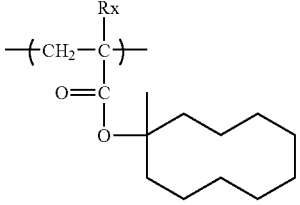

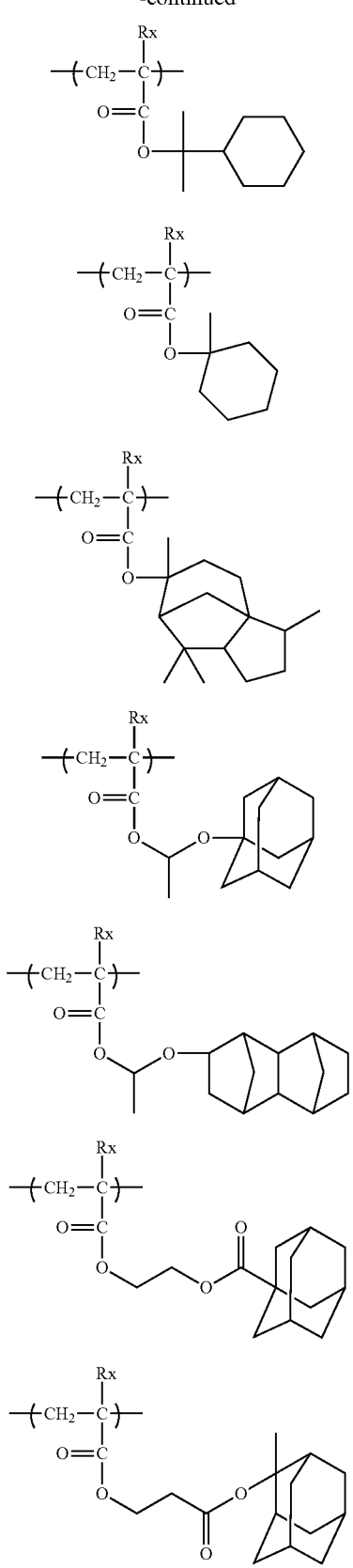

(In the formulae, Rx is H, CH₃, or CF₃.)

In general formula (II-AB), $R_{11}'$ and $R_{12}'$ each independently represents a hydrogen atom, cyano, halogen atom, or alkyl group.

Z' represents an atomic group which forms an alicyclic structure in cooperation with the two carbon atoms (C—C) bonded thereto.

Examples of the halogen atoms represented by $R_{11}'$ and $R_{12}'$ include chlorine, bromine, fluorine, and iodine atoms.

The alkyl groups represented by $R_{11}'$, $R_{12}'$, and $R_{21}'$ to $R_{30}'$ preferably are linear or branched alkyl groups having 1-10 carbon atoms, and more preferably are linear or branched alkyl groups having 1-6 carbon atoms. Even more preferably, the alkyl groups are methyl, ethyl, propyl, isopropyl, n-butyl, isobutyl, sec-butyl, or t-butyl.

Examples of substituents of those alkyl groups include hydroxy, halogen atoms, and carboxy, alkoxy, acyl, cyano, and acyloxy groups. Examples of the halogen atoms include chlorine, bromine, fluorine, and iodine atoms. Examples of the alkoxy groups include ones having 1-4 carbon atoms, such as methoxy, ethoxy, propoxy, and butoxy. Examples of the acyl groups include formyl and acetyl. Examples of the acyloxy groups include acetoxy.

The atomic group represented by Z', which forms an alicyclic structure, is an atomic group which serves to form, in the resin, repeating units of an alicyclic hydrocarbon which may have one or more substituents. Especially preferred is an atomic group which forms a bridged alicyclic structure for forming bridged repeating units of an alicyclic hydrocarbon.

Examples of the framework of the alicyclic hydrocarbon to be formed include the same frameworks as those of the alicyclic hydrocarbon groups represented by $R_{11}$ to $R_{25}$ in general formulae (pI) to (pVI).

The framework of the alicyclic hydrocarbon may have one or more substituents. Examples of the substituents include $R_{13}'$ to $R_{16}'$ in general formula (II-A) or (II-B).

Of the repeating units having a bridged alicyclic hydrocarbon, repeating units represented by general formula (II-A) or (II-B) are more preferred.

In the alicyclic-hydrocarbon-based acid-decomposable resin according to the invention, the acid-dissociable groups each may be contained in the —C(=O)—X-A'—$R_{17}'$ or may be contained as a substituent possessed by Z' in general formula (II-AB).

The structure of each acid-dissociable group can be expressed by —C(=O)—$X_1$—$R_0$.

Examples of $R_0$ in the formula include tertiary alkyl groups such as t-butyl and t-amyl, isobornyl, 1-alkoxyethyl groups such as 1-ethoxyethyl, 1-butoxyethyl, 1-isobutoxyethyl, and 1-cyclohexyloxyethyl, alkoxymethyl groups such as 1-methoxymethyl and 1-ethoxymethyl, 3-oxoalkyl groups, tetrahydropyranyl, tetrahydrofuranyl, trialkylsilyl ester groups, 3-oxocyclohexyl ester groups, 2-methyl-2-adamantyl, and mevalonolactone residues. $X_1$ has the same meaning as X described above.

Examples of the halogen atoms represented by $R_{13}'$ to $R_{16}'$ include chlorine, bromine, fluorine, and iodine atoms.

The alkyl groups represented by $R_5$, $R_6$, and $R_{13}'$ to $R_{16}'$ preferably are linear or branched alkyl groups having 1-10 carbon atoms, and more preferably are linear or branched alkyl groups having 1-6 carbon atoms. Even more preferably, the alkyl groups are methyl, ethyl, propyl, isopropyl, n-butyl, isobutyl, sec-butyl, or t-butyl.

Examples of the cycloalkyl groups represented by $R_5$, $R_6$, and $R_{13}'$ to $R_{16}'$ include monocyclic alkyl groups and bridged hydrocarbons. Specific examples thereof include cyclopropyl, cyclopentyl, cyclohexyl, adamantyl, 2-methyl-2-adamantyl, norbornyl, bornyl, isobornyl, tricyclodecanyl, dicyclopentenyl, norbornane epoxy groups, menthyl, isomenthyl, neomenthyl, and tetracyclododecanyl.

Examples of the ring formed by the bonding of at least two of $R_{13}'$ to $R_{16}'$ include rings having 5-12 carbon atoms, such as cyclopentene, cyclohexene, cycloheptane, and cyclooctane.

Examples of the alkoxy group represented by $R_{17}'$ include ones having 1-4 carbon atoms, such as methoxy, ethoxy, propoxy, and butoxy.

Examples of substituents of those alkyl groups, cycloalkyl groups, and alkoxy groups include hydroxy, halogen atoms, and carboxyl, alkoxy, acyl, cyano, acyloxy, alkyl, and cycloalkyl groups. Examples of the halogen atoms include chlorine, bromine, fluorine, and iodine atoms. Examples of the alkoxy groups include ones having 1-4 carbon atoms, such as methoxy, ethoxy, propoxy, and butoxy. Examples of the acyl groups include formyl and acetyl. Examples of the acyloxy groups include acetoxy.

Examples of the alkyl groups and cyclic hydrocarbon groups include those enumerated above.

Examples of the divalent connecting group represented by A' include one group or a combination of two or more groups selected from the group consisting of alkylene, ether, thioether, carbonyl, ester, amide, sulfonamide, urethane, and urea groups.

In the alicyclic-hydrocarbon-based acid-decomposable resin according to the invention, groups which dissociate by the action of an acid can be contained in at least one kind of repeating units selected from the group consisting of repeating units having a partial structure which includes an alicyclic hydrocarbon and is represented by any of general formulae (pI) to (pVI), repeating units represented by general formula (II-AB), and repeating units derived from the comonomer ingredients which will be described later.

Various substituents of $R_{13}'$ to $R_{16}'$ in general formula (II-A) or (II-B) serve as substituents of the atomic group forming an alicyclic structure in general formula (II-AB) or of the atomic group Z forming a bridged alicyclic structure in the formula.

Specific examples of the repeating units represented by general formula (II-A) or (II-B) include the following. However, the repeating units in the invention should not be construed as being limited to the following examples.

[II-1]

[II-2]

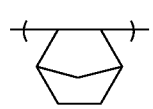
[II-3]

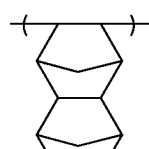

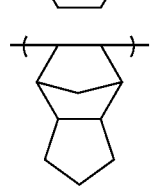

-continued

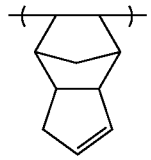
[II-4]

[II-5]

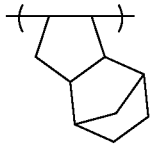
[II-6]

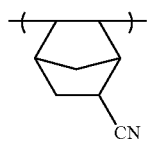
[II-7]

[II-8]

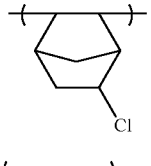
[II-9]

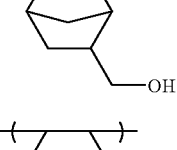
[II-10]

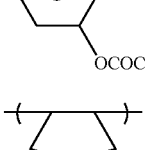
[II-11]

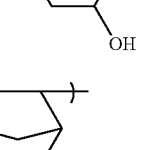
[II-12]

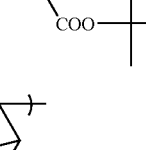
[II-13]

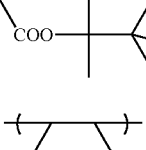

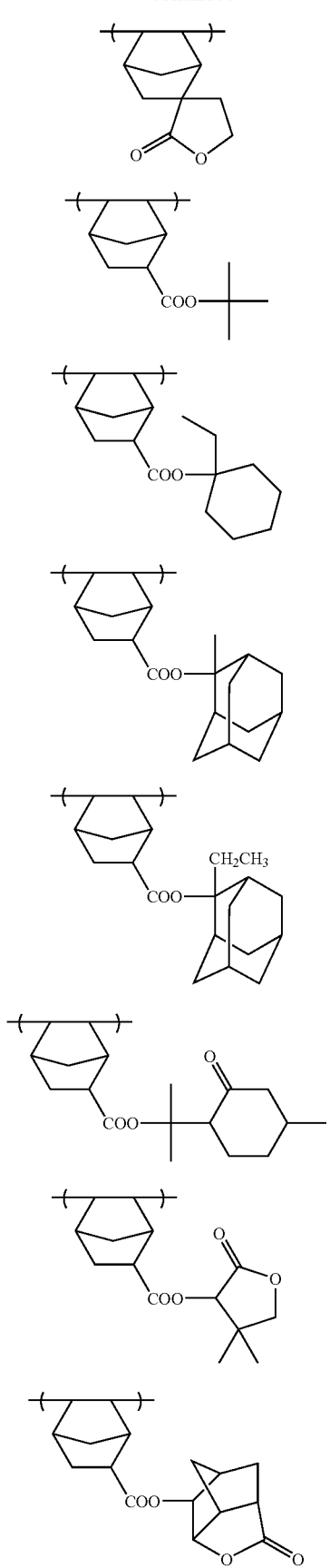
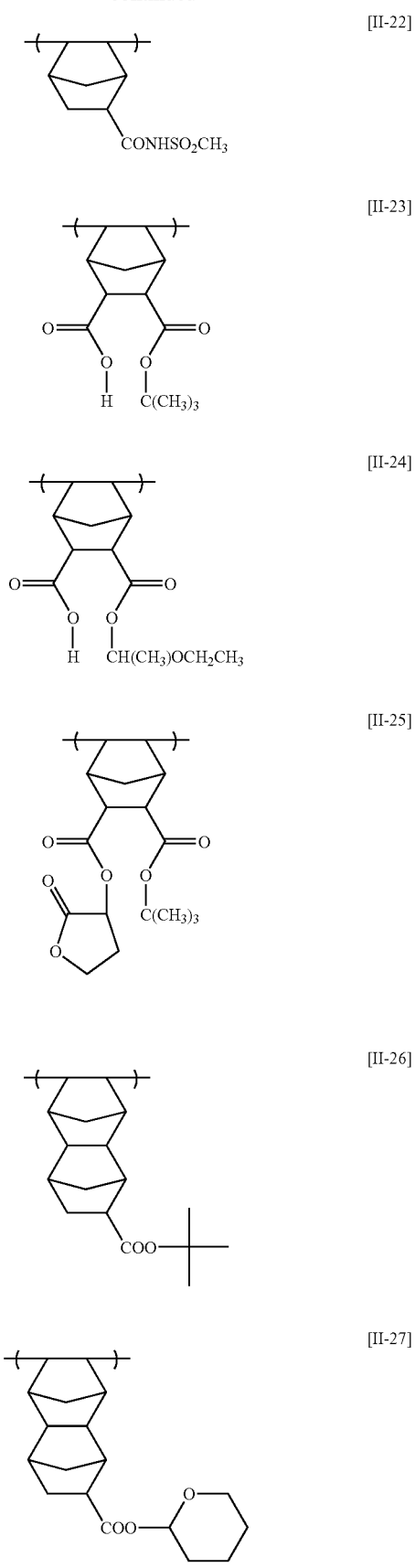

[II-28]
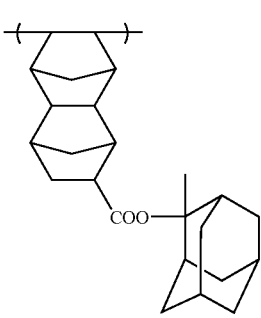

[II-29]
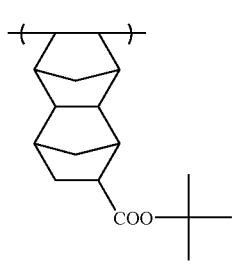

[II-30]
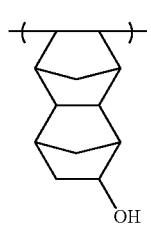

[II-31]
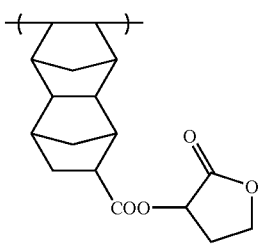

[II-32]
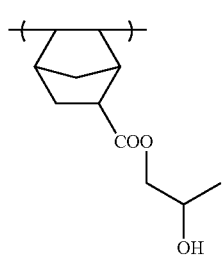

The alicyclic-hydrocarbon-based acid-decomposable resin according to the invention preferably has a lactone group, and more preferably has repeating units having a lactone structure represented by the following general formula (Lc) or any of the following general formulae (V-1) to (V-5). The resin may have groups having a lactone structure which have been directly bonded to the main chain.

(Lc)
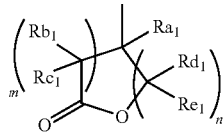

(V-1)
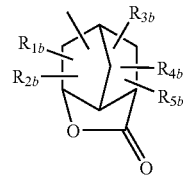

(V-2), (V-3)
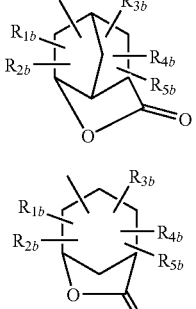

(V-4), (V-5)
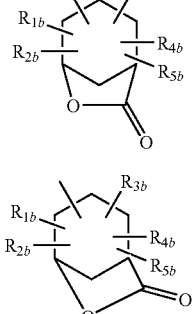

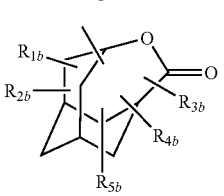

$Ra_1$, $Rb_1$, $Rc_1$, $Rd_1$, and $Re_1$ in general formula (Lc) each independently represents a hydrogen atom or an alkyl group. Symbols m and n each independently represents an integer of 0 to 3, provided that m+n is from 2 to 6.

In general formulae (V-1) to (V-5), $R_{1b}$ to $R_{5b}$ each independently represents a hydrocarbon atom or an alkyl, cycloalkyl, alkoxy, alkoxycarbonyl, alkylsulfonylamino, or alkenyl group, provided that two of $R_{1b}$ to $R_{5b}$ may be bonded to each other to form a ring.

Examples of the alkyl groups represented by $R_{a1}$ to $R_{e1}$ in general formula (Lc) and of the alkyl groups in the alkyl, alkoxy, alkoxycarbonyl, and alkylsulfonylamino groups represented by $R_{1b}$ to $R_{5b}$ in general formulae (V-1) to (V-5) include linear or branched alkyl groups which may have substituents. Preferred examples of the substituents which may be possessed include hydroxy, halogen atoms, and carboxyl, alkoxy, acyl, cyano, acyloxy, and cycloalkyl groups.

Examples of the repeating units having a group having a lactone structure represented by general formula (Lc) or any of general formulae (V-1) to (V-5) include: repeating units represented by general formula (II-A) or (II-B) in which at least one of $R_{13}'$ to $R_{16}'$ has a group represented by general formula (Lc) or any of general formulae (V-1) to (V-5) (e.g., units in which the $R_5$ in —COOR$_5$ is a group represented by general formula (Lc) or any of general formulae (V-1) to (V-5)); and repeating units represented by the following general formula (AI).

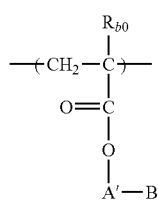

In general formula (AI), $R_{b0}$ represents a hydrogen atom, halogen atom, or alkyl group having 1-4 carbon atoms. Preferred examples of substituents which may be possessed by the alkyl group represented by $R_{b0}$ include the substituents enumerated above as preferred substituents which may be possessed by the alkyl group represented by $R_{1b}$ in general formulae (V-1) to (V-5).

Examples of the halogen atom represented by $R_{b0}$ include fluorine, chlorine, bromine, and iodine atoms. $R_{b0}$ preferably is a hydrogen atom.

A' represents a single bond, an ether, ester, carbonyl, or alkylene group, or a divalent group consisting of a combination of two or more of these.

$B_2$ represents a group represented by general formula (Lc) or any of general formulae (V-1) to (V-5).

Specific examples of the repeating units having a group having a lactone structure are shown below, but the repeating units in the invention should not be construed as being limited to the following examples.

(In the formulae, Rx is H, CH$_3$, or CF$_3$.)

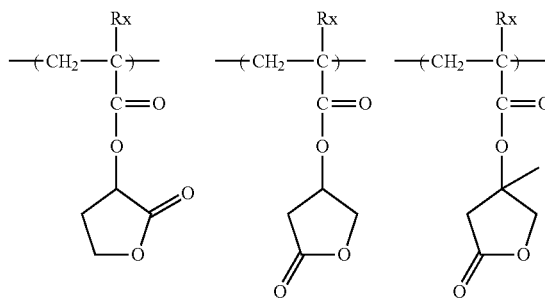

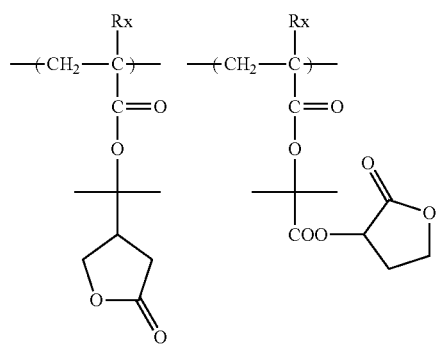

-continued

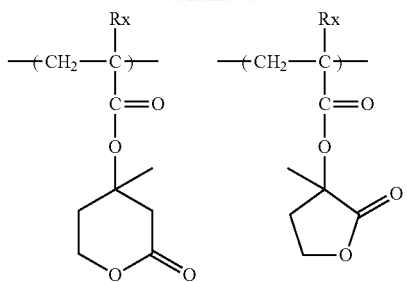

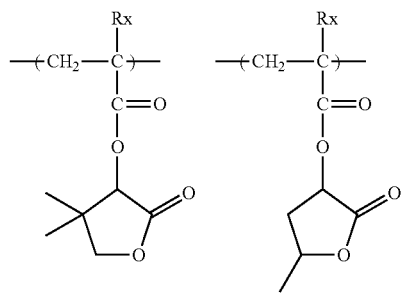

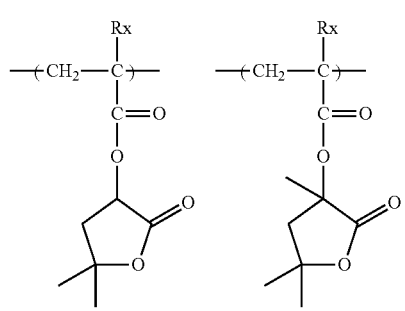

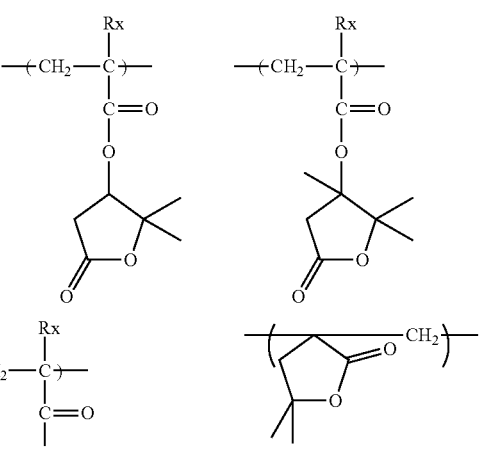

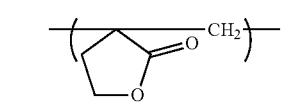

(In the formulae, Rx is H, CH$_3$, or CF$_3$.)

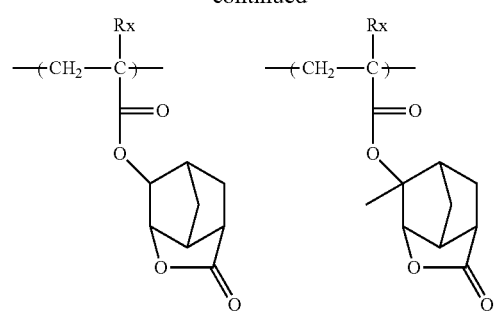
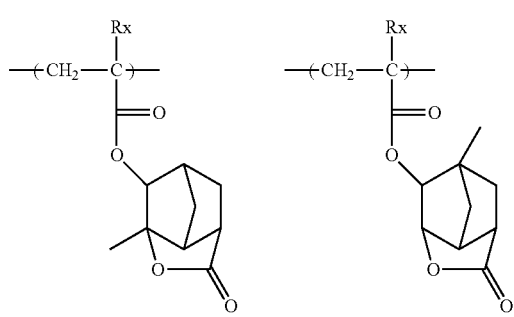
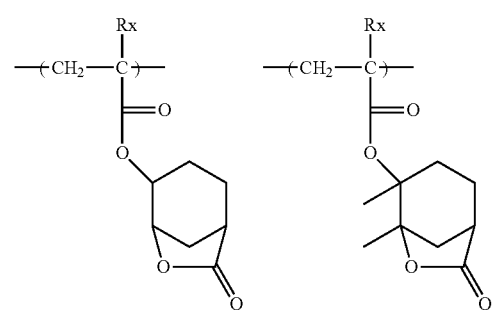
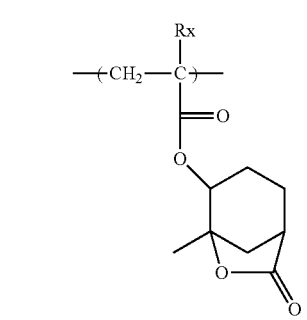
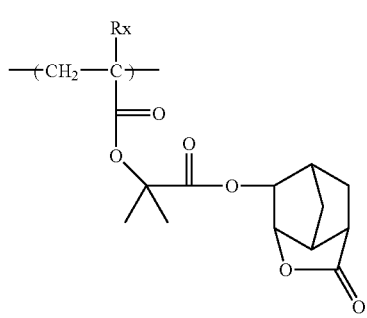
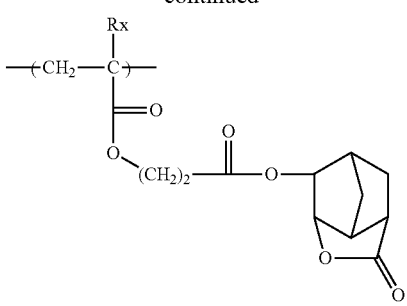
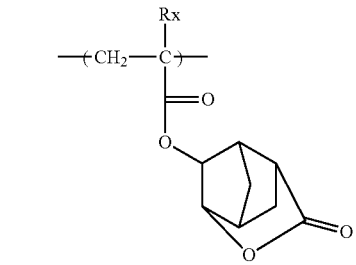
(In the formulae, Rx is H, CH₃, or CF₃.)
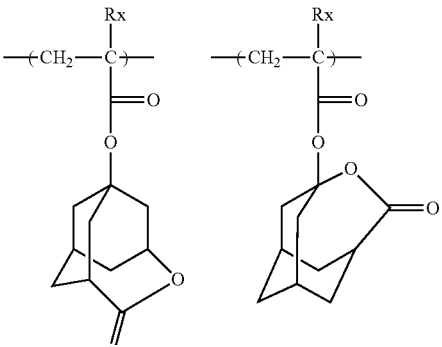
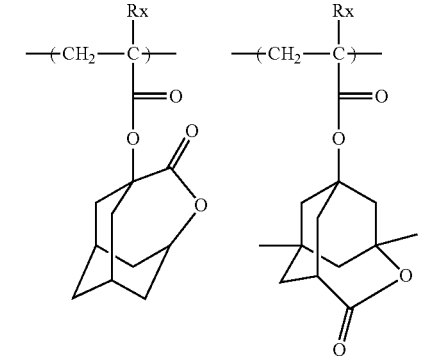

-continued

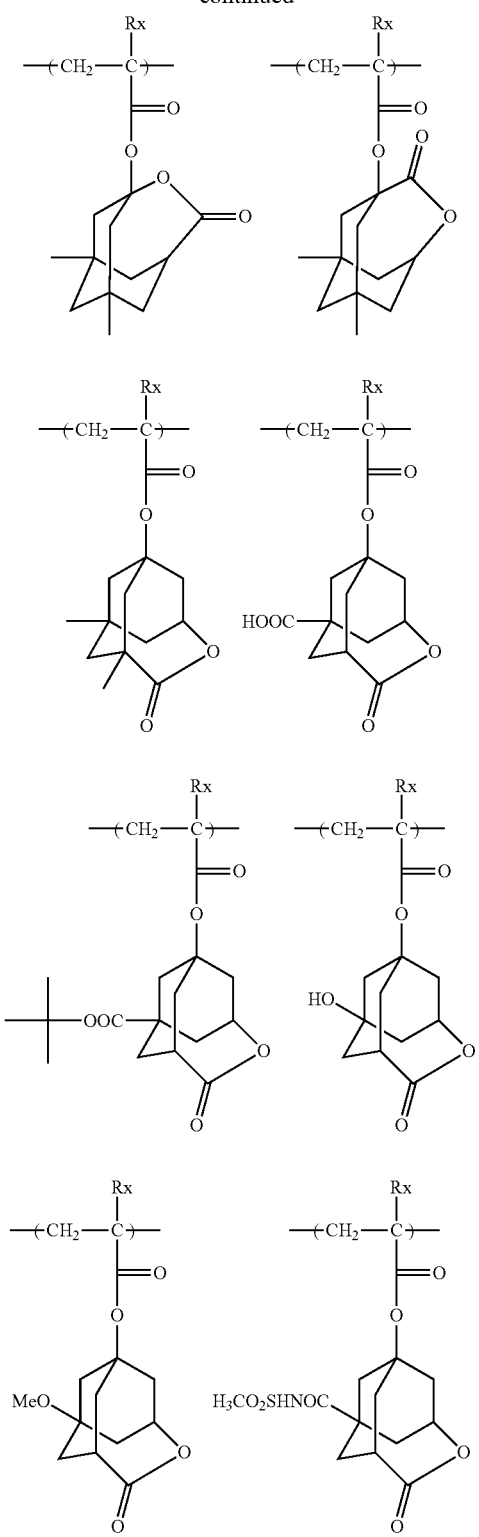

The alicyclic-hydrocarbon-based acid-decomposable resin according to the invention may contain repeating units having a group which has an adamantane framework and is represented by the following general formula (VII).

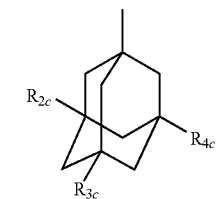

(VII)

In general formula (VII), $R_{2c}$ to $R_{4c}$ each independently represents a hydrogen atom or hydroxy, provided that at least one of $R_{2c}$ to $R_{4c}$ represents hydroxy.

The group represented by general formula (VII) preferably is a group having two hydroxy groups or one hydroxy group, and more preferably is a group having two hydroxy groups.

Examples of the repeating units having a group represented by general formula (VII) include: repeating units represented by general formula (II-A) or (II-B) in which at least one of $R_{13}'$ to $R_{16}'$ has a group represented by general formula (VII) (e.g., units in which the $R_5$ in $—COOR_5$ is a group represented by general formula (VII)); and repeating units represented by the following general formula (AII).

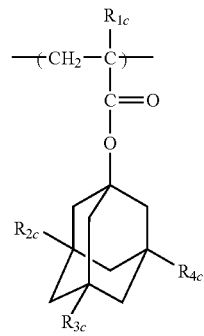

In general formula (AII), $R_{1c}$ represents a hydrogen atom or methyl.

$R_{2c}$ to $R_{4c}$ each independently represents a hydrogen atom or hydroxy, provided that at least one of $R_{2c}$ to $R_{4c}$ represents hydroxy. The repeating units preferably are ones in which two of $R_{2c}$ to $R_{4c}$ are hydroxy.

Specific examples of the repeating units represented by general formula (AII) are shown below, but the repeating units in the invention should not be construed as being limited to the following examples.

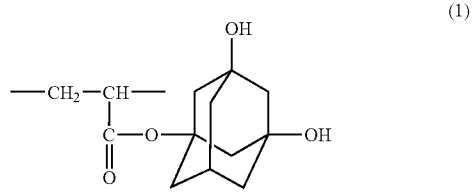

(1)

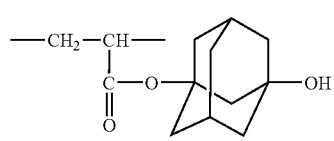

(2)

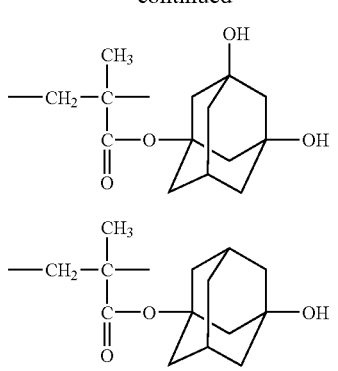

The alicyclic-hydrocarbon-based acid-decomposable resin according to the invention may contain repeating units represented by the following general formula (VIII).

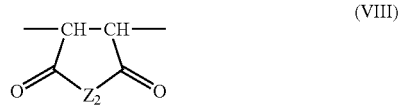

In general formula (VIII), $Z_2$ represents —O— or —N($R_{41}$)—. $R_{41}$ represents a hydrogen atom, hydroxy, alkyl group, or —OSO$_2$—$R_{42}$. $R_{42}$ represents an alkyl group, cycloalkyl group, or camphor residue. The alkyl group represented by $R_{41}$ or $R_{42}$ may be substituted by a halogen atom (preferably fluorine atom), etc.

Specific examples of the repeating units represented by general formula (VIII) include the following, but the repeating units in the invention should not be construed as being limited to these examples.

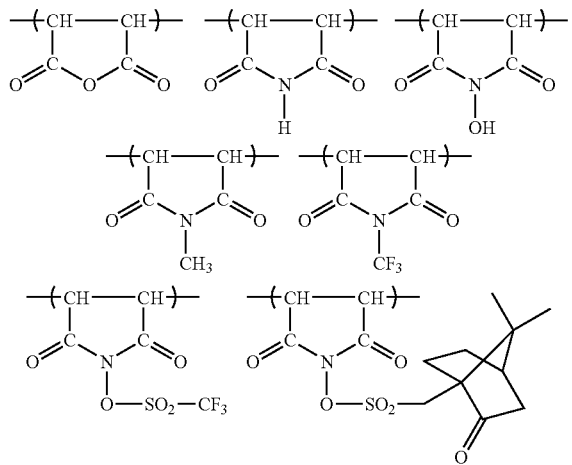

The alicyclic-hydrocarbon-based acid-decomposable resin according to the invention preferably has repeating units each having an alkali-soluble group, and more preferably has repeating units each having a carboxyl group. The presence of these repeating units enhances resolution in contact hole applications. The repeating units having a carboxyl group may be either repeating units which constitute a resin main chain having carboxyl groups directly bonded thereto, such as the repeating units derived from acrylic acid or methacrylic acid, or repeating units which constitute a resin main chain having carboxyl groups each bonded thereto through a connecting group. Both of these two types of repeating units are preferred. The connecting group may have a monocyclic or polycyclic hydrocarbon structure. Most preferred are repeating units derived from acrylic acid or methacrylic acid.

The alicyclic-hydrocarbon-based acid-decomposable resin according to the invention can contain various repeating structural units besides the repeating structural units described above for the purpose of regulating dry etching resistance, suitability for standard developing solutions, adhesion to substrates, resist profile, and general properties required of resists, such as resolution, heat resistance, sensitivity, etc.

Examples of such repeating structural units include the repeating structural units corresponding to the monomers shown below, but the optional units should not be construed as being limited to these.

Thus, performances required of the alicyclic-hydrocarbon-based acid-decomposable resin, in particular,
 (1) solubility in solvent for application,
 (2) film-forming properties (glass transition point),
 (3) alkali developability,
 (4) resist loss (hydrophilicity/hydrophobicity, selection of alkali-soluble group),
 (5) adhesion of unexposed areas to substrate,
 (6) dry etching resistance,
and the like can be delicately regulated.

Examples of such monomers include compounds having one addition-polymerizable unsaturated bond, such as acrylic esters, methacrylic esters, acrylamide and analogues thereof, methacrylamide and analogues thereof, allyl compounds, vinyl ethers, and vinyl esters.

Besides such monomers corresponding to those various repeating structural units, any addition-polymerizable unsaturated compound copolymerizable with those monomers may have been copolymerized.

In the alicyclic-hydrocarbon-based acid-decomposable resin, the molar proportion of each kind of repeating structural units to be contained is suitably determined in order to regulate resist properties including dry etching resistance, suitability for standard developing solutions, adhesion to substrates, and resist profile and general performances required of resists, such as resolution, heat resistance, and sensitivity.

Preferred embodiments of the alicyclic-hydrocarbon-based acid-decomposable resin according to the invention include the following:
 (1) one containing repeating units having a partial structure which includes an alicyclic hydrocarbon and is represented by any of general formulae (pI) to (pVI) (side chain type); and
 (2) one containing repeating units represented by general formula (II-AB) (main chain type),
  provided that examples of the resin (2) include the following:
 (3) one comprising repeating units represented by general formula (II-AB), a maleic anhydride derivative, and a (meth)acrylate structure (hybrid type).

In the alicyclic-hydrocarbon-based acid-decomposable resin, the content of the repeating units having an acid-dissociable group is preferably 10-60% by mole, more preferably 20-50% by mole, even more preferably 25-40% by mole, based on all repeating structural units.

It is preferred in the invention that the resin should contain at least one kind of repeating methacrylic ester units and at least one kind of repeating acrylic ester units as repeating units each having an acid-dissociable group. The proportion of the acrylic ester units to the methacrylic ester units is generally from 10/90 to 90/10, preferably from 20/80 to 80/20, more preferably from 30/70 to 70/30, most preferably from 40/60 to 60/40.

In the alicyclic-hydrocarbon-based acid-decomposable resin, the content of the repeating units having a partial structure which includes an alicyclic hydrocarbon and is represented by any of general formulae (pI) to (pVI) is preferably 30-70% by mole, more preferably 35-65% by mole, even more preferably 40-60% by mole, based on all repeating structural units.

In the alicyclic-hydrocarbon-based acid-decomposable resin, the content of the repeating units represented by general formula (II-AB) is preferably 10-60% by mole, more preferably 15-55% by mole, even more preferably 20-50% by mole, based on all repeating structural units.

The content of the repeating structural units derived from those optionally usable comonomers in the resin also can be suitably determined according to the desired resist performances. In general, however, the content thereof is preferably 99% by mole or lower, more preferably 90% by mole or lower, even more preferably 80% by mole or lower, based on the total mole amount of the repeating structural units having a partial structure which includes an alicyclic hydrocarbon and is represented by any of general formulae (pI) to (pVI) and the repeating units represented by general formula (II-AB).

In the case where the composition of the invention is to be used for ArF exposure, the resin preferably has no aromatic group from the standpoint of transparency to ArF light.

The alicyclic-hydrocarbon-based acid-decomposable resin to be used in the invention can be synthesized by ordinary methods (e.g., radical polymerization). For example, a general synthesis method is as follows. Monomers are charged into a reaction vessel at a time or in the course of reaction. According to need, the monomers are dissolved in a reaction solvent, e.g., an ether such as tetrahydrofuran, 1,4-dioxane, or diisopropyl ether, a ketone such as methyl ethyl ketone or methyl isobutyl ketone, an ester solvent such as ethyl acetate, or a solvent capable of dissolving the composition of the invention therein, such as those enumerated later, e.g., propylene glycol monomethyl ether acetate, to prepare a homogeneous solution. Thereafter, polymerization of the reaction mixture is initiated with a commercial free-radical initiator (e.g., azo initiator or peroxide) in an inert gas atmosphere such as nitrogen or argon optionally with heating. The initiator may be added additionally or in portions according to need. After completion of the reaction, the reaction mixture is poured into a solvent and the target polymer is recovered as a powder, solid, etc. The reactant concentration is 20% by mass or higher, preferably 30% by mass or higher, more preferably 40% by mass or higher. The reaction temperature is 10-150° C., preferably 30-120° C., more preferably 50-100° C.

In the case where the composition of the invention is to be used for forming an upper resist layer in a multilayered resist, the resin as ingredient (B) preferably has silicon atoms.

A resin which has silicon atoms in at least either of the main chain or side chains thereof can be used as that resin which has silicon atoms and decomposes by the action of an acid to come to have enhanced solubility in an alkaline developer. Examples of the resin having siloxane structures in side chains thereof include copolymers of an olefinic monomer having one or more silicon atoms in a side chain thereof, maleic anhydride, and a (meth)acrylic acid monomer having an acid-dissociable group in a side chain thereof.

The resin having silicon atoms preferably is a resin having a trialkylsilyl structure or a monocyclic or polycyclic siloxane structure. More preferred is a resin having repeating units having a structure represented by any of the following general formulae (SS-1) to (SS-4). More preferred repeating units are repeating (meth)acrylic ester units, repeating vinyl units, or repeating allyl units each having a structure represented by any of general formulae (SS-1) to (SS-4).

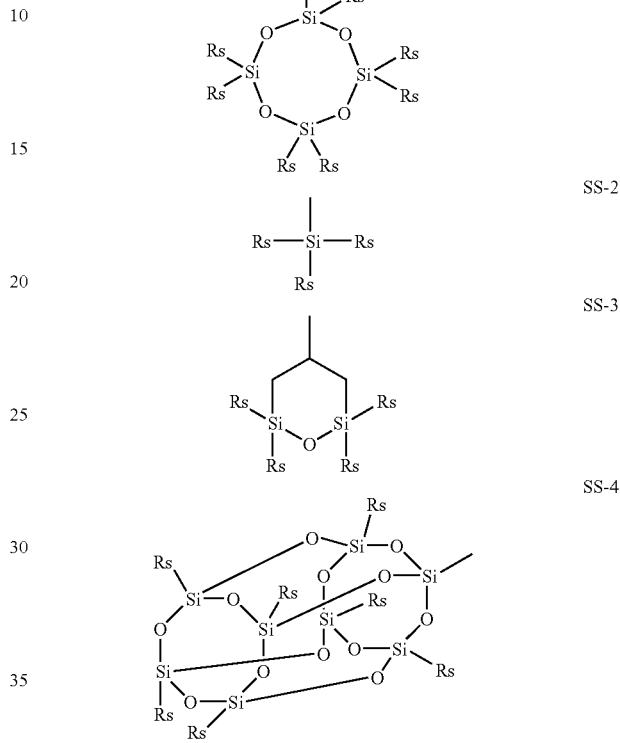

In general formulae (SS-1) to (SS-4), Rs represents an alkyl group having 1-5 carbon atoms and preferably is methyl or ethyl.

The resin having silicon atoms preferably has two or more kinds of repeating units each having one or more silicon atoms. More preferred is a resin having both of repeating units (Sa) each having 1-4 silicon atoms and repeating units (Sb) each having 5-10 silicon atoms. Even more preferred is a resin having at least one kind of repeating units each having a structure represented by any of general formulae (SS-1) to (SS-3) and repeating units having a structure represented by general formula (SS-4).

In the case where the positive type photosensitive composition of the invention is to be irradiated with $F_2$ excimer laser light, the resin as ingredient (B) preferably is a resin which has fluorine-substituted structures in the main chain and/or side chains of the polymer backbone and which decomposes by the action of an acid to come to have enhanced solubility in an alkaline developer (hereinafter referred to also as "fluorine group-containing resin"). More preferred is a resin which contains structures each having in the 1-position a hydroxy group substituted by a fluorine atom or fluoroalkyl group or contains structures each having in the 1-position a group formed by protecting with an acid-dissociable group a hydroxy group substituted by a fluorine atom or fluoroalkyl group. Most preferred is a resin which contains hexafluoro-2-propanol structures or structures formed by protecting the hydroxy group of hexafluoro-2-propanol with an acid-dissociable group. The incorporation of fluorine atoms can improve transparency to far ultraviolet rays, in particular, $F_2$ light (157 nm).

Preferred examples of the fluorine group-containing resin as the acid-decomposable resin (B) include resins having at least one kind of repeating units selected from those represented by the following general formulae (FA) to (FG).

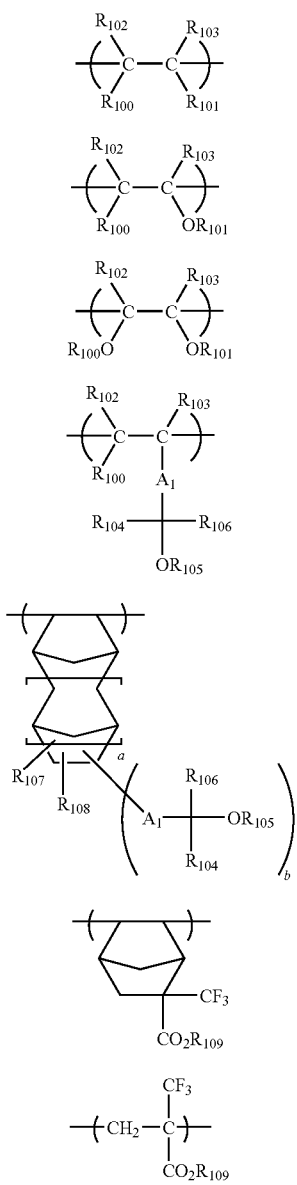

In the general formulae, $R_{100}$ to $R_{103}$ each represent a hydrogen atom, fluorine atom, alkyl group, or aryl group.

$R_{104}$ and $R_{106}$ each represent a hydrogen atom, fluorine atom, or alkyl group, provided that at least one of $R_{104}$ and $R_{106}$ is a fluorine atom or a fluoroalkyl group. Preferably, both $R_{104}$ and $R_{106}$ are trifluoromethyl.

$R_{105}$ is a hydrogen atom, alkyl group, cycloalkyl group, acyl group, alkoxycarbonyl group, or group which dissociates by the action of an acid.

$A_1$ is a single bond or a divalent connecting group, e.g., a linear, branched, or cyclic alkylene group, alkenylene group, arylene group, —OCO—, —COO—, —CON($R_{24}$)—, or connecting group comprising two or more of these. $R_{24}$ is a hydrogen atom or an alkyl group.

$R_{107}$ and $R_{108}$ each are a hydrogen atom, halogen atom, alkyl group, alkoxy group, alkoxycarbonyl group, or group which dissociates by the action of an acid.

$R_{109}$ is a hydrogen atom, alkyl group, cycloalkyl group, or group which dissociates by the action of an acid.

Symbol b is 0, 1, or 2.

$R_{100}$ and $R_{101}$ in general formulae (FA) and (FC) may be bonded to each other through an optionally fluorine-substituted alkylene group (having 1-5 carbon atoms) to form a ring.

The repeating units represented by general formulae (FA) to (FG) each contain at least one, preferably three or more fluorine atoms.

The alkyl groups in general formulae (FA) to (FG) are, for example, alkyl groups having 1-8 carbon atoms. Preferred examples thereof include methyl, ethyl, propyl, n-butyl, sec-butyl, hexyl, 2-ethylhexyl, and octyl.

The cycloalkyl groups may be either monocyclic or polycyclic. Examples of the monocyclic group include ones having 3-8 carbon atoms, such as cyclopropyl, cyclopentyl, cyclohexyl, cycloheptyl, and cyclooctyl. Examples of the polycyclic group include ones having 6-20 carbon atoms, such as adamantyl, norbornyl, isobornyl, camphoryl, dicyclopentyl, α-phenyl, tricyclodecanyl, tetracyclododecyl, and androstanyl. In each of those monocyclic or polycyclic alkyl groups, one or more of the carbon atoms may have been replaced by a heteroatom, e.g., oxygen atom.

The fluoroalkyl groups are, for example, ones having 1-12 carbon atoms. Preferred examples thereof include trifluoromethyl, perfluoroethyl, perfluoropropyl, perfluorobutyl, perfluorohexyl, perfluorooctyl, perfluorooctylethyl, and perfluorododecyl.

The aryl groups are, for example, aryl groups having 6-15 carbon atoms. Preferred examples thereof include phenyl, tolyl, dimethylphenyl, 2,4,6-trimethylphenyl, naphthyl, anthryl, and 9,10-dimethoxyanthryl.

The alkoxy groups are, for example, alkoxy groups having 1-8 carbon atoms. Preferred examples thereof include methoxy, ethoxy, n-propoxy, isopropoxy, butoxy, pentoxy, allyloxy, and octoxy.

The acryl group is, for example, an acyl group having 1-10 carbon atoms. Preferred examples thereof include formyl, acetyl, propanoyl, butanoyl, pivaloyl, octanoyl, and benzoyl.

Examples of the alkoxycarbonyl groups include alkoxycarbonyl groups which preferably are secondary or tertiary, more preferably tertiary, such as isopropoxycarbonyl, t-butoxycarbonyl, t-amyloxycarbonyl, and 1-methyl-1-cyclohexyloxycarbonyl.

Examples of the halogen atoms include fluorine, chlorine, bromine, and iodine atoms.

Preferred examples of the alkylene group include ones having 1-8 carbon atoms, such as methylene, ethylene, propylene, butylene, hexylene, and octylene.

Preferred examples of the alkenylene group include ones having 2-6 carbon atoms, such as ethenylene, propenylene, and butenylene.

Preferred examples of the cycloalkylene group include ones having 5-8 carbon atoms, such as cyclopentylene and cyclohexylene.

Preferred examples of the arylene group include ones having 6-15 carbon atoms, such as phenylene, tolylene, and naphthylene.

Those groups may have substituents. Examples of the substituents include alkyl groups, cycloalkyl groups, aryl groups, and groups having active hydrogen, such as amino, amide, ureido, urethane, hydroxyl, and carboxyl groups. Examples thereof further include halogen atoms (fluorine, chlorine, bromine, and iodine atoms), alkoxy groups (e.g., methoxy, ethoxy, propoxy, and butoxy), thioether groups, acyl groups (e.g., acetyl, propanoyl, and benzoyl), acyloxy groups (e.g., acetoxy, propanoyloxy, and benzoyloxy), alkoxycarbonyl groups (e.g., methoxycarbonyl, ethoxycarbonyl, and propoxycarbonyl), cyano, and nitro.

Examples of the alkyl, cycloalkyl, and aryl groups include the same groups as those enumerated above as examples of such groups. The alkyl groups may be further substituted by one or more fluorine atoms or cycloalkyl groups.

Examples of alkali-soluble groups which dissociate by the action of an acid and are contained in the fluorine group-containing resin according to the invention include —O—C($R_{36}$)($R_{37}$)($R_{38}$), —O—C($R_{36}$)($R_{37}$)($OR_{39}$), —O—COO—C($R_{36}$)($R_{37}$)($R_{38}$), —O—C($R_{01}$)($R_{02}$)COO—C($R_{36}$)($R_{37}$)($R_{38}$), —COO—C($R_{36}$)($R_{37}$)($R_{38}$), and —COO—C($R_{36}$)($R_{37}$)($OR_{39}$).

$R_{36}$ to $R_{39}$ each represent an alkyl, cycloalkyl, aryl, aralkyl, or alkenyl group. $R_{01}$ and $R_{02}$ each represent a hydrogen atom or an alkyl, cycloalkyl, alkenyl (e.g., vinyl, allyl, butenyl, or cyclohexenyl), aralkyl (e.g., benzyl, phenethyl, or naphthylmethyl), or aryl group.

Preferred example thereof include ether or ester groups of tertiary alkyl groups such as t-butyl, t-amyl, 1-alkyl-1-cyclohexyl, 2-alkyl-2-adamantyl, 2-adamantyl-2-propyl, and 2-(4-methylcyclohexyl)-2-propyl groups, acetal or acetal ester groups of, e.g., a 1-alkoxy-1-ethoxy or tetrahydropyranyl group, t-alkyl carbonate groups, and t-alkylcarbonylmethoxy groups.

Specific examples of the repeating structural units represented by general formulae (FA) to (FG) are shown below, but the units in the invention should not be construed as being limited to these.

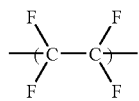
(F-1)

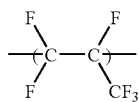
(F-2)

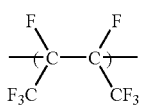
(F-3)

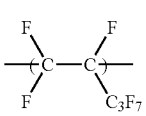
(F-4)

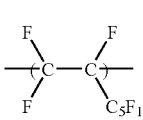
(F-5)

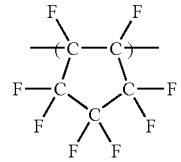
(F-6)

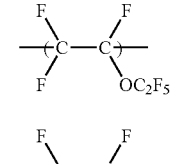
(F-7)

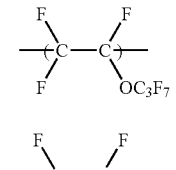
(F-8)

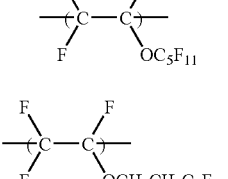
(F-9)

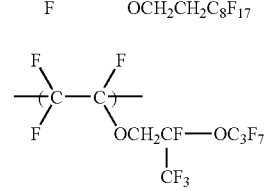
(F-10)

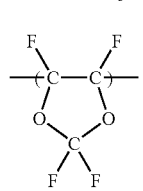
(F-11)

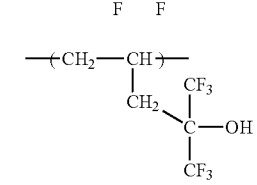
(F-12)

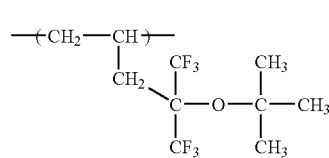
(F-13)

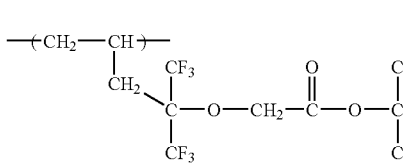
(F-14)

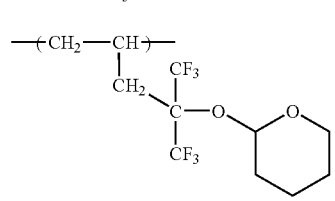
(F-15)

(F-16)

-continued
(F-17)
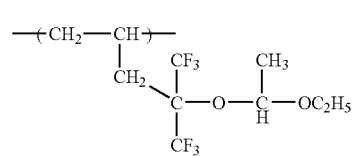
(F-18)
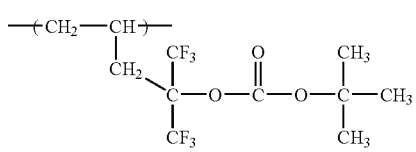
(F-19)
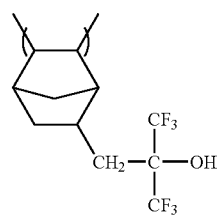
(F-20)
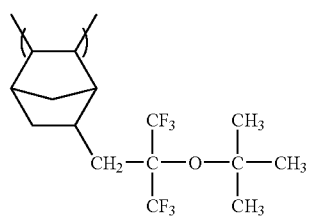
(F-21)
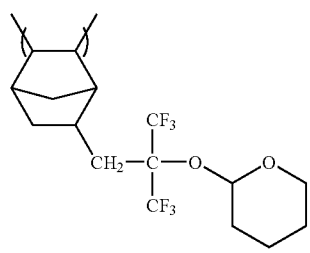
(F-22)
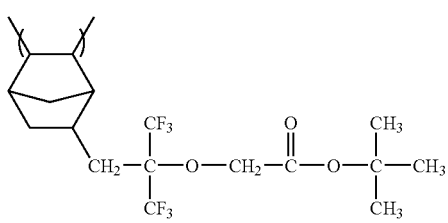
(F-23)
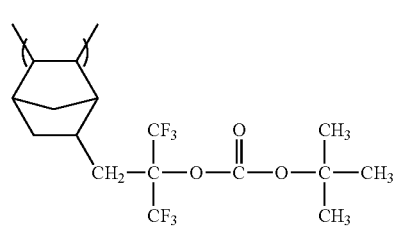
-continued
(F-24)
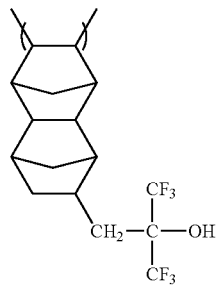
(F-25)
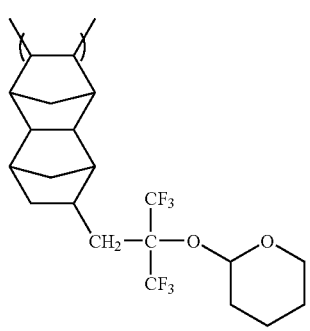
(F-26)
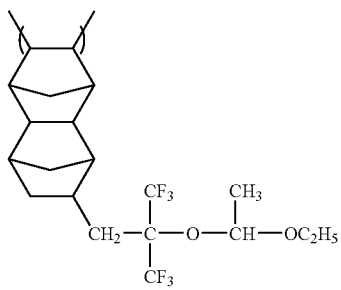
(F-27)
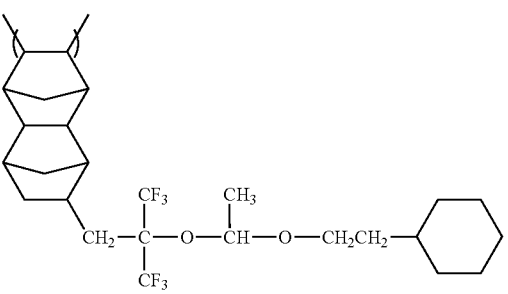
(F-28)
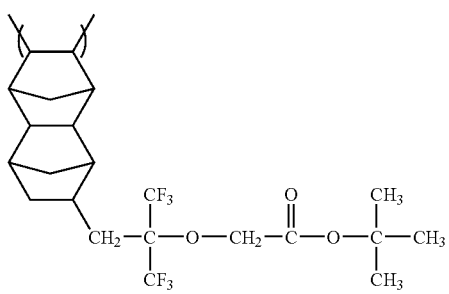

(F-29) 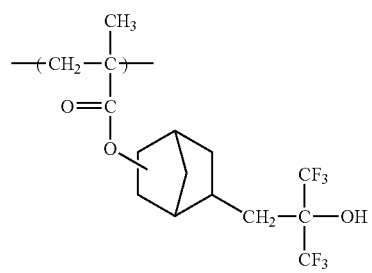
(F-30) 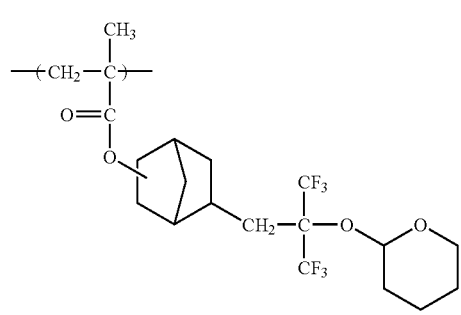
(F-31) 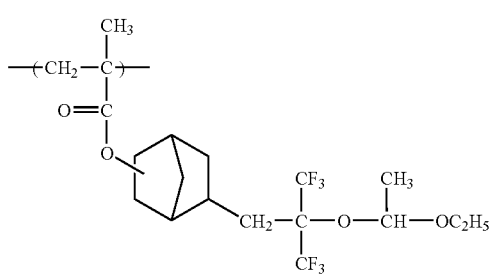
(F-32) 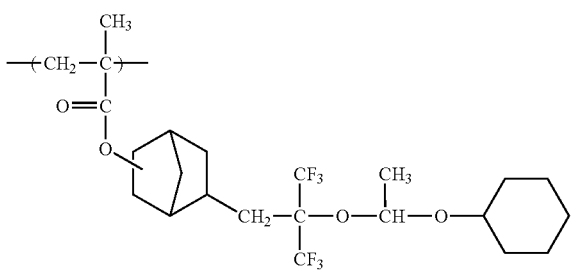
(F-33) 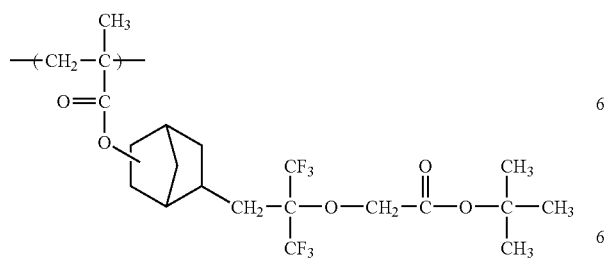
(F-34) 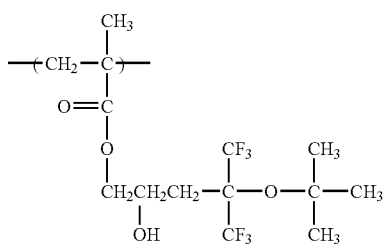
(F-35) 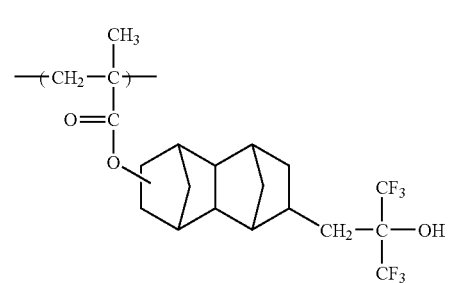
(F-36) 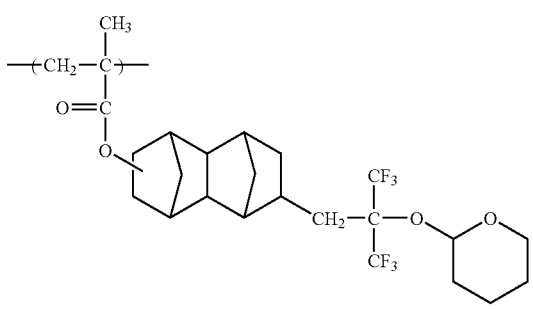
(F-37) 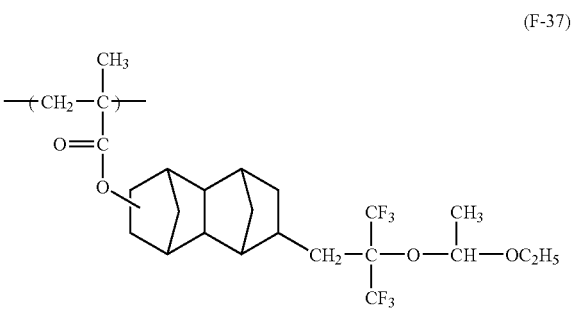
(F-38) 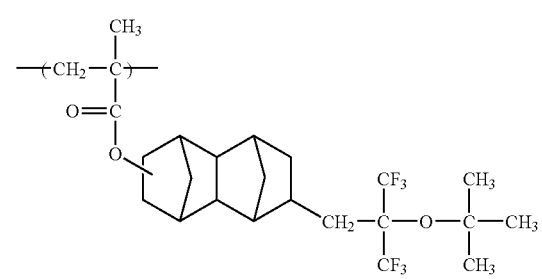

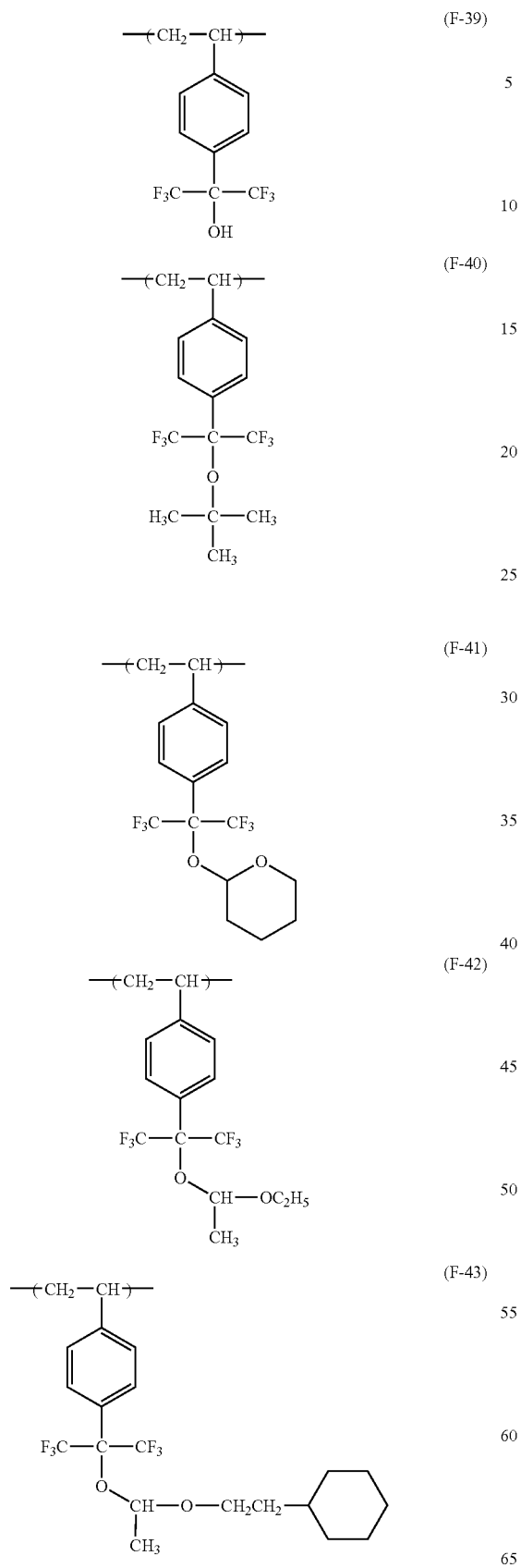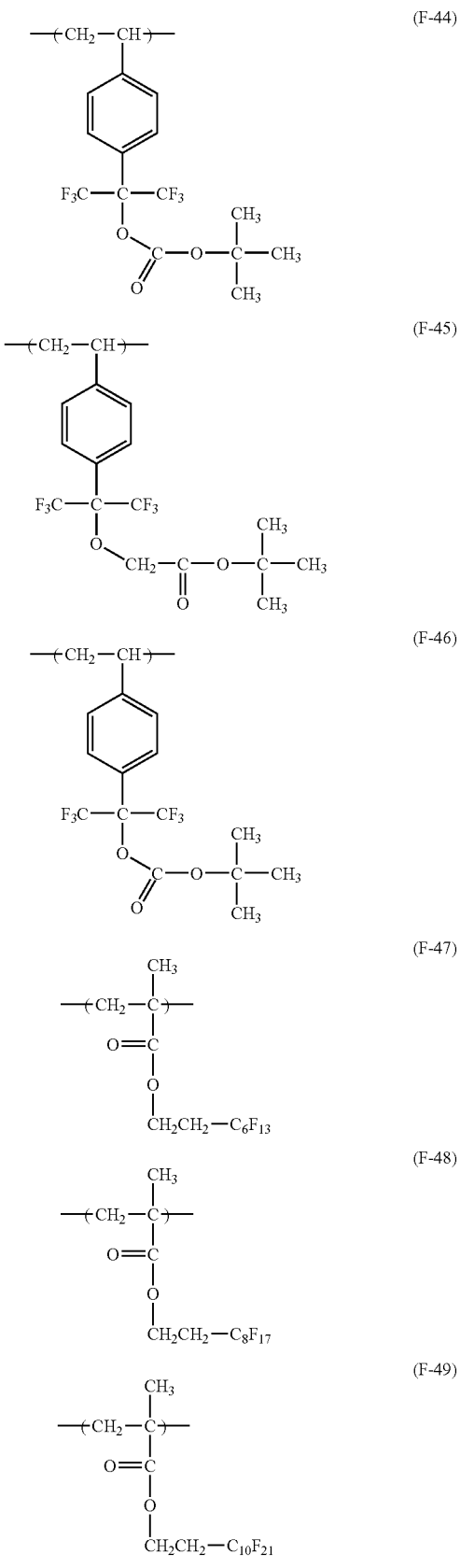

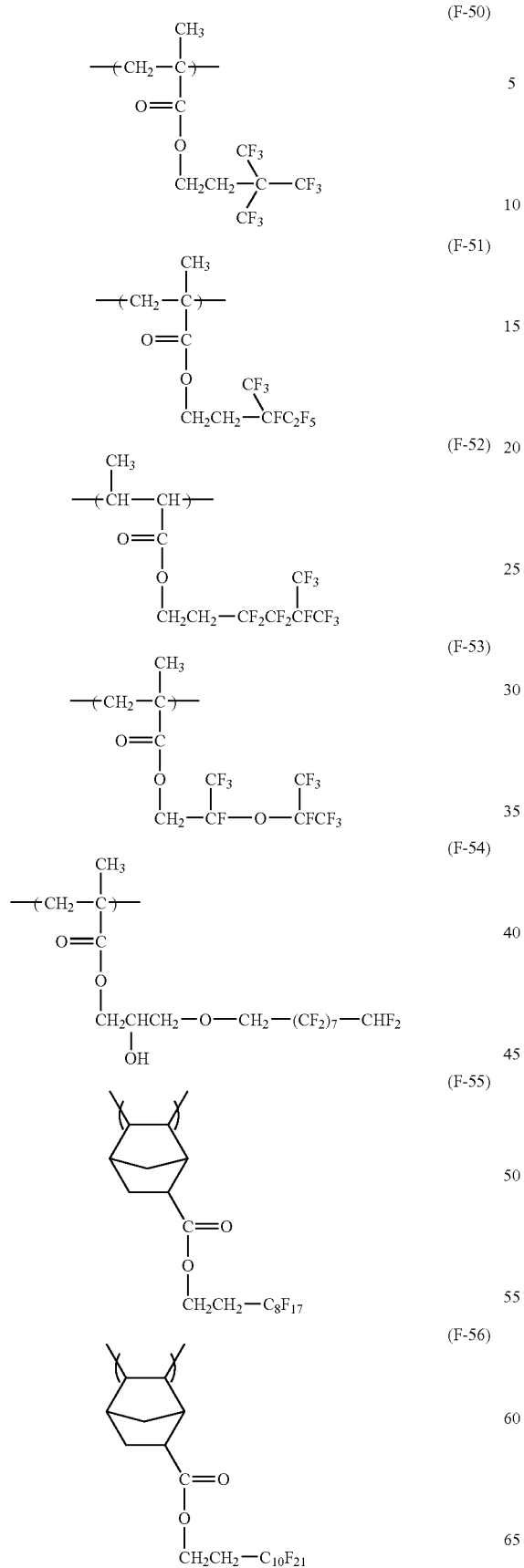

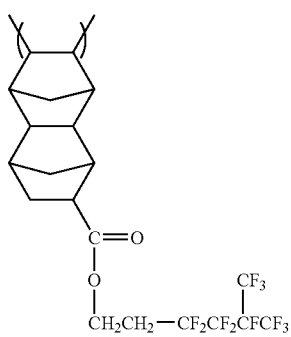
(F-62)

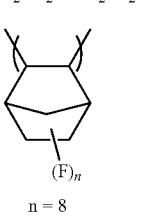
(F-63)

n = 8

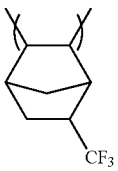
(F-64)

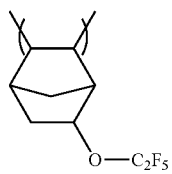
(F-65)

The total content of the repeating units represented by general formulae (FA) to (FG) is generally 10-80% by mole, preferably 30-70% by mole, more preferably 35-65% by mole, based on all repeating units constituting the resin.

The resin (B) according to the invention may contain, besides the repeating structural units described above, units formed by copolymerizing other polymerizable monomers for the purpose of improving the performances of the resist according to the invention.

Examples of usable comonomers include compounds having one addition-polymerizable unsaturated bond other than those mentioned above, which are selected from acrylic esters, acrylamide derivatives, methacrylic esters, methacrylamide derivatives, allyl compounds, vinyl ethers, vinyl esters, styrene and styrene derivatives, and crotonic esters.

From the standpoints of improving dry etching resistance, regulating alkali solubility, improving adhesion to substrates, etc., the fluorine-containing resin described above preferably contains other repeating units derived from one or more comonomers, besides the fluorine atom-containing repeating units described above. Preferred examples of such optional repeating units include the following.

1) Repeating units having an alicyclic hydrocarbon structure represented by any of general formulae (pI) to (pVI) and (II-AB). Specifically, repeating units 1 to 23 shown above and repeating units [II-1] to [II-32] shown above. Preferred are the repeating unit examples 1 to 23 in which Rx is $CF_3$.

2) Repeating units having a lactone structure represented by any of general formulae (Lc) and (V-1) to (V-5). Specifically, the repeating units shown above as examples, in particular, those repeating units shown above as examples which have a group represented by any of general formulae (Lc) and (V-1) to (V-4).

3) Repeating units represented by any of the following general formulae (XV), (XVI), and (XVII), which are derived from maleic anhydride, a vinyl ether, or a vinyl compound having a cyano group; specifically, repeating units (C-1) to (C-15) shown below. These optional repeating units may contain one or more fluorine atoms or contain no fluorine atom.

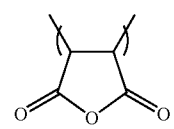
(XV)

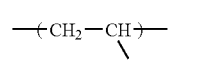
(XVI)

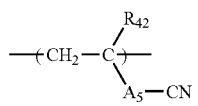
(XVII)

In the formulae, $R_{41}$ represents an alkyl, cycloalkyl, aralkyl, or aryl group. The alkyl group represented by $R_{41}$ may have been substituted by an aryl group.

$R_{42}$ represents a hydrogen atom, halogen atom, cyano, or alkyl group.

$A_5$ represents a single bond, divalent alkylene, alkenylene, cycloalkylene, or arylene group, —O—CO—$R_{22}$—, —CO—O—$R_{23}$—, or —CO—N($R_{24}$)—$R_{25}$—.

$R_{22}$, $R_{23}$, and $R_{25}$ may be the same or different, and each represent a single bond or a divalent alkylene, alkenylene, cycloalkylene, or arylene group which may have an ether, ester, amide, urethane, or ureido group.

$R_{24}$ represents a hydrogen atom or an alkyl, cycloalkyl, aralkyl, or aryl group.

Examples of these substituents are the same as those enumerated above as examples of the substituents in general formulae (FA) to (FG).

Specific examples of the repeating structural units represented by general formulae (XV) to (XVII) are shown below, but the units in the invention should not be construed as being limited to these.

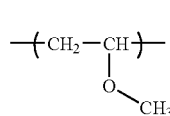
(C-1)

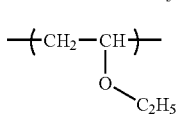
(C-2)

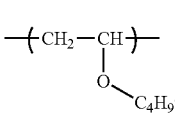
(C-3)

The total amount of the repeating units represented by general formulae (XV) to (XVII) and the other repeating units in the resin to be used is generally 0-70% by mole, preferably 10-60% by mole, more preferably 20-50% by mole, based on all repeating units constituting the resin.

In the fluorine group-containing resin as the acid-decomposable resin (B), acid-dissociable groups may be contained in any repeating units.

The content of the repeating units each containing an acid-dissociable group is preferably 10-70% by mole, more preferably 20-60% by mole, even more preferably 30-60% by mole, based on all repeating units.

The fluorine group-containing resin can be synthesized by radical polymerization in almost the same manner as for the alicyclic-hydrocarbon-based acid-decomposable resin.

The weight-average molecular weight of the resin as ingredient (B) in the invention is preferably 1,000-200,000 in terms of weight-average molecular weight determined through measurement by GPC and calculation for standard polystyrene. By regulating the weight-average molecular weight of the resin to 1,000 or higher, heat resistance and dry etching resistance can be improved. By regulating the weight-average molecular weight thereof to 200,000 or lower, not only developability can be improved but also film-forming properties can be improved because of a considerably reduced viscosity.

In the positive type photosensitive composition of the invention, the amount of the resin incorporated as ingredient (B) according to the invention is preferably 40-99.99% by mass, more preferably 50-99.97% by mass, based on all solid components of the whole composition.

[3] (C) Dissolution Inhibitive Compound Having Molecular Weight of 3,000 or Lower and Decomposing by Action of Acid to Increase its Solubility in Alkaline developer (Hereinafter Referred to Also as "Ingredient (C)" or "Dissolution Inhibitive Compound")

The dissolution inhibitive compound as ingredient (C), which has a molecular weight of 3,000 or lower and decomposes by the action of an acid to increase a solubility of the dissolution inhibitive compound in an alkaline developer, preferably is an alicyclic or aliphatic compound having an acid-dissociable group, such as the cholic acid derivatives containing an acid-dissociable group which are described in *Proceeding of SPIE*, 2724, 355 (1996), so as not to reduce transmission at wavelengths of 220 nm and shorter. Examples of the acid-dissociable group and alicyclic structure are the same as those described above with regard to the alicyclic-hydrocarbon-based acid-decomposable resin.

In the case where the photosensitive composition of the invention is to be exposed with a KrF excimer laser or irradiated with electron beams, the dissolution inhibitive compound preferably is one containing a structure formed by replacing one or more of the phenolic hydroxy group(s) of a phenol compound by an acid-dissociable group. The phenol compound preferably is one having 1-9 phenol frameworks, and more preferably is one having 2-6 phenol frameworks.

The molecular weight of the dissolution inhibitive compound in the invention is 3,000 or lower, preferably 300-3,000, more preferably 500-2,500.

The amount of the dissolution inhibitive compound to be added is preferably 3-50% by mass, more preferably 5-40% by mass, based on the solid components of the photosensitive composition.

Examples of the dissolution inhibitive compound are shown below, but the compound in the invention should not be construed as being limited to the following examples.

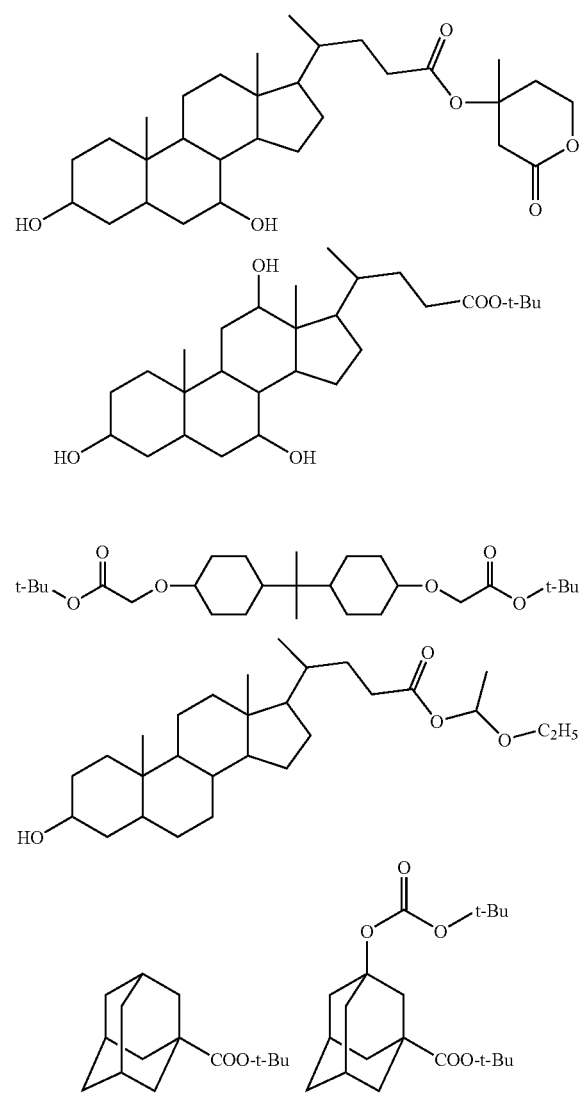

-continued

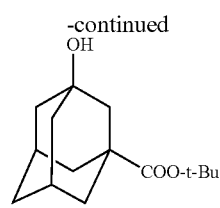

[4] (D) Resin Soluble in Alkaline developer (Hereinafter Referred to Also as "Ingredient (D)" or "Alkali-Soluble Resin")

The rate of alkali dissolution of these alkali-soluble resins is preferably 20 Å/sec or higher, especially preferably 200 Å/sec or higher (Å is angstrom), as measured in 0.261-N tetramethylammonium hydroxide (TMAH) (23° C.).

Examples of the alkali-soluble resin to be used in the invention include novolak resins, hydrogenated novolak resins, acetone/pyrogallol resins, poly(o-hydroxystyrene), poly(m-hydroxystyrene), poly(p-hydroxystyrene), hydrogenated poly(hydroxystyrene), halogen- or alkyl-substituted poly(hydroxystyrene), hydroxystyrene/N-substituted maleimide copolymers, o/p- and m/p-hydroxystyrene copolymers, polyhydroxystyrenes partly O-alkylated at the hydroxy groups (e.g., O-methylated, O-(1-methoxy)ethylated, O-(1-ethoxy) ethylated, O-2-tetrahydropyranyl-substituted, and O-(t-butoxycarbonyl)methylated polyhydroxystyrenes having a degree of alkylation of 5-30% by mole), polyhydroxystyenes partly O-acylated at the hydroxy groups (e.g., O-acetylated and O-(t-butoxy)carbonylated polyhydroxystyrenes having a degree of acylation of 5-30% by mole), styrene/maleic anhydride copolymers, styrene/hydroxystyrene copolymers, α-methylstyrene/hydroxystyrene copolymers, carboxyl-containing methacrylic resins and derivatives thereof, and poly(vinyl alcohol) derivatives. However, the alkali-soluble resin should not be construed as being limited to these examples.

Especially preferred alkali-soluble resins are novolak resins, poly(o-hydroxystyrene), poly(m-hydroxystyrene), poly(p-hydroxystyrene), copolymers of these, alkyl-substituted poly(hydroxystyrene)s, partly O-alkylated or O-acylated poly(hydroxystyrene)s, styrene/hydroxystyrene copolymers, and α-methylstyrene/hydroxystyrene copolymers.

The novolak resins can be obtained by subjecting one or more given monomers as a major ingredient to addition condensation with an aldehyde in the presence of an acid catalyst.

The weight-average molecular weight of the alkali-soluble resin is generally 2,000 or higher, preferably 5,000-200,000, more preferably 5,000-100,000.

Weight-average molecular weight herein is defined as a value determined through measurement by gel permeation chromatography and calculation for standard polystyrene.

Those alkali-soluble resins (D) in the invention may be used in combination of two or more thereof.

The amount of the alkali-soluble resin to be used is generally 40-97% by mass, preferably 60-90% by mass, based on the solid components of the whole photosensitive composition.

[5] (E) Acid-Sensitive Crosslinking Agent which Crosslinks the Alkali-Soluble Resin by Action of Acid (Hereinafter Referred to Also as "Ingredient (E)" or "Crosslinking Agent")

A crosslinking agent is used in the negative type photosensitive composition of the invention.

The crosslinking agent may be any compound which, by the action of an acid, crosslinks the resin soluble in an alkaline developer. However, the following (1) to (3) are preferred.

(1) Hydroxymethylated, alkoxymethylated, or acyloxymethylated phenol derivatives.
(2) Compounds having N-hydroxymethyl, N-alkoxymethyl, or N-acyloxymethyl groups.
(3) Compounds having epoxy groups.

The alkoxymethyl groups each preferably have up to 6 carbon atoms, and the acyloxymethyl groups each preferably have up to 6 carbon atoms.

Especially preferred examples of those crosslinking agents are shown below.

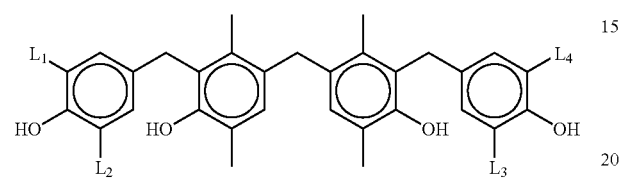

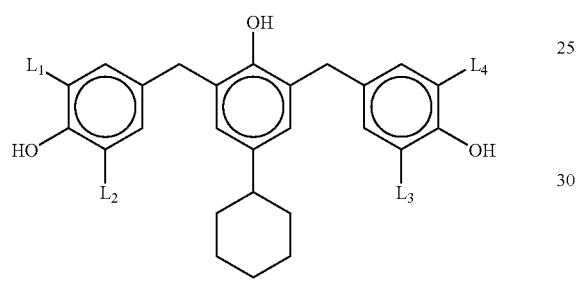

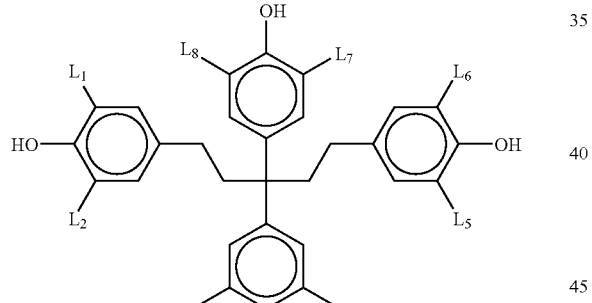

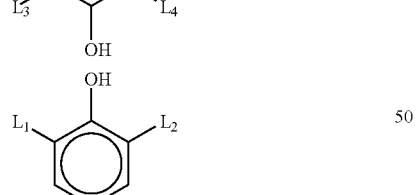

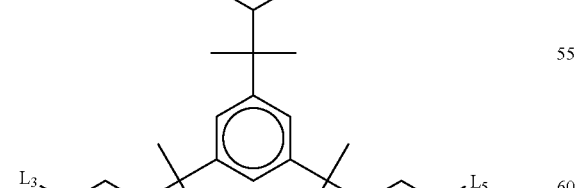

-continued

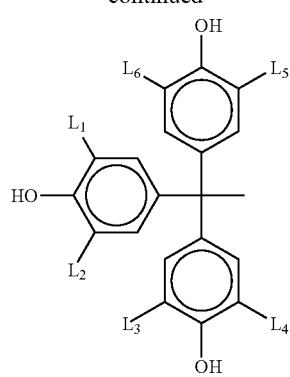

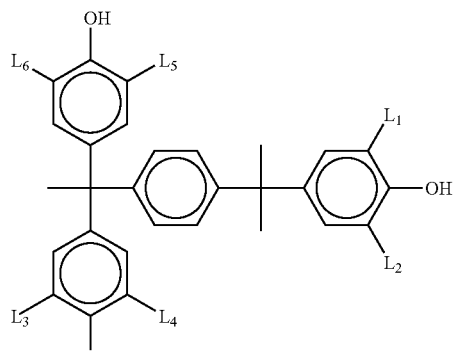

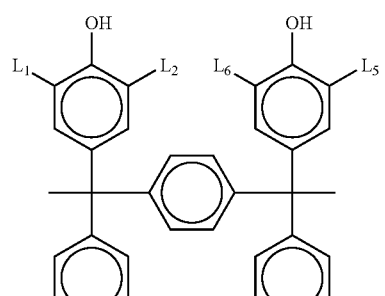

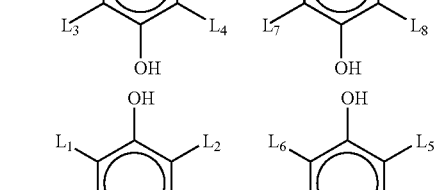

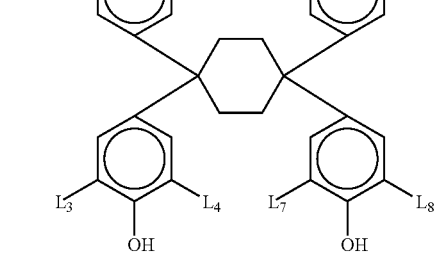

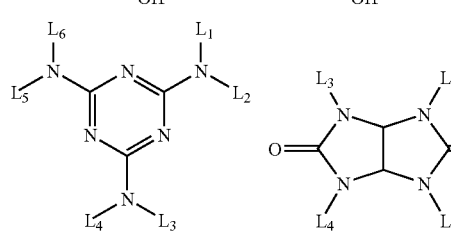

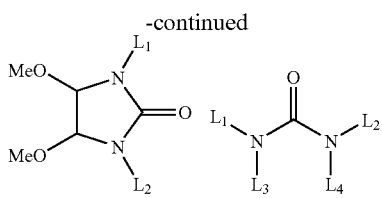

In the formulae, $L^1$ to $L^8$ may be the same or different and each represent a hydrogen atom, hydroxymethyl, methoxymethyl, ethoxymethyl, or alkyl group having 1-6 carbon atoms.

The crosslinking agent is used in an amount of generally 3-70% by mass, preferably 5-50% by mass, based on the solid components of the photosensitive composition.

<Other Ingredients>

[6] (F) Basic Compound

It is preferred that the photosensitive composition of the invention should contain a basic compound (F) so as to be reduced in performance changes with the lapse of time from exposure to heating.

Preferred examples thereof include structures represented by the following formulae (A) to (E).

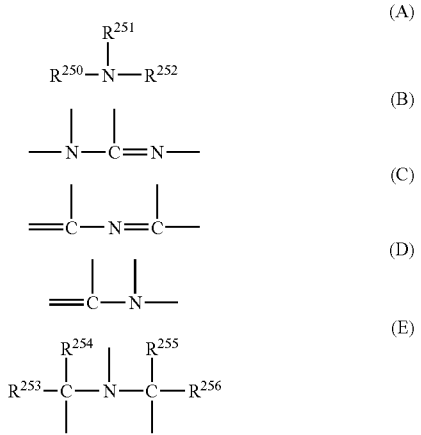

In formula (A), $R^{250}$, $R^{251}$, and $R^{252}$ each independently are a hydrogen atom, an alkyl group having 1-20 carbon atoms, a cycloalkyl group having 3-20 carbon atoms, or an aryl group having 6-20 carbon atoms, provided that $R^{250}$ and $R^{251}$ may be bonded to each other to form a ring. These groups may have one or more substituents. The alkyl or cycloalkyl group having one or more substituents preferably is an aminoalkyl group having 1-20 carbon atoms, aminocycloalkyl group having 3-20 carbon atoms, hydroxyalkyl group having 1-20 carbon atoms, or hydroxycycloalkyl group having 3-20 carbon atoms.

Those alkyl groups each may contain an oxygen, sulfur, or nitrogen atom in the alkyl chain.

In formula (E), $R^{253}$, $R^{254}$, $R^{255}$, and $R^{256}$ each independently represents an alkyl group having 1-6 carbon atoms or a cycloalkyl group having 3-6 carbon atoms.

Preferred compounds include guanidine, aminopyrrolidine, pyrazole, pyrazoline, piperazine, aminomorpholine, aminoalkylmorpholines, and piperidine, which each may having one or more substituents. More preferred compounds include compounds having an imidazole structure, diazabicyclo structure, onium hydroxide structure, onium carboxylate structure, trialkylamine structure, aniline structure, or pyridine structure, alkylamine derivatives having a hydroxy group and/or ether bond, and aniline derivatives having a hydroxy group and/or ether bond.

Examples of the compounds having an imidazole structure include imidazole, 2,4,5-triphenylimidazole, and benzimidazole. Examples of the compounds having a diazabicyclo structure include 1,4-diazabicyclo[2.2.2]octane, 1,5-diazabicyclo[4.3.0]non-5-ene, and 1,8-diazabicyclo[5.4.0]undec-7-ene. Examples of the compounds having an onium hydroxide structure include triarylsulfonium hydroxides, phenacylsulfonium hydroxide, and sulfonium hydroxides having a 2-oxoalkyl group, and specific examples thereof include triphenylsulfonium hydroxide, tris(t-butylphenyl)sulfonium hydroxide, bis(t-butylphenyl)iodonium hydroxide, phenacylthiophenium hydroxide, and 2-oxopropylthiophenium hydroxide. The compounds having an onium carboxylate structure are those compounds having an onium hydroxide structure in which the anion part has been replaced by a carboxylate, and examples thereof include acetates, adamantane-1-carboxylates, and perfluoroalkylcarboxylates. Examples of the compounds having a trialkylamine structure include tri(n-butyl)amine and tri(n-octyl)amine. Examples of the aniline compounds include 2,6-diisopropylaniline and N,N-dimethylaniline. Examples of the alkylamine derivatives having a hydroxy group and/or ether bond include ethanolamine, diethanolamine, triethanolamine, and tris(methoxyethoxyethyl)amine. Examples of the aniline derivatives having a hydroxy group and/or ether bond include N,N-bis(hydroxyethyl)aniline.

Those basic compounds may be used alone or in combination of two or more thereof. The amount of the basic compounds to be used is generally 0.001-10% by mass, preferably 0.01-5% by mass, based on the solid components of the photosensitive composition. From the standpoint of sufficiently obtaining the effect of the addition, the amount of the compounds is preferably 0.001% by mass or larger. From the standpoints of sensitivity and the developability of unexposed areas, the amount of the compounds is preferably 10% by mass or smaller.

[7] (G) Fluorochemical and/or Silicone Surfactant

The photosensitive composition of the invention preferably further contains any one of or two or more of fluorochemical and/or silicone surfactants (fluorochemical surfactants, silicone surfactants, and surfactants containing both fluorine atoms and silicon atoms).

When the photosensitive composition of the invention contains a fluorochemical and/or silicone surfactant, it can show satisfactory sensitivity and resolution when irradiated with an exposure light having a wavelength of 250 nm or shorter, especially 220 nm or shorter, and give a resist pattern having satisfactory adhesion and reduced in development defects.

Examples of the fluorochemical and/or silicone surfactants include the surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, and JP-A-2002-277862, and U.S. Pat. Nos. 5,405,720, 5,360,692, 5,529,881, 5,296,330, 5,436,098, 5,576,143, 5,294,511, and 5,824,451. It is also possible to use the following commercial surfactants as they are.

Examples of usable commercial surfactants include fluorochemical or silicone surfactants such as F-Top EF301 and FE303 (manufactured by New Akita Chemical Company), Fluorad FC430 and 431 (manufactured by Sumitomo 3M Ltd.), Megafac F171, F173, F176, F189, and R08 (manufactured by Dainippon Ink & Chemicals, Inc.), Surflon S-382 and SC101, 102, 103, 104, 105, and 106 (manufactured by Asahi Glass Co., Ltd.), and Troysol S-366 (manufactured by Troy Chemical Co., Ltd.). Polysiloxane polymer KP-341 (manufactured by Shin-Etsu Chemical Co., Ltd.) can also be used as a silicone surfactant.

Also usable besides the known surfactants shown above is a surfactant comprising a polymer having a fluoroaliphatic group and derived from a fluoroaliphatic compound produced by the telomerization method (also called telomer method) or oligomerization method (also called oligomer method). The fluoroaliphatic compound can be synthesized by the method described in JP-A-2002-90991.

The polymer having a fluoroaliphatic group preferably is a copolymer of a monomer having a fluoroaliphatic group with a poly(oxyalkylene) acrylate and/or a poly(oxyalkylene) methacrylate. This copolymer may be one in which the monomer units are randomly distributed or be a block copolymer. Examples of the poly(oxyalkylene) group include poly(oxyethylene), poly(oxypropylene), and poly(oxybutylene). The poly(oxyalkylene) group may be a unit having, in the same chain, alkylenes having different chain lengths, such as a poly(blocks of oxyethylene, oxypropylene, and oxyethylene) or poly(blocks of oxyethylene and oxypropylene) group. The copolymer of a monomer having a fluoroaliphatic group with a poly(oxyalkylene) acrylate (or methacrylate) is not limited to binary copolymers, and may be a copolymer of three or more monomers which is obtained by copolymerization in which two or more different monomers each having a fluoroaliphatic group, two or more different poly(oxyalkylene) acrylates (or methacrylates), etc. are simultaneously copolymerized.

Examples of commercial surfactants include Megafac F178, F-470, F-473, F-475, F-476, and F-472 (manufactured by Dainippon Ink & Chemicals, Inc.). Examples of the polymer having a fluoroaliphatic group further include a copolymer of an acrylate (or methacrylate) having a $C_6F_{13}$ group with a poly(oxyalkylene) acrylate (or methacrylate), a copolymer of an acrylate (or methacrylate) having a $C_6F_{13}$ group with poly(oxyethylene) acrylate (or methacrylate) and poly(oxypropylene) acrylate (or methacrylate), a copolymer of an acrylate (or methacrylate) having a $C_8F_{17}$ group with a poly(oxyalkylene) acrylate (or methacrylate), and a copolymer of an acrylate (or methacrylate) having a $C_8F_{17}$ group with poly(oxyethylene) acrylate (or methacrylate) and poly (oxypropylene) acrylate (or methacrylate).

The amount of the fluorochemical and/or silicone surfactant to be used is preferably 0.0001-2% by mass, more preferably 0.001-1% by mass, based on the total amount of the photosensitive composition (excluding the solvent).

[8] (H) Organic Solvent

The photosensitive composition of the invention to be used is prepared by dissolving the ingredients in a given organic solvent.

Examples of usable organic solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydro furan.

In the invention, organic solvents may be used alone or as a mixture of two or more thereof. It is, however, preferred to use a mixed solvent prepared by mixing at least one solvent containing one or more hydroxy groups in the structure with at least one solvent containing no hydroxy group. Use of this mixed solvent is effective in diminishing particle generation during resist fluid storage.

Examples of the solvent containing one or more hydroxy groups include ethylene glycol, ethylene glycol monomethyl ether, ethylene glycol monoethyl ether, propylene glycol, propylene glycol monomethyl ether, propylene glycol monoethyl ether, and ethyl lactate. Preferred of these are propylene glycol monomethyl ether and ethyl lactate.

Examples of the solvent containing no hydroxy group include propylene glycol monomethyl ether acetate, ethyl ethoxypropionate, 2-heptanone, γ-butyrolactone, cyclohexanone, butyl acetate, N-methylpyrrolidone, N,N-dimethylacetamide, and dimethyl sulfoxide. Especially preferred of these are propylene glycol monomethyl ether acetate, ethyl ethoxypropionate, 2-heptanone, γ-butyrolactone, cyclohexanone, and butyl acetate. Most preferred are propylene glycol monomethyl ether acetate, ethyl ethoxypropionate, and 2-heptanone.

The proportion (by mass) of the solvent containing one or more hydroxy groups to the solvent containing no hydroxy group is generally from 1/99 to 99/1, preferably from 10/90 to 90/10, more preferably from 20/80 to 60/40. A mixed solvent in which the content of the solvent containing no hydroxy group is 50% by mass or higher is especially preferred from the standpoint of evenness of application.

<Other Additives>

A dye, plasticizer, surfactant other than ingredient (G) described above, photosensitizer, compound accelerating dissolution in developing solutions, and other additives may be further incorporated into the photosensitive composition of the invention according to need.

The compound accelerating dissolution in developing solutions which is usable in the invention is a low-molecular compound having a molecular weight of 1,000 or lower and having two or more phenolic OH groups or one or more carboxy groups. In the case where the compound has one or more carboxy groups, it preferably is an alicyclic or aliphatic compound.

The amount of such dissolution-accelerating compounds to be added is preferably 2-50% by mass, more preferably 5-30% by mass, based on the resin as ingredient (B) or the resin as ingredient (D). From the standpoints of diminishing development residues and preventing pattern deformation during development, the amount thereof is preferably 50% by mass or smaller.

The phenolic compound having a molecular weight of 1,000 or lower can be easily synthesized by persons skilled in the art while referring to methods described in, e.g., JP-A-4-122938, JP-A-2-28531, U.S. Pat. No. 4,916,210, and European Patent 219,294.

Examples of the alicyclic or aliphatic compound having one or more carboxyl groups include carboxylic acid derivatives having a steroid structure, such as cholic acid, deoxycholic acid, and lithocholic acid, adamantanecarboxylic acid derivatives, adamantanedicarboxylic acid, cyclohexanecarboxylic acid, and cyclohexanedicarboxylic acid. However, the alicyclic or aliphatic compound should not be construed as being limited to these.

Surfactants other than the fluorochemical and/or silicone surfactant (G) described above may be added in the invention. Examples thereof include nonionic surfactants such as polyoxyethylene alkyl ethers, polyoxyethylene alkylaryl ethers, polyoxyethylene/polyoxypropylene block copolymers, aliphatic esters of sorbitan, and aliphatic esters of polyoxyethylene-sorbitan.

Those surfactants may be used alone or in combination of two or more thereof.

(Method of Use)

When the photosensitive composition of the invention is used, the ingredients described above are dissolved in a given organic solvent, preferably the mixed solvent described above, and the resultant solution is applied to a given substrate in the following manner.

For example, the photosensitive composition is applied to a base such as one for use in producing precision integrated-circuit elements (e.g., a silicon base coated with silicon dioxide) by an appropriate coating technique using a spinner, coater, or the like and then dried to form a photosensitive film.

This photosensitive film is irradiated with an actinic ray or a radiation through a given mask and is preferably baked (heated). Thereafter, the film is developed and rinsed. Thus, a satisfactory pattern can be obtained.

Examples of the an actinic ray or radiation include infrared rays, visible light, ultraviolet rays, far ultraviolet rays, X-rays, and electron beams. Preferred are far ultraviolet rays having a wavelength of preferably 250 nm or shorter, more preferably 220 nm or shorter, such as, e.g., KrF excimer laser light (248 nm), ArF excimer laser light (193 nm), and $F_2$ excimer laser light (157 nm), X-rays, electron beams, and the like. In particular, ArF excimer laser light, $F_2$ excimer laser light, EUV (13 nm), and electron beams are preferred.

In the development step, an alkaline developer is used in the following manner. As an alkaline developer for the resist composition can be used an alkaline aqueous solution of, e.g., an inorganic alkali such as sodium hydroxide, potassium hydroxide, sodium carbonate, sodium silicate, sodium metasilicate, or ammonia water, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, or a cyclic amine such as pyrrole or piperidine.

It is also possible to add an alcohol or a surfactant in an appropriate amount to the alkaline developer to be used.

The alkali concentration of the alkaline developer is generally 0.1-20% by mass.

The pH of the alkaline developer is generally 10.0-15.0.

EXAMPLES

The invention will be explained below in more detail by reference to Examples, but the contents of the invention should not be construed as being limited by the following Examples.

(Synthesis of Compound I-1)

I-1: Triphenylsulfonium 1,1,2,2,3,3-hexafluoro-3-(piperidine-1-sulfonyl)propane-1-sulfonate A solution prepared by mixing 1.08 g (12.6 mmol) of piperidine with 15 mL of diisopropyl ether was added dropwise over 30 minutes to a mixture of 4.0 g (12.65 mmol) of 1,1,2,2,3,3-hexafluoropropane-1,3-disulfonyl difluoride, 2.56 g (25.3 mmol) of triethylamine, and 30 mL of diisopropyl ether with cooling with ice in a nitrogen stream. The resultant mixture was stirred for 1 hour with cooling with ice and then further stirred at room temperature for 1 hour. The organic layer was washed successively with water, saturated aqueous ammonium chloride solution, and water and then dried with sodium sulfate. The solvent was removed, and 20 mL of ethanol and 200 mg of sodium hydroxide were added to the residue. This mixture was stirred at room temperature for 2 hours. Dilute hydrochloride acid was added thereto. The resultant reaction mixture was neutralized to obtain an ethanol solution of the sulfonic acid represented by the following formula.

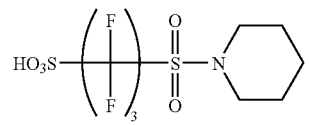

A solution of triphenylsulfonium acetate was added to the sulfonic acid solution, and this mixture was stirred at room temperature for 2 hours. Thereto was added 300 mL of chloroform. The organic layer was washed successively with water, saturated aqueous ammonium chloride solution, and water. The reaction product was purified by column chromatography ($SiO_2$; chloroform/methanol=5/1) to obtain a white solid in an amount of 3.0 g (4.68 mmol).

Meanwhile, the triphenylsulfonium acetate solution was prepared by adding 5.07 g (13 mmol) of triphenylsulfonium iodide, 2.25 g (13.5 mmol) of silver acetate, 120 mL of acetonitrile and 60 mL of water and then stirring the resultant reaction solution for one hour at room temperature, followed by filtration of the solution.

$^1$H-NMR (300 MHz, $CDCl_3$) δ 1.64 (bs, 6H), 3.29 (bs, 2H), 3.64 (bs, 2H), 7.70 (m, 15H)

$^{19}$F-NMR (300 MHz, $CDCl_3$) δ −111.1 (t, 2F), −114.3 (t, 2F), −119.4 (m, 2F)

(Synthesis of Compound I-15)

Under nitrogen gas stream, 4.0 g (12.65 mmol) of 1,1,2,2,3,3-hexafluoropropane-1,3-disulfonyl difluoride, 2.56 g (25.3 mmol) of triethylamine and 40 mL tetrahydrofuran were cooled with ice, and to this mixture a mixed solution of 1.08 g (12.6 mmol) of piperidine and 20 mL of tetrahydrofuran was added dropwise over the period of 30 min. The mixture was stirred for one hour under ice cooling, and then for additional three hours at room temperature. After the addition of ethyl acetate, the organic layer was washed sequentially with water, a saturated ammonium chloride aqueous solution and water, followed by drying with sodium sulfate. Then the solvent was removed, and 20 mL of ethanol and 200 mg of sodium hydroxide were added. The resultant solution was stirred for 2 hours at room temperature. The reaction solution was neutralized by adding dilute hydrochloric acid, added with 3.21 g of 1-(3,3-dimethyl-2-oxobutyl)-tetrahydrothiophenium bromide, and then subjected to 2 hour stirring at room temperature. After the addition of 300 mL of chloroform, the organic layer was washed with water several times, and dried to obtain 2.79 g of the white solid in concern.

$^1$H-NMR (300 MHz, $CDCl_3$) δ 1.245 (s, 9H), 1.658 (bs, 6H), 2.280 (m, 2H), 2.505 (m, 2H), 3.291 (bs, 2H), 3.607 (m, 6H), 5.028 (s, 2H)

$^{19}$F-NMR (300 MHz, $CDCl_3$) δ −111.62 (t, 2F), −114.36 (t, 2F), −119.43 (s, 2F)

(Synthesis of Compound I-46)

Under nitrogen gas stream, 4.0 g (12.65 mmol) of 1,1,2,2,3,3-hexafluoropropane-1,3-disulfonyl difluoride, 2.56 g (25.3 mmol) of triethylamine and 40 mL of tetrahydrofuran were cooled with ice, and to this mixture a mixed solution of 1.04 g (11.9 mmol) of morpholine and 20 mL of tetrahydrofuran was added dropwise over the period of 30 min. The mixture was stirred for one hour under ice cooling, and then for additional three hours at room temperature. After the addition of ethyl acetate, the organic layer was washed sequentially with water, a saturated ammonium chloride aqueous solution and water, followed by drying with sodium sulfate. Then the solvent was removed, and 20 mL of ethanol and 600 mg of sodium hydroxide were added. The resultant solution was stirred for 2 hours at room temperature. The reaction solution was neutralized by adding dilute hydrochloric acid, added with 4.09 g of triphenylsulfonium bromide, and then subjected to 2 hour stirring at room temperature. After the addition of 300 mL chloroform, the organic layer was washed with water several times, and dried to obtain 6.0 g of the white solid in concern.

$^1$H-NMR (300 MHz, CDCl$_3$) δ 3.54 (bs, 4H), 3.74 (bs, 4H), 7.657-7.773 (m, 15H), $^{19}$F-NMR (300 MHz, CDCl$_3$) δ −110.74 (m, 2F), −114.33 (t, 2F), −119.32 (s, 2F)

(Synthesis of Compound I-85)

Under nitrogen gas stream, 10.0 g (31.6 mmol) of 1,1,2,2,3,3-hexafluoropropane-1,3-disulfonyl difluoride, 3.2 g (31.6 mmol) of triethylamine and 100 mL of tetrahydrofuran were cooled with ice, and to this mixture a mixed solution of 5.8 g (31.6 mmol) of N,N-diethylnipecotamide and 80 mL of tetrahydrofuran was added dropwise over the period of 30 min. The mixture was stirred for one hour under ice cooling, and then for additional three hours at room temperature. After the addition of ethyl acetate, the organic layer was washed sequentially with water, a saturated ammonium chloride aqueous solution and water, followed by drying with sodium sulfate. Then the solvent was removed, and 100 mL of methanol and 1600 mg of sodium hydroxide were added. The resultant solution was stirred for 2 hours at room temperature. The reaction solution was neutralized by adding dilute hydrochloric acid, added with 9.76 g triphenylsulfonium bromide, and then subjected to 2 hour stirring at room temperature. After the addition of 300 mL of chloroform, the organic layer was washed with water several times, and dried to obtain 16.0 g of the colorless oil in concern.

$^1$H-NMR (300 MHz, CDCl$_3$) δ 1.09 (q, 3H), 1.20 (q, 3H) 1.59-1.92 (m, 4H), 2.70 (t, 1H), 3.05 (t, 1H), 3.25 (t, 1H), 3.34 (m, 4H), 3.95 (t, 2H), 7.67-7.78 (m, 15H)

$^{19}$F-NMR (300 MHz, CDCl$_3$) δ −110.54, −111.91 (m, 2F), −113.99 (m, 2F), −118.45, −119.37 (m, 2F)

(Synthesis of Compound I-89)

Under nitrogen gas stream, 4.0 g (12.65 mmol) of 1,1,2,2,3,3-hexafluoropropane-1,3-disulfonyl difluoride, 2.56 g (25.3 mmol) of triethylamine and 40 mL of tetrahydrofuran were cooled with ice, and to this mixture a mixed solution of 2.10 g (11.9 mmol) of 4-cyclohexylphenol and 20 mL of tetrahydrofuran was added dropwise over the period of 30 min. The mixture was stirred for one hour under ice cooling, and then for additional three hours at room temperature. After the addition of ethyl acetate, the organic layer was washed sequentially with water, a saturated ammonium chloride aqueous solution and water, followed by drying with sodium sulfate. Then the solvent was removed, and 20 mL of ethanol and 200 mg of sodium hydroxide were added. The resultant solution was stirred for 2 hours at room temperature. The reaction solution was neutralized by adding dilute hydrochloric acid, added with 4.09 g of triphenylsulfonium bromide, and then subjected to 2 hour stirring at room temperature. After the addition of 300 mL of chloroform, the organic layer was washed with water several times. By purifying by means of column chromatography (SiO$_2$, chloroform/methanol=5/1), 6.65 g of the white solid in concern was obtained.

$^1$H-NMR (300 MHz, CDCl$_3$) δ 1.256-1.607 (m, 5H), 1.724-1.856 (m, 5H), 2.505 (m, 1H), 7.193 (AB quartet, 4H), 7.657-7.773 (m, 15H)

$^{19}$F-NMR (300 MHz, CDCl$_3$) δ −107.78 (m, 2F), −114.33 (t, 2F), −118.73 (s, 2F)

(Synthesis of Compound I-90)

Under nitrogen gas stream, 4.0 g (12.65 mmol) of 1,1,2,2,3,3-hexafluoropropane-1,3-disulfonyl difluoride, 2.56 g (25.3 mmol) of triethylamine and 40 mL of tetrahydrofuran were cooled with ice, and to this mixture a mixed solution of 3.62 g (11.9 mmol) of 3-n-pentadecylphenol and 20 mL of tetrahydrofuran was added dropwise over the period of 30 min. The mixture was stirred for one hour under ice cooling, and then for additional three hours at room temperature. After the addition of ethyl acetate, the organic layer was washed sequentially with water, a saturated ammonium chloride aqueous solution and water, followed by drying with sodium sulfate. Then the solvent was removed, and 20 mL of ethanol and 200 mg of sodium hydroxide were added. The resultant solution was stirred for 2 hours at room temperature. The reaction solution was neutralized by adding dilute hydrochloric acid, added with 4.09 g of triphenylsulfonium bromide, and then subjected to 2 hour stirring at room temperature. After the addition of 300 mL of chloroform, the organic layer was washed with water several times. By purifying by column chromatography (SiO$_2$, chloroform/methanol=5/1), 3.84 g of the white solid in concern was obtained.

$^1$H-NMR (300 MHz, CDCl$_3$) δ 0.876 (t, 3H), 1.253-1.294 (m, 24H), 1.62 (m, 2H), 2.63 (m, 2H), 7.05-7.16 (m, 3H), 7.27 (m, 1H), 7.68-7.75 (m, 15H)

$^{19}$F-NMR (300 MHz, CDCl$_3$) δ −107.55 (m, 2F), −114.01 (m, 2F), 6-118.40 (m, 2F)

(Synthesis of Compound I-93)

Under nitrogen gas stream, 4.0 g (12.65 mmol) of 1,1,2,2,3,3-hexafluoropropane-1,3-disulfonyl difluoride, 2.56 g (25.3 mmol) of triethylamine and 40 mL of tetrahydrofuran were cooled with ice, and to this mixture a mixed solution of 1.35 g (11.9 mmol) of heptamethyleneimine and 20 mL of tetrahydrofuran was added dropwise over the period of 30 min. The mixture was stirred for one hour under ice cooling, and then for additional three hours at room temperature. After the addition of ethyl acetate, the organic layer was washed sequentially with water, saturated ammonium chloride aqueous solution and water, followed by drying with sodium sulfate. Then, the solvent was removed, and 20 mL of ethanol and 600 mg of sodium hydroxide were added. The resultant solution was stirred for 2 hours at room temperature. The reaction solution was neutralized by adding dilute hydrochloric acid, added with 4.09 g of triphenylsulfonium bromide, and then subjected to 2 hour stirring at room temperature. After the addition of 300 mL chloroform, the organic layer was washed with water several times. By purifying by means of column chromatography (SiO$_2$, chloroform/methanol=5/1), 1.10 g of the white solid in concern was obtained.

$^1$H-NMR (300 MHz, CDCl$_3$) δ 1.70 (m, 10H), 3.11 (bs, 2H), 3.82 (bs, 2H), 7.657-7.773 (m, 15H)

$^{19}$F-NMR (300 MHz, CDCl$_3$) δ −109.70 (t, 2F), −114.27 (t, 2F), −119.44 (s, 2F)

Compounds according to the invention which generate an acid represented by general formula (I) or (I') upon irradiation with an actinic ray or a radiation can be synthesized in the same manner as described above.

<Resins (B)>
The structures and molecular weights of the resins (B) used in the Examples are shown below.
| | Molecular Weight |
|---|---|
| (1) 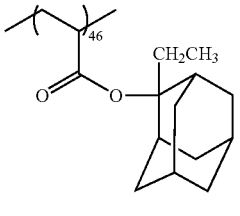 | 10700 |
| (2) 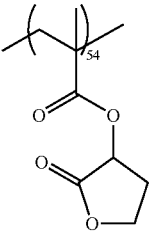 | 9400 |
| (4) 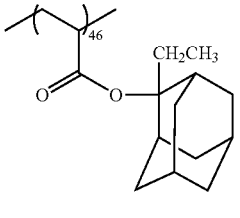 | 10300 |
| (6) 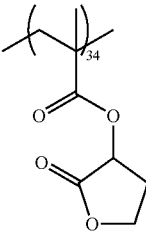 | 11300 |
| (7) 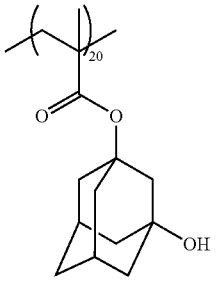 | 8900 |

-continued

| | Molecular Weight |
|---|---|
| (11) | 13400 |
| (15) | 9600 |
| (16) | 5800 |
| (17) | 4700 |
| (20) | 12100 |
| (24) | 10800 |

| | Molecular Weight |
|---|---|
| (25) | 9300 |
| (28) | 7300 |
| (29) | 7600 |
| (30) | 8400 |
| (31) | 6500 |

<Fluorine Group-Containing Resins>

The structures of fluorine group-containing resins (FII-1) to (FII-10), which were used in the Examples, are shown below.

The weight-average molecular weights and other properties of fluorine group-containing resins (FII-1) to (FII-10) are shown in Table 1 below.

TABLE 1

| Resin | Weight-average molecular weight Mw | Dispersity ratio | Content of oligomers having molecular weight of 1,000 or lower (%) |
|---|---|---|---|
| (FII-1) | 15200 | 1.45 | 5 |
| (FII-2) | 24000 | 1.75 | 8 |
| (FII-3) | 18200 | 1.85 | 7 |
| (FII-4) | 16500 | 1.46 | 6 |
| (FII-5) | 9500 | 1.58 | 8 |
| (FII-6) | 19500 | 2.02 | 8 |
| (FII-7) | 6500 | 1.85 | 7 |
| (FII-8) | 28400 | 1.68 | 9 |
| (FII-9) | 28600 | 1.44 | 5 |
| (FII-10) | 12800 | 1.65 | 8 |

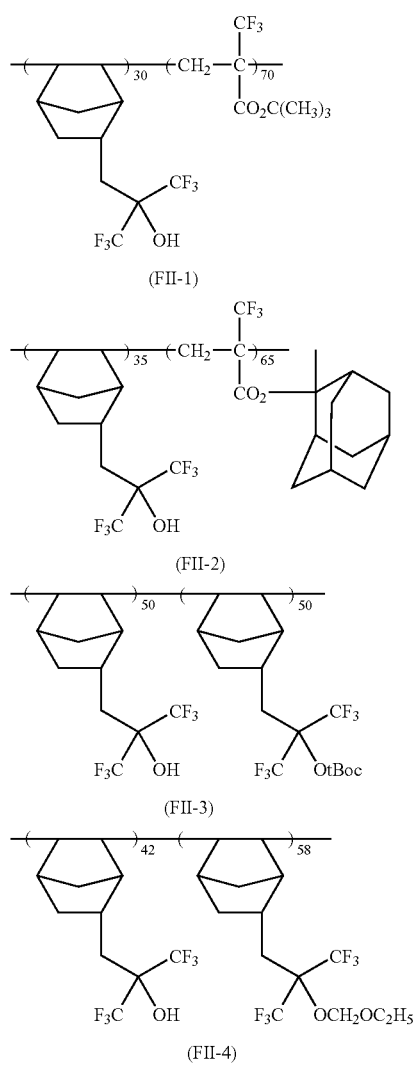

Examples Ar1 to Ar30 and Comparative Example ar1

<Resist Preparation>

Each set of ingredients shown in Table 2 was dissolved in the solvent to prepare a solution having a solid concentration of 12% by mass. This solution was filtered through a 0.1-μm polytetrafluoroethylene filter or polyethylene filter. Thus, positive resist solutions were prepared. The positive resist solutions prepared were evaluated by the methods shown below. The results obtained are shown in Table 2.

<Resist Evaluation>

Antireflection film DUV-42, manufactured by Brewer Science, was applied in an even thickness of 600 Å with a spin coater to a silicon substrate treated with hexamethyldisilazane. The coating was dried at 100° C. for 90 seconds on a hot plate and then dried with heating at 190° C. for 240 seconds. Thereafter, each positive resist solution was applied thereto with a spin coater and dried at 120° C. for 90 seconds to form a 0.30-μm resist film.

This resist film was exposed to light with an ArF excimer laser stepper (manufactured by ISI; NA=0.6) through a mask. Immediately after the exposure, the resist film was heated on a hot plate at 120° C. for 90 seconds. Furthermore, the resist film was developed with a 2.38% by mass aqueous solution of tetramethylammonium hydroxide at 23° C. for 60 seconds, rinsed with pure water for 30 seconds, and then dried to obtain a line pattern.

Method of Evaluation for Pattern Falling:

The exposure amount necessary for reproducing a mask pattern comprising 130-nm lines and spaces in a ratio of 1:1 was taken as the optimal exposure amount. Each resist film was exposed in the optimal exposure amount with respect to dense patterns having a line/space ratio of 1:1. The line width for the finest mask pattern which could be reproduced with satisfactory resolution without causing pattern falling was determined as a threshold pattern-falling line width. The smaller the value of this line width, the finer the pattern which can be reproduced without falling. Namely, smaller values of that line width indicate that pattern falling is less apt to occur.

Method of Evaluation for Line Edge Roughness:

Line edge roughness was examined in the following manner. A 130-nm line/space=1:1 pattern was examined with a length-measuring scanning electron microscope (SEM). In the line pattern, length-direction edges in a range of 5 μm were examined with the length-measuring SEM (S-8840, manufactured by Hitachi, Ltd.) to measure the distance from the standard line where each edge was to be present. This measurement was made on 50 points. A standard deviation was determined and 3σ was calculated. The smaller the value thereof, the better the performance.

TABLE 2

| | | (A) Acid generator (g) | Optional acid generator (g) | (B) Resin (10 g) | Basic compound (g) | Surfactant (g) | Solvent (mass ratio) | Threshold pattern falling line width (nm) | Line edge roughness (nm) |
|---|---|---|---|---|---|---|---|---|---|
| Example | Ar1 | I-1 (0.3) | | (1) | DIA (0.03) | W-4 (0.01) | A1/B1 = 70/30 | 93 | 6.3 |
| | Ar2 | I-1 (0.2) | z58 (0.2) | (4) | TPA (0.03) | W-2 (0.02) | A1/A3 = 40/60 | 97 | 6.1 |
| | Ar3 | I-2 (0.2) | z6 (0.2) | (6) | HAP (0.02) | W-1 (0.01) | A1/B1 = 50/50 | 93 | 6.0 |
| | Ar4 | I-5 (0.3) | z56 (0.1) | (6) | DIA (0.03) | W-4 (0.01) | A1/B1 = 60/40 | 94 | 5.9 |
| | Ar5 | I-1 (0.4) | z12 (0.05) | (7) | PEA (0.01) | W-4 (0.01) | A1/B1 = 60/40 | 89 | 5.2 |
| | Ar6 | I-2 (0.2) I-9 (0.2) | z36 (0.1) | (7) | DIA (0.02) PEA (0.02) | W-4 (0.01) | A1/A3 = 60/40 | 90 | 5.0 |
| | Ar7 | I-14 (0.3) | z40 (0.1) | (15) | TMEA (0.03) | W-3 (0.03) | A1/B2 = 80/20 | 97 | 6.4 |
| | Ar8 | I-22 (0.6) | z41 (0.3) | (16) | TBAH (0.04) | W-1 (0.005) | A2/B1 = 80/20 | 96 | 6.7 |
| | Ar9 | I-35 (0.5) | z42 (0.3) | (17) | HEP (0.03) | W-3 (0.02) | A3/B1 = 70/30 | 99 | 6.1 |
| | Ar10 | I-56 (0.3) | z14 (0.1) | (24) | TPSA (0.05) | W-3 (0.01) | A1/A3 = 60/40 | 95 | 6.5 |
| | Ar11 | I-61 (0.3) | z25 (0.4) | (25) | DCMA (0.03) | W-4 (0.01) | A1/A3 = 60/40 | 96 | 6.8 |
| | Ar12 | I-3 (0.3) | | (28) | DIA (0.03) | W-4 (0.01) | A1/B1 = 60/40 | 89 | 4.9 |
| | Ar13 | I-17 (0.7) | z59 (0.1) | (29) | PEA (0.04) | W-2 (0.02) | A1/A3 = 60/40 | 90 | 5.0 |
| | Ar14 | I-21 (0.4) | z55 (0.2) | (30) | PEA (0.04) | W-4 (0.01) | A1/A3 = 60/40 | 92 | 5.2 |
| | Ar15 | I-26 (0.1) | z14 (0.3) | (31) | DIA (0.03) | W-2 (0.02) | A1/A3 = 60/40 | 91 | 4.9 |
| | Ar16 | I-27 (0.2) | z14 (0.2) | (6) | DIA (0.03) | W-2 (0.01) | A1/A3 = 60/40 | 90 | 4.8 |
| | Ar17 | I-2 (0.15) | z50 (0.2) | (7) | DIA (0.02) | W-4 (0.01) | A1/A3 = 60/40 | 90 | 5.0 |
| | Ar18 | I-1 (0.4) | z4 (0.02) | (28) | PEA (0.02) | W-4 (0.01) | A1/B1 = 60/40 | 89 | 5.1 |
| | Ar19 | I-23 (0.1) I-50 (0.2) | z6 (0.1) z1 (0.1) | (28) 5 g (20) 5 g | DIA (0.02) DCMA (0.02) | W-4 (0.01) | A1/A3 = 60/40 | 89 | 5.0 |
| | Ar20 | I-45 (0.5) I-6 (0.1) | z14 (0.1) | (4) 5 g (7) 5 g | TPA (0.02) PEA (0.02) | W-4 (0.01) | A1/B1 = 60/40 | 90 | 4.9 |
| | Ar21 | I-1 (0.2) | z5 (0.1) z6 (0.1) | (28) 5 g (11) 5 g | DIA (0.02) TMEA (0.02) | W-4 (0.01) | A1/B1 = 60/40 | 89 | 5.0 |
| | Ar22 | I-2 (0.2) | z38 (0.1) z44 (0.1) | (28) 5 g (2) 5 g | TPSA (0.02) PEA (0.02) | W-4 (0.01) | A1/A4 = 95/5 | 91 | 5.2 |
| | Ar23 | I-77 (0.3) | z38 (0.2) | (7) | PEA (0.01) TPA (0.02) | W-4 (0.03) | A1/B2 = 60/40 | 85 | 4.7 |
| | Ar24 | I-83 (0.3) | z58 (0.2) | (28) | PEA (0.02) | W-2 (0.03) | A1/B1 = 70/30 | 82 | 3.9 |
| | Ar25 | I-85 (0.3) | z50 (0.2) | (31) | PEA (0.02) | W-4 (0.03) | A1/B1 = 60/40 | 89 | 4.3 |
| | Ar26 | I-87 (0.3) | z60 (0.2) | (4) | PEA (0.01) DIA (0.02) | W-4 (0.03) | A1/A3 = 60/40 | 92 | 5.6 |
| | Ar27 | I-88 (0.4) | z38 (0.3) | (30) | DIA (0.02) | W-4 (0.03) | A1/A4 = 60/40 | 91 | 6.1 |
| | Ar28 | I-89 (0.3) | z61 (0.2) | (4) | PEA (0.01) | W-4 (0.03) | A1/A3 = 60/40 | 90 | 5.0 |

TABLE 2-continued

| | | (A) Acid generator (g) | Optional acid generator (g) | (B) Resin (10 g) | Basic compound (g) | Surfactant (g) | Solvent (mass ratio) | Threshold pattern falling line width (nm) | Line edge roughness (nm) |
|---|---|---|---|---|---|---|---|---|---|
| | Ar29 | I-90 (0.4) | z38 (0.3) | (30) | DIA (0.02) DIA (0.02) | W-4 (0.03) | A1/A4 = 60/40 | 88 | 4.8 |
| | Ar30 | I-93 (0.4) | z38 (0.3) | (28) | DIA (0.02) | W-4 (0.03) | A1/A4 = 60/40 | 85 | 4.2 |
| Comp. Ex. | ar1 | PAG-A (0.3) | | (1) | DIA (0.03) | W-4 (0.01) | A1/B1 = 70/30 | 109 | 9.5 |

The abbreviations common to Table 2 given above and Tables 3, 4, 6, and 7 given later are summarized below.
[Acid Generator]
PAG-A: triphenylsulfonium nonafluorobutanesulfonate
[Basic Compounds]
TPI: 2,4,5-triphenylimidazole
TPSA: triphenylsulfonium acetate
HEP: N-hydroxyethylpiperidine
DIA: 2,6-diisopropylaniline
DCMA: dicyclohexylmethylamine
TPA: tripentylamine
HAP: hydroxyantipyrine
TBAH: tetrabutylammonium hydroxide
TMEA: tris(methoxyethoxyethyl)amine
PEA: N-phenyldiethanolamine
W-1: Megafac F176 (manufactured by Dainippon Ink & Chemicals, Inc.) (fluorochemical)
W-2: Megafac R08 (manufactured by Dainippon Ink & Chemicals, Inc.) (fluorochemical and silicone)
W-3: polysiloxane polymer KP-341 (manufactured by Shin-Etsu Chemical Co., Ltd.) (silicone)
W-4: Troysol S-366 (manufactured by Troy Chemical Co., Ltd.)
A1: propylene glycol monomethyl ether acetate
A2: 2-heptanone
A3: cyclohexanone
A4: γ-butyrolactone
B1: propylene glycol monomethyl ether
B2: ethyl lactate It is apparent from the results given in Table 2 that the photosensitive compositions of the invention in ArF exposure are less susceptible to pattern falling and attain reduced line edge roughness and excellent pattern profile.

Examples Si-1 to Si-8 and Comparative Example si-1

(1) Formation of Lower Resist Layer
FHi-028DD Resist (resist for i-line; manufactured by FUJIFILM OLIN Co., LTD) was applied to a 6-inch silicon wafer with spin coater Mark 8, manufactured by Tokyo Electron Ltd., and baked at 90° C. for 90 seconds to form an even film having a thickness of 0.55 μm.

This film was further heated at 200° C. for 3 minutes to form a lower resist layer having a thickness of 0.40 μm.

(2) Formation of Upper Resist Layer
Each set of ingredients shown in Table 3 was dissolved in the solvent to prepare a solution having a solid concentration of 11% by mass. This solution was subjected to microfiltration through a membrane filter having an opening diameter of 0.1 μm to prepare a resist composition for upper resist layer formation.

The resist composition for upper resist layer formation was applied on the lower resist layer in the same manner and heated at 130° C. for 90 seconds to form an upper resist layer having a thickness of 0.20 μm.

Resins (SI-1) to (SI-5) in Table 3 are as follows.

| | Molecular weight |
|---|---|
| (SI-1) 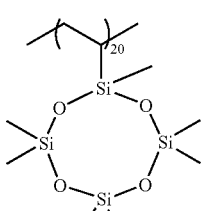 | 15000 |
| (SI-2) 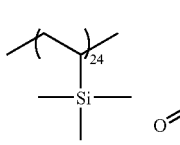 | 14500 |

-continued

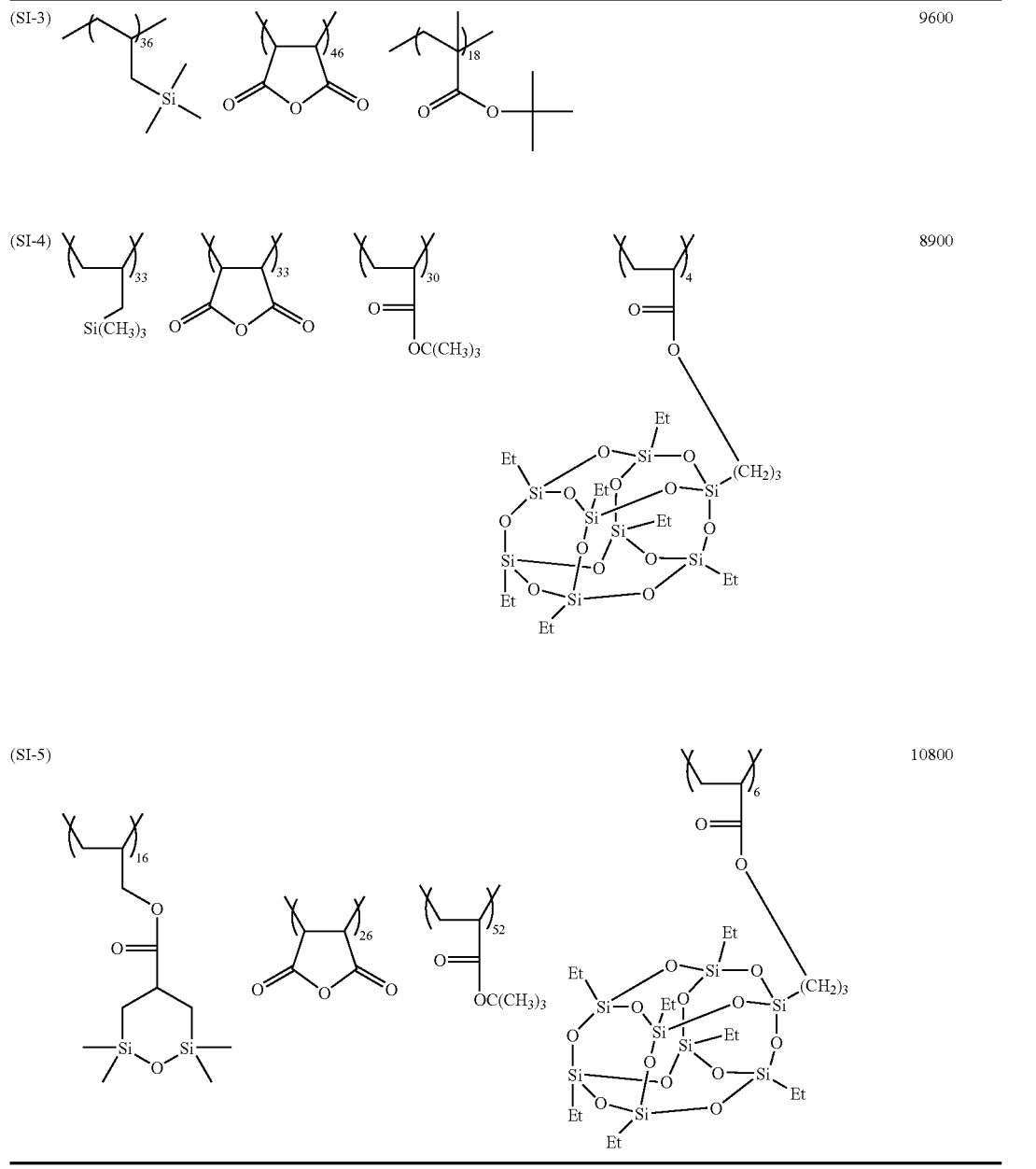

(3) Resist Evaluation

The wafers thus obtained were exposed to light with ArF excimer stepper 9300, manufactured by ISI, while changing the exposure amount using a resolution mask attached to the stepper.

Subsequently, each wafer was heated at 120° C. for 90 seconds. Thereafter, the resist film was developed with a developing solution of tetramethylammonium hydroxide (2.38% by mass) for 60 seconds, rinsed with distilled water, and then dried. Thus, an upper-layer pattern was obtained.

Method of Evaluation for Pattern Falling:

The exposure amount necessary for reproducing a mask pattern comprising 120-nm lines and spaces in a ratio of 1:1 was taken as the optimal exposure amount. Each resist film was exposed in the optimal exposure amount with respect to dense patterns having a line/space ratio of 1:1. The line width for the finest mask pattern which could be reproduced with satisfactory resolution without causing pattern falling was determined as a threshold pattern-falling line width. Method of Evaluation for Line Edge Roughness:

Line edge roughness was examined in the following manner. A 120-nm line/space=1:1 pattern was examined with a length-measuring scanning electron microscope (SEM). In the line pattern, length-direction edges in a range of 5 μm were examined with the length-measuring SEM (S-8840, manufactured by Hitachi, Ltd.) to measure the distance from the standard line where each edge was to be present. This measurement was made on 50 points. A standard deviation was determined and 3σ was calculated.

The results obtained are shown in Table 3.

TABLE 3

| | | (A) Acid generator (g) | Optional acid generator (g) | (B) Resin (10 g) | Basic compound (g) | Surfactant (g) | Solvent (mass ratio) | Threshold pattern-falling line width (nm) | Line edge roughness (nm) |
|---|---|---|---|---|---|---|---|---|---|
| Example | Si-1 | I-1 (0.6) | | SI-1 | DIA (0.03) | W-4 (0.01) | A1 = 100 | 88 | 4.8 |
| | Si-2 | I-2 (0.4) | z14 (0.2) | SI-2 | TPA (0.03) | W-2 (0.02) | A1/A3 = 40/60 | 89 | 4.6 |
| | Si-3 | I-35 (0.2) | z6 (0.2) | SI-3 | HAP (0.02) | W-1 (0.01) | A1/B1 = 60/40 | 88 | 4.6 |
| | Si-4 | I-2 (0.6) | z8 (0.1) | SI-4 | DIA (0.03) | W-4 (0.01) | A1/B1 = 60/40 | 84 | 4.2 |
| | Si-5 | I-1 (0.4) | z57 (0.2) | SI-5 | PEA (0.01) | W-4 (0.01) | A1/A3 = 60/40 | 83 | 4.2 |
| | Si-6 | I-77 (0.3) | z38 (0.2) | SI-1 | PEA (0.02) | W-4 (0.03) | A1/A3 = 60/40 | 88 | 5.5 |
| | Si-7 | I-88 (0.3) | z60 (0.15) | SI-2 | PEA (0.01) DIA (0.02) | W-4 (0.03) | A1/A3 = 80/20 | 92 | 4.8 |
| | Si-8 | I-89 (0.3) | z61 (0.2) | SI-1 | PEA (0.02) | W-4 (0.03) | A1/A3 = 60/40 | 91 | 5.0 |
| Comp. Ex. | si-1 | PAG-A (0.6) | | SI-1 | DIA (0.03) | W-4 (0.01) | A1 = 100 | 95 | 6.9 |

It is apparent from the results given in Table 3 that the photosensitive compositions of the invention, even when used as a two-layer resist, are less susceptible to pattern falling and attain reduced line edge roughness and excellent pattern profile.

Examples F2-1 to F2-13 and Comparative Example f2-1

<Resist Preparation>

Each set of ingredients shown in Table 4 was dissolved in the solvent to prepare a solution having a solid concentration of 5% by mass. This solution was filtered through a 0.1-μm polyethylene filter. Thus, resist fluids were prepared.

Each resist fluid was applied with a spin coater to a silicon wafer treated with hexamethyldisilazane. The coating was dried by heating at 120° C. for 90 seconds with a vacuum contact type hot plate to obtain a resist film having a thickness of 120 nm.

The resist film obtained was pattern-wise exposed to light with an $F_2$ excimer laser stepper (157 nm). Immediately after the exposure, the resist film was heated with a hot plate at 120° C. for 90 seconds. This resist film was developed with a 2.38% by mass aqueous solution of tetramethylammonium hydroxide for 60 seconds and then rinsed with pure water. Thus, sample wafers were obtained. These sample wafers were examined for pattern falling and line edge roughness.

Method of Evaluation for Pattern Falling:

The exposure amount necessary for reproducing a mask pattern comprising 80-nm lines and spaces in a ratio of 1:1 was taken as the optimal exposure amount. The exposure amount was increased from the optimal exposure amount to reduce the pattern line width, and the line width for the finest pattern which could be reproduced with satisfactory resolution without causing pattern falling was determined as a threshold pattern-falling line width.

Method of Evaluation for Line Edge Roughness:

Line edge roughness was examined in the following manner. A 120-nm line/space=1:1 pattern was examined with a length-measuring scanning electron microscope (SEM). In the line pattern, length-direction edges in a range of 5 μm were examined with the length-measuring SEM (S-8840, manufactured by Hitachi, Ltd.) to measure the distance from the standard line where each edge was to be present. This measurement was made on 50 points. A standard deviation was determined and 3σ was calculated.

The results obtained are shown in Table 4.

TABLE 4

| | | (A) Acid generator (g) | Optional acid generator (g) | (B) Resin (10 g) | Basic compound (g) | Surfactant (g) | Solvent (mass ratio) | Threshold pattern-falling line width (nm) | Line edge roughness (nm) |
|---|---|---|---|---|---|---|---|---|---|
| Example | F2-1 | I-1 (0.5) | | FII-1 | DIA (0.03) | W-4 (0.01) | A1/B1 = 70/30 | 47 | 6.7 |
| | F2-2 | I-1 (0.4) | z55 (0.2) | FII-2 | TPA (0.03) | W-2 (0.02) | A1/A3 = 40/60 | 47 | 7.0 |
| | F2-3 | I-2 (0.2) | z6 (0.2) | FII-3 | HAP (0.02) | W-1 (0.01) | A1/B1 = 50/50 | 48 | 6.9 |
| | F2-4 | I-28 (0.3) | z8 (0.1) | FII-4 | DIA (0.03) | W-4 (0.01) | A1/B1 = 60/40 | 48 | 7.2 |
| | F2-5 | I-64 (0.4) | z12 (0.05) | FII-5 | PEA (0.03) | W-4 (0.01) | A1/B1 = 60/40 | 51 | 6.5 |
| | F2-6 | I-2 (0.2) I-67 (0.2) | z36 (0.1) | FII-6 | DIA (0.02) PEA (0.02) | W-4 (0.01) | A1/A3 = 60/40 | 47 | 6.8 |
| | F2-7 | I-68 (0.4) | z40 (0.1) | FII-7 | TMEA (0.03) | W-3 (0.03) | A1/B2 = 80/20 | 48 | 7.0 |
| | F2-8 | I-19 (0.6) | z41 (0.3) | FII-8 | TBAH (0.04) | W-1 (0.005) | A2/B1 = 80/20 | 47 | 7.2 |
| | F2-9 | I-52 (0.2) I-74 (0.2) | z57 (0.3) | FII-9 | HEP (0.03) | W-3 (0.02) | A3/B1 = 70/30 | 47 | 6.8 |
| | F2-10 | I-1 (0.4) | z58 (0.1) | FII-10 | TPSA (0.05) | W-3 (0.01) | A1/A3 = 60/40 | 46 | 7.0 |
| | F2-11 | I-83 (0.3) | z38 (0.2) | FII-1 | PEA (0.02) | W-4 (0.03) | A1/B1 = 60/40 | 55 | 6.0 |
| | F2-12 | I-88 (0.3) | z61 (0.15) | FII-2 | PEA (0.01) | W-4 (0.03) | A1/B1 = 95/5 | 49 | 6.5 |

TABLE 4-continued

| | | (A) Acid generator (g) | Optional acid generator (g) | (B) Resin (10 g) | Basic compound (g) | Surfactant (g) | Solvent (mass ratio) | Threshold pattern-falling line width (nm) | Line edge roughness (nm) |
|---|---|---|---|---|---|---|---|---|---|
| | F2-13 | I-90 (0.3) | z60 (0.2) | FII-1 | DIA (0.02) PEA (0.02) | W-4 (0.03) | A1/B1 = 60/40 | 51 | 5.9 |
| Comp. Ex. | f2-1 | PAG-A (0.5) | | FII-1 | DIA (0.03) | W-4 (0.01) | A1/B1 = 70/30 | 63 | 11.3 |

It is apparent from the results given in Table 4 that the photosensitive compositions of the invention, also in $F_2$ excimer laser exposure, are less susceptible to pattern falling and attain reduced line edge roughness and excellent pattern profile.

Examples KrP-1 to KrP-14 and Comparative Example krp-1

<Resist Preparation>

Each set of ingredients shown in Table 6 was dissolved in the solvent and the resultant solution was filtered through a 0.1-μm polytetrafluoroethylene filter. Thus, positive resist solutions having a solid concentration of 14% by mass were prepared.

The positive resist solutions prepared were evaluated by the methods shown below, and the results obtained are shown in Table 6.

The monomer unit ratio by mole and weight-average molecular weight of each of the resins (R-2) to (R-27) in Table 6 are shown in Table 5 below. The repeating units constituting each of the resins (R-2) to (R-27) are as shown hereinabove.

TABLE 5

| Resin | Repeating unit ratio by mole (left to right units) | Weight-average molecular weight |
|---|---|---|
| R-2 | 60/40 | 12000 |
| R-7 | 60/30/10 | 18000 |
| R-8 | 60/20/20 | 12000 |
| R-9 | 10/50/40 | 13000 |
| R-14 | 75/25 | 12000 |
| R-17 | 10/70/20 | 15000 |
| R-19 | 10/70/20 | 11000 |
| R-22 | 70/30 | 12000 |
| R-23 | 10/60/30 | 8000 |
| R-24 | 50/20/30 | 16000 |
| R-25 | 10/70/20 | 13000 |
| R-27 | 70/10/20 | 12000 |

<Resist Evaluation>

Each positive resist solution prepared was evenly applied with a spin coater to a silicon substrate treated with hexamethyldisilazane. The coating was dried by heating at 120° C. for 90 seconds on a hot plate to form a 0.4-μm resist film.

This resist film was pattern-wise exposed with a KrF excimer laser stepper (NA=0.63) through a mask for a line-and-space pattern. Immediately after the exposure, the resist film was heated on a hot plate at 110° C. for 90 seconds. Furthermore, the resist film was developed with a 2.38% by mass aqueous solution of tetramethylammonium hydroxide at 23° C. for 60 seconds, rinsed with pure water for 30 seconds, and then dried. Thus, line patterns were formed. These line patterns were evaluated for pattern falling and line edge roughness.

Method of Evaluation for Pattern Falling:

The exposure amount necessary for reproducing a mask pattern comprising 150-nm lines and spaces in a ratio of 1:1 was taken as the optimal exposure amount. Each resist film was exposed in the optimal exposure amount with respect to dense patterns having a line/space ratio of 1:1. The line width for the finest mask pattern which could be reproduced with satisfactory resolution without causing pattern falling was determined as a threshold pattern-falling line width. Method of Evaluation for Line Edge Roughness:

Line edge roughness was examined in the following manner. A 150-nm line/space=1:1 pattern was examined with a length-measuring scanning electron microscope (SEM). In the line pattern, length-direction edges in a range of 5 μm were examined with the length-measuring SEM (S-8840, manufactured by Hitachi, Ltd.) to measure the distance from the standard line where each edge was to be present. This measurement was made on 50 points. A standard deviation was determined and 3σ was calculated.

The results obtained are shown in Table 6.

TABLE 6

| | | (A) Acid generator (g) | Optional acid generator (g) | (B) Resin (10 g) | Basic compound (g) | Surfactant (g) | Solvent (mass ratio) | Threshold pattern-falling line width (nm) | Line edge roughness (nm) |
|---|---|---|---|---|---|---|---|---|---|
| Example | KrP-1 | I-1 (0.5) | | R-7 | TPI (0.03) | W-4 (0.01) | A1/B1 = 70/30 | 131 | 5.7 |
| | KrP-2 | I-1 (0.4) | z31 (0.4) | R-8 | TPA (0.03) | W-2 (0.02) | A1/A3 = 40/60 | 132 | 6.2 |
| | KrP-3 | I-2 (0.3) | z6 (0.2) | R-9 | HAP (0.02) | W-1 (0.01) | A1/B1 = 50/50 | 134 | 5.9 |
| | KrP-4 | I-28 (0.3) | z57 (0.1) | R-14 | DCMA (0.03) | W-4 (0.01) | A1/B1 = 60/40 | 130 | 5.8 |

TABLE 6-continued

| | | (A) Acid generator (g) | Optional acid generator (g) | (B) Resin (10 g) | Basic compound (g) | Surfactant (g) | Solvent (mass ratio) | Threshold pattern-falling line width (nm) | Line edge roughness (nm) |
|---|---|---|---|---|---|---|---|---|---|
| | KrP-5 | I-64 (0.4) | z12 (0.05) | R-17 | PEA (0.01) | W-4 (0.01) | A1/B1 = 60/40 | 132 | 6.3 |
| | KrP-6 | I-2 (0.2) I-67 (0.2) | z4 (0.1) | R-19 (5 g) R-27 (5 g) | DIA (0.02) PEA (0.02) | W-4 (0.01) | A1/A3 = 60/40 | 132 | 5.7 |
| | KrP-7 | I-68 (0.4) | z40 (0.1) | R-23 | TMEA (0.03) | W-3 (0.03) | A1/B2 = 80/20 | 132 | 5.8 |
| | KrP-8 | I-19 (0.6) | z31 (0.3) | R-24 | TBAH (0.04) | W-1 (0.005) | A2/B1 = 80/20 | 130 | 5.2 |
| | KrP-9 | I-52 (0.2) I-74 (0.2) | z32 (0.3) | R-25 (5 g) R-2 (5 g) | HEP (0.03) | W-3 (0.02) | A3/B1 = 70/30 | 127 | 5.0 |
| | KrP-10 | I-1 (0.4) | z55 (0.1) | R-27 (5 g) R-22 (5 g) | TPSA (0.05) | W-3 (0.01) | A1/A3 = 60/40 | 128 | 5.0 |
| | KrP-11 | I-82 (0.2) | z38 (0.18) | R-7 | PEA (0.02) | W-4 (0.03) | A1/B1 = 60/40 | 125 | 4.5 |
| | KrP-12 | I-84 (0.2) | z38 (0.15) | R-8 | PEA (0.02) | W-4 (0.03) | A1/B1 = 60/40 | 121 | 5.3 |
| | KrP-13 | I-86 (0.25) | z61 (0.2) | R-9 | PEA (0.02) | W-1 (0.03) | A1/A3 = 60/40 | 129 | 4.9 |
| | KrP-14 | I-89 (0.25) | z60 (0.2) | R-7 | PEA (0.02) | W-4 (0.03) | A1/B1 = 60/40 | 120 | 4.2 |
| Comp. Ex. | krp-1 | PAG-A (0.5) | | R-7 | TPI (0.03) | W-4 (0.01) | A1/B1 = 70/30 | 142 | 8.9 |

It is apparent from the results given in Table 6 that the photosensitive compositions of the invention, even when used as a positive resist composition in KrF excimer laser exposure, are less susceptible to pattern falling and attain reduced line edge roughness and excellent pattern profile.

Examples KrN-1 to KrN-14 and Comparative Example krn-1

<Resist Preparation>

Each set of ingredients shown in Table 7 was dissolved in the solvent and the resultant solution was filtered through a 0.1-μm polytetrafluoroethylene filter. Thus, negative resist solutions having a solid concentration of 14% by mass were prepared.

The negative resist solutions prepared were evaluated in the same manners as in Examples KrP-1 to KrP-10 and Comparative Example krp-1. The results obtained are shown in Table 7.

The structures, molecular weights, and molecular-weight distributions of the alkali-soluble resins in Table 7 are shown below.

| | Mw | Mw/Mn |
|---|---|---|
| P-1 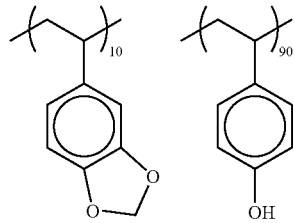 | 17000 | 2.15 |
| P-2 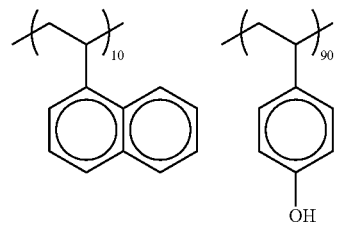 | 16000 | 2.30 |
| P-3 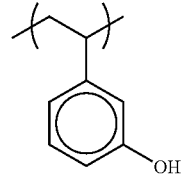 | 19000 | 2.2 |
| P-4 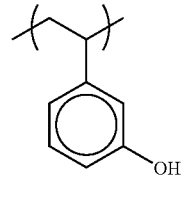 | 12000 | 1.2 |
| P-5 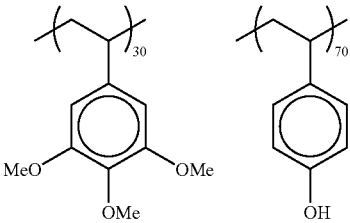 | 21000 | 2.1 |

-continued

| | Mw | Mw/Mn |
|---|---|---|
| P-6 (structure: polymer with pendant phenol –OH group) VP-5000 manufactured by Nippon Soda | 6000 | 1.2 |

The structures of the crosslinking agents in Table 7 are shown below.

TABLE 7

| | | Composition | | | | | | | Evaluation | |
|---|---|---|---|---|---|---|---|---|---|---|
| | | (A) Acid generator (g) | Optional acid generator (g) | (B) Resin (10 g) | Cross-linking agent (g) | Basic compound (g) | Surfactant (g) | Solvent (mass ratio) | Thresold pattern falling line width (nm) | Line edge roughness (nm) |
| Example | KrN-1 | I-1 (0.5) | | P-1 | CL-1 (2) | TPI (0.03) | W-4 (0.01) | A1/B1 = 70/30 | 132 | 5.2 |
| | KrN-2 | I-1 (0.4) | z31 (0.4) | P-2 | CL-2 (3) | TPA (0.03) | W-2 (0.02) | A1/A3 = 40/60 | 130 | 5.1 |
| | KrN-3 | I-2 (0.3) | z6 (0.2) | P-3 | CL-3 (2.5) | HAP (0.02) | W-1 (0.01) | A1/B1 = 50/50 | 131 | 5.5 |
| | KrN-4 | I-28 (0.3) | z57 (0.1) | P-4 | CL-4 (3) | DCMA (0.03) | W-4 (0.01) | A1/B1 = 60/40 | 129 | 5.7 |
| | KrN-5 | I-64 (0.4) | z12 (0.05) | P-5 | CL-5 (1.5) | PEA (0.01) | W-4 (0.01) | A1/B1 = 60/40 | 130 | 5.6 |
| | KrN-6 | I-2 (0.2) I-67 (0.2) | z4 (0.1) | P-2 (5 g) P-6 (5 g) | CL-1(2) CL-5(2) | DIA (0.02) PEA (0.02) | W-4 (0.01) | A1/A3 = 60/40 | 130 | 5.4 |
| | KrN-7 | I-68 (0.4) | z40 (0.1) | P-1 | CL-6 (3) | TMEA (0.03) | W-3 (0.03) | A1/B2 = 80/20 | 131 | 5.9 |
| | KrN-8 | I-19 (0.6) | z31 (0.3) | P-6 | CL-1 (3) | TBAH (0.04) | W-1 (0.005) | A2/B1 = 80/20 | 132 | 5.7 |
| | KrN-9 | I-52 (0.2) I-74 (0.2) | z32 (0.3) | P-3 | CL-2 (2) | HEP (0.03) | W-3 (0.02) | A3/B1 = 70/30 | 126 | 5.8 |
| | KrN-10 | I-1 (0.4) | z55 (0.1) | P-4 | CL-4 (2.5) | TPSA (0.05) | W-3 (0.01) | A1/A3 = 60/40 | 127 | 5.7 |
| | KrN-11 | I-83 (0.2) | z38 (0.14) | P-1 | CL-4 (3) | PEA (0.02) | W-4 (0.03) | A1/B1 = 60/40 | 130 | 5.5 |
| | KrN-12 | I-77 (0.2) | z59 (0.15) | P-2 | CL-4 (4) | PEA (0.01) DIA (0.02) | W-2 (0.03) | A1/A3 = 60/40 | 125 | 4.3 |
| | KrN-13 | I-88 (0.25) | z58 (0.2) | P-3 | CL-1 (2) | PEA (0.01) DIA (0.02) | W-3 (0.03) | A1/B1 = 60/40 | 133 | 5.1 |
| | KrN-14 | I-89 (0.25) | z60 (0.2) | P-1 | CL-1 (2) | PEA (0.01) DIA (0.02) | W-4 (0.03) | A1/B1 = 60/40 | 128 | 4.9 |
| Comp. Ex. | krn-1 | PAG-A (0.5) | | P-1 | CL-1 (2) | TPI (0.03) | W-4 (0.01) | A1/B1 = 70/30 | 140 | 9.2 |

TABLE 7-continued
| | Composition | | | | | | Evaluation | |
|---|---|---|---|---|---|---|---|---|
| | | | | | | | Thresold pattern | |
| (A) Acid generator (g) | Optional acid generator (g) | (B) Resin (10 g) | Cross-linking agent (g) | Basic compound (g) | Surfactant (g) | Solvent (mass ratio) | falling line width (nm) | Line edge roughness (nm) |
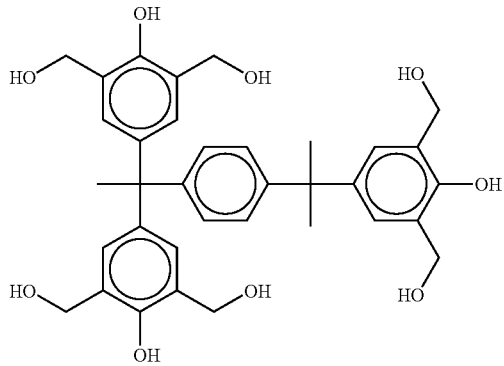
CL-1
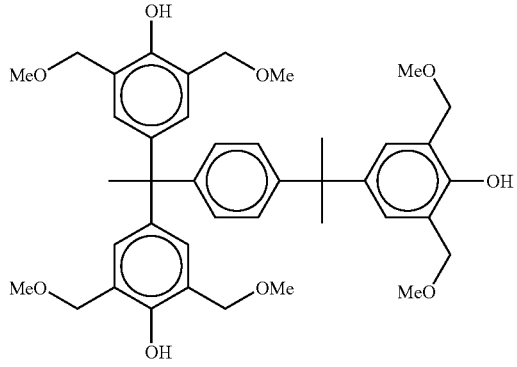
CL-2
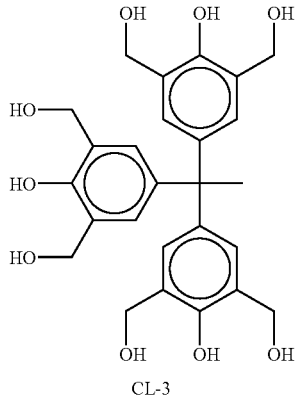
CL-3

TABLE 7-continued

|  | Composition | | | | | | Evaluation | |
|---|---|---|---|---|---|---|---|---|
| | | | | | | | Thresold pattern | |
| (A) Acid generator (g) | Optional acid generator (g) | (B) Resin (10 g) | Cross-linking agent (g) | Basic compound (g) | Surfactant (g) | Solvent (mass ratio) | falling line width (nm) | Line edge roughness (nm) |

CL-4

CL-5

CL-6

It is apparent from the results given in Table 7 that the photosensitive compositions of the invention, even when used as a negative resist composition in KrF excimer laser exposure, are less susceptible to pattern falling and attain reduced line edge roughness and excellent pattern profile.

Examples EBP-1 to EBP-14 and Comparative Example ebp-1

<Resist Preparation>

Each set of ingredients shown in Table 6 was dissolved in the solvent and the resultant solution was filtered through a 0.1-μm polytetrafluoroethylene filter. Thus, positive resist solutions having a solid concentration of 12% by mass were prepared.

The positive resist solutions prepared were evaluated by the methods shown below, and the results obtained are shown in Table 8.

<Resist Evaluation>

Each positive resist solution prepared was evenly applied with a spin coater to a silicon substrate treated with hexamethyldisilazane. The coating was dried by heating at 120° C. for 60 seconds on a hot plate to form a 0.3-μm resist film.

This resist film was irradiated using a lithographic apparatus for electron beam projection (accelerating voltage, 100 keV) manufactured by Nikon Corp. Immediately after the irradiation, the resist film was heated at 110° C. for 90 seconds on a hot plate. Furthermore, the resist film was developed at 23° C. for 60 seconds with an aqueous tetramethylammonium hydroxide solution having a concentration of 2.38% by mass, rinsed with pure water for 30 seconds, and then dried. Thus, line-and-space patterns were formed.

Method of Evaluation for Pattern Falling:

The irradiation amount necessary for reproducing a mask pattern comprising 100-nm lines and spaces in a ratio of 1:1 was taken as the optimal irradiation amount. Each resist film was irradiated in the optimal irradiation amount. The line width for the finest mask pattern which could be reproduced with satisfactory resolution without causing pattern falling was determined as a threshold pattern-falling line width.

Method of Evaluation of Line Edge Roughness:

Line edge roughness was examined in the following manner. A 100-nm line/space=1:1 pattern was examined with a length-measuring electron microscope (SEM). In the line pattern, length-direction edges in a range of 5 μm were examined with the length-measuring SEM (S-8840, manufactured by Hitachi, Ltd.) to measure the distance from the standard line where each edge was to be present. This measurement was made on 50 points. A standard deviation was determined and 3σ was calculated.

TABLE 8

|  |  | Threshold pattern-falling line width (nm) | Line edge roughness (nm) |
|---|---|---|---|
| Example | EBP-1 | 81 | 5.9 |
|  | EBP-2 | 80 | 6.0 |
|  | EBP-3 | 81 | 6.0 |
|  | EBP-4 | 80 | 5.8 |
|  | EBP-5 | 79 | 6.2 |
|  | EBP-6 | 82 | 5.8 |
|  | EBP-7 | 81 | 5.7 |
|  | EBP-8 | 74 | 5.2 |
|  | EBP-9 | 71 | 5.0 |
|  | EBP-10 | 70 | 5.1 |
|  | EBP-11 | 78 | 5.1 |
|  | EBP-12 | 75 | 5.2 |
|  | EBP-13 | 80 | 4.9 |
|  | EBP-14 | 77 | 4.2 |
| Comp. Ex. | ebp-1 | 88 | 8.2 |

It is apparent from the results given in Table 8 that the photosensitive compositions of the invention, even when used as a positive resist composition in electron beam irradiation, are less susceptible to pattern falling and attain reduced line edge roughness and excellent pattern profile.

Examples EBN-1 to EBN-14 and Comparative Example ebn-1

<Resist Preparation>

Each set of ingredients shown in Table 7 was dissolved in the solvent and the resultant solution was filtered through a 0.1-μm polytetrafluoroethylene filter. Thus, negative resist solutions having a solid concentration of 12% by mass were prepared.

The negative resist solutions prepared were evaluated by the methods shown below, and the results obtained are shown in Table 9.

<Resist Evaluation>

Each negative resist solution prepared was evenly applied with a spin coater to a silicon substrate treated with hexamethyldisilazane. The coating was dried by heating at 120° C. for 60 seconds on a hot plate to form a 0.3-μm resist film.

This resist film was irradiated using a lithographic apparatus for electron beam projection (accelerating voltage, 100 keV) manufactured by Nikon Corp. Immediately after the irradiation, the resist film was heated at 110° C. for 90 seconds on a hot plate. Furthermore, the resist film was developed at 23° C. for 60 seconds with an aqueous tetramethylammonium hydroxide solution having a concentration of 2.38% by mass, rinsed with pure water for 30 seconds, and then dried. Thus, line-and-space patterns were formed.

Method of Evaluation for Pattern Falling:

The irradiation amount necessary for reproducing a mask pattern comprising 100-nm lines and 150-nm spaces was taken as the optimal irradiation amount. Each resist film was irradiated in the optimal irradiation amount. The line width for the finest mask pattern which could be reproduced with satisfactory resolution without causing pattern falling was determined as a threshold pattern-falling line width.

Method of Evaluation of Line Edge Roughness:

Line edge roughness was examined in the following manner. A 100-nm line/150-nm space pattern was examined with a length-measuring electron microscope (SEM). In the line pattern, length-direction edges in a range of 5 μm were examined with the length-measuring SEM (S-8840, manufactured by Hitachi, Ltd.) to measure the distance from the standard line where each edge was to be present. This measurement was made on 50 points. A standard deviation was determined and 3σ was calculated.

TABLE 9

|  |  | Threshold pattern-falling line width (nm) | Line edge roughness (nm) |
|---|---|---|---|
| Example | EBN-1 | 79 | 5.3 |
|  | EBN-2 | 81 | 5.0 |
|  | EBN-3 | 80 | 5.8 |
|  | EBN-4 | 78 | 5.4 |
|  | EBN-5 | 81 | 5.3 |
|  | EBN-6 | 80 | 5.7 |
|  | EBN-7 | 79 | 5.8 |
|  | EBN-8 | 76 | 6.0 |
|  | EBN-9 | 76 | 5.9 |
|  | EBN-10 | 75 | 5.5 |
|  | EBN-11 | 82 | 4.8 |
|  | EBN-12 | 85 | 5.0 |
|  | EBN-13 | 76 | 5.2 |
|  | EBN-14 | 74 | 4.8 |
| Comp. Ex. | ebn-1 | 90 | 9.0 |

It is apparent from the results given in Table 9 that the photosensitive compositions of the invention, even when used as a negative resist composition in electron beam irradiation, are less susceptible to pattern falling and attain reduced line edge roughness and excellent pattern profile.

Examples EUVP-1 to EUVP-14 and Comparative Example euvp-1

A posi-type resist solution of 8% by weight solid concentration was prepared by dissolving the ingredients shown in the aforementioned Table 6 and filtering the resulting solution through a 0.1-μm polytetrafluoroethylene filter. Then, each sample was evaluated as follows.

<Resist Evaluation>

The posi-type resist solution thus prepared was uniformly coated on a silicon wafer which had been subjected to hexamethyldisilazane treatment by means of a spin coater, and the wafer thus coated was dried by heating on a hot plate at 120° C. for 60 sec to provide a resist film of 0.15 μm thickness. The resulting resist film was uniformly exposed with use of EUV light (wavelength=13 nm) by changing the exposure amount by 0.5 mJ increment over the range of from 0 to 10.0 mJ, and further baked at 110° C. for 90 sec. Thereafter the dissolving speed for each exposure amount was measured by using a 2.38% by weight tetramethylammonium hydroxide (TMAH) aqueous solution to give a sensitivity curve. In this sensitivity curve, sensitivity was defined by the exposure amount at which the dissolving speed of resist saturates. In addition, dissolving contrast (γ value) was calculated from the gradient of the linear portion of the sensitivity curve. The larger the γ value is, the more dissolving contrast preferably increases.

The evaluation result is shown in the following Table 10.

TABLE 10

|  |  | Sensitivity (mJ/cm²) | γ value |
|---|---|---|---|
| Example | EUVP-1 | 1.9 | 12.1 |
|  | EUVP-2 | 2.1 | 10.3 |
|  | EUVP-3 | 2.3 | 10.8 |
|  | EUVP-4 | 2.1 | 12.1 |
|  | EUVP-5 | 1.9 | 10.3 |
|  | EUVP-6 | 1.9 | 10.3 |
|  | EUVP-7 | 2.4 | 10.8 |
|  | EUVP-8 | 2.2 | 12.1 |
|  | EUVP-9 | 2.3 | 10.8 |
|  | EUVP-10 | 2.0 | 12.1 |
|  | EUVP-11 | 2.2 | 10.3 |
|  | EUVP-12 | 2.1 | 10.8 |
|  | EUVP-13 | 1.9 | 10.8 |
|  | EUVP-14 | 1.8 | 11.1 |
| Comparative Example | euvp-1 | 3.5 | 6.9 |

From the result in Table 10, it is seen in the performance evaluation based on the irradiation of EUV light that the compositions of the present invention is superior compared with that of Comparative Example as they exhibit higher sensitivities as well as contrasts.

<Resist Preparation>

A posi-type resist solution of 7% by weight solid concentration was prepared by dissolving the ingredients for each of Examples Ar 1 to Ar 30 and filtering the resulting solution through a 0.1-μm polytetrafluoroethylene filter. Then, each posi-type resist solution was evaluated according to the following method.

<Resolution Evaluation>

An organic anti-reflection film ARC29A (manufactured by Nissan Chemical Industries, Ltd.) was coated on a silicon wafer, and baked at 205° C. for 60 sec to form a 78 nm thick anti-reflection film. The resist composition prepared above was coated on the anti-reflection film and baked at 115° C. for 60 sec to form a 150 nm thick resist film. For the wafer thus prepared, 2-beam interference exposure was conducted with use of pure water as the immersion fluid (wet exposure). Meanwhile, in this 2-beam interference (wet) exposure, a laser 1, a diaphragm 8, a shutter 3, three reflection mirrors 4, 5 and 6 and a collimator lens 7 were used as shown in FIG. 1 whereby the wafer 10 having the anti-reflection film and resist film, resting on a wafer state 11, was subjected to exposure through the immersion fluid (pure water) 9. The wavelength of the laser 1 was 193 nm, and a prism 8 that can form a 65 nm interval line-and-space pattern was used. Immediately after exposure, the wafer was heated at 115° C. for 90 sec, and thereafter developed with a tetramethylammonium hydroxide aqueous solution (2.38% by weight) for 60 sec. After rinsing with pure water, the resist pattern obtained by spin-drying was examined with a scanning electron microscope (Hitachi S-9260) to confirm that the 65 nm interval line-and-space pattern is resolved.

The composition of the present application has a desirable image-forming capability even in the method of exposure via an immersion fluid.

The invention can provide: a photosensitive composition which is less apt to suffer pattern falling and is effective in reducing line edge roughness; a method of pattern formation with the composition; and a compound useful in the photosensitive composition.

The entire disclosure of each and every foreign patent application from which the benefit of foreign priority has been claimed in the present application is incorporated herein by reference, as if fully set forth.

What is claimed is:

1. A photosensitive composition comprising (A) a compound which, upon irradiation with one of an actinic ray and a radiation, generates an acid represented by one of formulae (I) and (I'):

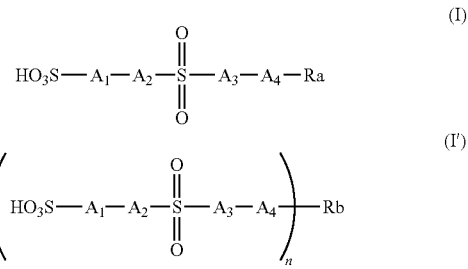

wherein $A_1$ represents an alkylene group whose alkylene chain may have an oxygen or sulfur atom or a connecting group represented by —C(=O)— group or ester group therein;

$A_2$ and $A_3$ each independently represents a single bond, an oxygen atom, or —N(Rx)-; Rx represents an aryl group, an alkyl group, or a cycloalkyl group; $A_4$ represents a single bond or —C(=O)—;

Ra represents a group selected from the group consisting of an ethyl group, a n-propyl group, a n-butyl group, a n-pentyl group, a n-hexyl group, a n-octyl group, a n-dodecyl group, a n-tetradecyl group, a n-octadecyl group, a branched alkyl group, a cycloalkyl group, an aryl group which has a substitutent, an aralkyl group, and an alkenyl group;

n represents 2 or 3;

Rb represents a connecting group having a valence of n; and when $A_3$ is —N(Rx)-, Rx is bonded to one of Ra and Rb to form a ring; and (B) a resin which decomposes by an action of an acid to increase a solubility of the resin in an alkaline developer.

2. The photosensitive composition of claim 1, wherein the resin (B) comprises a structural unit of hydroxystyrene.

3. The photosensitive composition of claim 1, wherein the resin (B) comprises a repeating unit having a monocyclic or polycyclic hydrocarbon structure.

4. The photosensitive composition of claim 3, wherein the repeating unit having the monocyclic or polycyclic hydrocarbon structure in the resin (B) is a repeating unit which comprises at least one of:

a repeating unit derived from a member selected from 2-alkyl-2-adamantyl (meth)acrylate and dialkyl(1-adamantyl)methyl (meth)acrylate;

a repeating unit having a lactone structure; and a repeating unit having one or more hydroxy groups.

5. The photosensitive composition of claim 1, wherein the resin (B) comprises a repeating unit having one or more alcoholic hydroxy groups.

6. The photosensitive composition of claim 5, wherein the repeating unit having one or more alcoholic hydroxy groups in the resin (B) is a repeating unit containing at least one member selected from a monohydroxyadamantane structure, a dihydroxyadamantane structure, and a trihydroxyadamantane structure.

7. The photosensitive composition of claim 1, wherein the resin (B) comprises a repeating unit having a lactone structure.

8. The photosensitive composition of claim 1, wherein the resin (B) comprises: at least one kind of repeating methacrylic ester units; and at least one kind of repeating acrylic ester units.

9. The photosensitive composition of claim 8, wherein the resin (B) comprises a hexafluoro-2-propanol structure.

10. The photosensitive composition of claim 1, wherein the resin (B) has a fluorine atom.

11. The photosensitive composition of claim 1, further comprising (C) a dissolution inhibitive compound having a molecular weight of 3,000 or lower which decomposes by an action of an acid to increase the solubility of the dissolution inhibitive compound in an alkaline developer.

12. The photosensitive composition of claim 1, further comprising a basic compound, a fluorochemical surfactant or a silicone surfactant.

13. The photosensitive composition of claim 12, wherein the resin (B) further comprises a repeating unit having a carboxy group.

14. The photosensitive composition of claim 1, wherein ingredient (B) comprises at least one of:
a repeating unit derived from a member selected from 2-alkyl-2-adamantyl (meth)acrylate and dialkyl(1-adamantyl)methyl (meth)acrylate; and a repeating unit having a hydroxystyrene structure.

15. A method of pattern formation comprising:
forming a film with a photosensitive composition of claim 1;
exposing the film to form an exposed film; and
developing the exposed film.

16. The photosensitive composition of claim 1, wherein $A_1$ is an alkylene group substituted by one or more fluorine atoms.

17. The photosensitive composition of claim 1, wherein the alkylene group represented by $A_1$ is a perfluoroalkylene group.

18. A photosensitive composition comprising:
(A) a compound which, upon irradiation with one of an actinic ray and a radiation, generates an acid represented by one of formulae (I) and (I'):

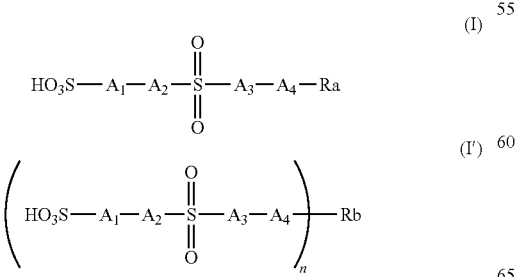

wherein
$A_1$ represents an alkylene group;
$A_2$ and $A_3$ each independently represents a single bond, an oxygen atom, or —N(Rx)-; Rx represents an aryl group, an alkyl group, or a cycloalkyl group;
$A_4$ represents a single bond or —C(=O)—;
Ra represents a group selected from the group consisting of an ethyl group, a n-propyl group, a n-butyl group, a n-pentyl group, a n-hexyl group, a n-octyl group, a n-dodecyl group, a n-tetradecyl group, a n-octadecyl group, a branched alkyl group, a cycloalkyl group, an aryl group which has a substitutent, an aralkyl group, and an alkenyl group;
n represents 2 or 3;
Rb represents a connecting group having a valence of n; and
when $A_3$ is —N(Rx)-, Rx is bonded to one of Ra and Rb to form a ring;
(D) a resin soluble in an alkaline developer; and
(E) an acid-sensitive crosslinking agent which, by an action of an acid, crosslinks the resin (D).

19. The photosensitive composition of claim 18, further comprising a basic compound, a fluorochemical surfactant or a silicone surfactant.

20. The photosensitive composition of claim 18, wherein $A_1$ is an alkylene group substituted by one or more fluorine atoms.

21. A photosensitive composition comprising (A) a compound which, upon irradiation with one of an actinic ray and a radiation, generates an acid represented by one of formulae (I) and (I'):

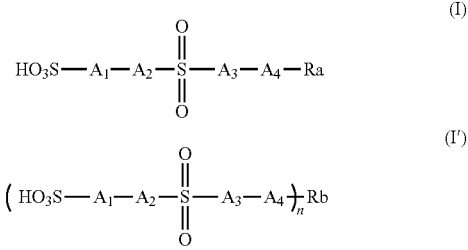

wherein
$A_1$ represents a divalent connecting group;
$A_2$ and $A_3$ each independently represents a single bond, an oxygen atom, or —N(Rx)-; Rx represents an aryl group, an alkyl group, or a cycloalkyl group; $A_4$ represents a single bond or —C(=O)—;
Ra represents an organic group having 2 to 20 carbon atoms;
n represents 2 or 3;
Rb represents a connecting group having a valence of n; and
when $A_3$ is —N(Rx)-, Rx may be bonded to one of Ra and Rb to form a ring; and
(B) a resin which decomposes by an action of an acid to increase a solubility of the resin in an alkaline developer, and which has a fluorine atom.

22. The photosensitive composition of claim 21, wherein the resin (B) comprises a repeating unit having a monocyclic or polycyclic hydrocarbon structure.

23. The photosensitive composition of claim 21, wherein the resin (B) comprises a repeating unit having one or more alcoholic hydroxy groups.

24. The photosensitive composition of claim 23, wherein the repeating unit having one or more alcoholic hydroxy groups in the resin (B) is a repeating unit containing at least one member selected from a monohydroxyadamantane structure, a dihydroxyadamantane structure, and a trihydroxyadamantane structure.

25. The photosensitive composition of claim 21, wherein the resin (B) comprises a repeating unit having a lactone structure.

26. The photosensitive composition of claim 21, further comprising a basic compound, a fluorochemical surfactant or a silicone surfactant.

27. A method of pattern formation comprising:
forming a film with a photosensitive composition of claim 21;
exposing the film to form an exposed film; and
developing the exposed film.

28. The photosensitive composition of claim 21, wherein $A_3$ represents a single bond or —N(Rx)-.

29. The photosensitive composition of claim 21, wherein $A_2$ represents an oxygen atom or —N(Rx)-.

30. A photosensitive composition comprising (A) a compound which, upon irradiation with one of an actinic ray and a radiation, generates an acid represented by one of formulae (I) and (I'):

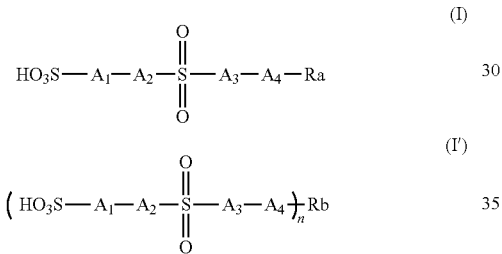

wherein
$A_1$ represents a divalent connecting group;
$A_2$ represents an oxygen atom or —N(Rx)-;
$A_3$ represents a single bond, an oxygen atom, or —N(Rx)-;
Rx represents a hydrogen atom, an aryl group, an alkyl group, or a cycloalkyl group;
$A_4$ represents a single bond or —C(=O)—;
Ra represents a hydrogen atom or an organic group;
n represents 2 or 3;
Rb represents a connecting group having a valence of n; and
when $A_3$ is —N(Rx)-, Rx may be bonded to one of Ra and Rb to form a ring; and (B) a resin having a lactone structure represented by any one of the following formulae (V-1) to (V-5):

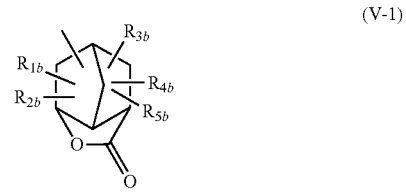

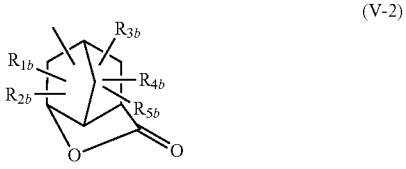

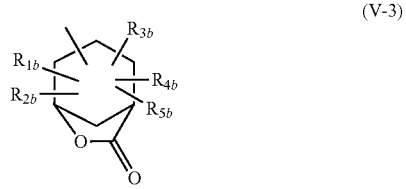

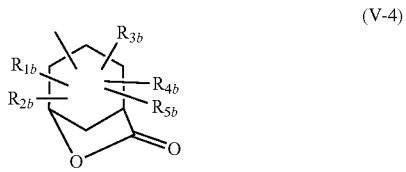

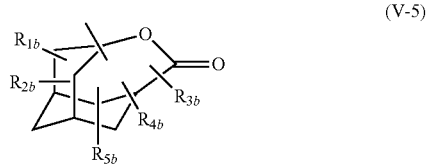

wherein $R_{1b}$ to $R_{5b}$ each independently represents a hydrocarbon atom or an alkyl, cycloalkyl, alkoxy, alkoxycarbonyl, alkylsulfonylamino, or alkenyl group, provided that two of $R_{1b}$ to $R_{5b}$ may be bonded to each other to form a ring.

* * * * *